United States Patent
Otsuka et al.

(10) Patent No.: US 7,939,307 B2
(45) Date of Patent: May 10, 2011

(54) DELETION MUTANT OF MULTI-COPPER OXIDASE AND ITS USE IN DYEING

(75) Inventors: Kaori Otsuka, Osaka (JP); Yoshio Tsujino, Osaka (JP); Yusuke Konno, Kanazawa (JP); Shinji Kurose, Kanazawa (JP); Kunishige Kataoka, Kanazawa (JP); Takeshi Sakurai, Kanazawa (JP)

(73) Assignees: National University Corporation Kanazawa University, Kanazawa-shi (JP); Mandom Corporation, Osaka-shi (JP)

( * ) Notice: Subject to any disclaimer, the term of this patent is extended or adjusted under 35 U.S.C. 154(b) by 260 days.

(21) Appl. No.: 12/084,287

(22) PCT Filed: Apr. 14, 2006

(86) PCT No.: PCT/JP2006/307960
§ 371 (c)(1),
(2), (4) Date: Oct. 10, 2008

(87) PCT Pub. No.: WO2007/063614
PCT Pub. Date: Jun. 7, 2007

(65) Prior Publication Data
US 2010/0205754 A1 Aug. 19, 2010

(30) Foreign Application Priority Data

Dec. 2, 2005 (JP) ................................. 2005-349296

(51) Int. Cl.
C12N 9/02 (2006.01)
C12N 15/00 (2006.01)
C12N 1/20 (2006.01)
C07H 21/04 (2006.01)
C09B 67/00 (2006.01)

(52) U.S. Cl. ................ 435/189; 435/252.33; 435/320.1; 536/23.2; 8/401

(58) Field of Classification Search .................. None
See application file for complete search history.

(56) References Cited

U.S. PATENT DOCUMENTS 5,981,243 A 11/1999 Berka et al.
2005/0170485 A1 8/2005 Tsujino et al.
2006/0021152 A1 2/2006 Tsujino et al.

FOREIGN PATENT DOCUMENTS

JP 10-501137 A 2/1998
WO WO-95/33836 A1 12/1995
WO WO-2004/020617 A1 3/2004

Primary Examiner — Nashaat T Nashed
(74) Attorney, Agent, or Firm — Birch, Stewart, Kolasch & Birch, LLP

(57) ABSTRACT

Modified CueO having excellent enzymatic activity and a composition for dyeing keratin fiber which contains the enzyme. A recombinant protein having an enzymatic activity for oxidizing p-phenylenediamine, the protein is obtained by removing from CueO at least one member selected from the group consisting of helix 5, helix 6, and helix 7; and the composition for dyeing keratin fiber containing the recombinant protein and an oxidation dye.

14 Claims, 5 Drawing Sheets

DELETION MUTANT OF MULTI-COPPER OXIDASE AND ITS USE IN DYEING

TECHNICAL FIELD

The present invention relates to a recombinant protein obtained by an alteration of CueO, a gene encoding the recombinant protein, a recombinant vector containing the gene, a transformant containing the recombinant vector, a process for producing the recombinant protein, a composition for dyeing keratin fiber which contains the recombinant protein, and a method of dying keratin fiber.

BACKGROUND ART

CueO is a protein that plays a role in protecting enzymes in periplasm of *Escherichia coli* from copper-mediated damage. CueO produced from *Escherichia coli* is a monomer with 516 residues and a molecular weight of 56555 Da, while N-terminal 28 residues serve as a signal sequence and are cleaved upon transferring into periplasm so as to give a mature protein with 488 residues and a molecular weight of 53409 Da.

CueO includes 4 copper atoms per molecule, and it is classified as a multi-copper oxidase family. CueO is different from laccase as it has significantly low activity for oxidizing a phenol compound such as 2,6-dimethoxyphenol or catechol, or does not oxidize at all. CueO has a binding site for $5^{th}$ copper, and in the presence of exogenous copper, it exhibits a phenol oxidase activity. CueO is a protein encoded by a gene known as yacK, and amino acid sequences thereof and DNA sequences encoding thereof are reported in Non-Patent Document 1. The fundamental characteristics are reported in Non-Patent Document 2 and Non-Patent Document 3.

Non-Patent Document 2 is disclosing that CueO exhibits significantly low enzymatic activity for oxidizing p-phenylenediamine, 2,6-dimethoxyphenol, or the like, or does not exhibit the activity at all, but this enzymatic activity can be improved under co-existence of divalent copper. However, the above-mentioned enzymatic activity of CueO in the copper-free system is not sufficient for a use, particularly, in dyeing.

From the past, for dyeing keratin fiber including hair and various fibers, oxidation dyes have been used to maintain the dyeing effect. The oxidation dye achieves dyeing by color development via an oxidation reaction and a polymerization reaction. The oxidation dye is for forming a permanent dyeing agent.

In order to proceed the oxidation and polymerization reaction of the oxidation dye, an oxidizing agent such as hydrogen peroxide has been used from the past. In such case, when the oxidation dye penetrated into the hair undergoes oxidative polymerization, high molecular weight coloring materials are formed and deposited inside the hair cortex. Here, since the hydrogen peroxide is highly reactive, full attention is required in handling. In addition, damages to scalp or hair due to a combination use of alkali and hydrogen peroxide have been the problem. Further, a using method thereof is complicated as the dye is a two-part type agent in which an oxidation dye and an alkaline agent are blended as a first agent and hydrogen peroxide is blended as a second agent which are mixed at the time of use.

In consequent, there has been made an attempt to carry out a direct oxidative polymerization of oxidation dye by employing an enzyme instead of an oxidizing agent. For such enzyme, multi-copper oxidase has been suggested. The multi-copper oxidase directly oxidizes the substrate without causing reactive oxygen species such as hydrogen peroxide, and thus is suited for various chemical reactions such as color development, discoloring, and decomposition, which are caused by extremely stable oxidation of the substrate.

As such multi-copper oxidase for a use in dyeing, specifically, a culture from a strain belonging to the genus *Flammulina*, wherein the culture has phenol oxidase-like activity (see Patent Document 1); a neutral phenol oxidase derived from a basidiomycete belonging to the genus *Flammulina* (see Patent Document 2); or a laccase derived from *Myceliophthora thermophila* (see Patent Document 3) has been proposed for a use.

When dyeing of keratin fiber is carried out under an acidic or neutral condition, discoloring is more easily achieved. For the purpose of improving and maintaining the dyeing effect by allowing swelling of keratin fiber such for the oxidation dye to penetrate into the hair cortex and thereby allowing deposition of the high molecular weight dye materials inside the hair cortex, dyeing with the oxidation dye is preferably carried out under an alkaline condition.

However, neutral phenol oxidases disclosed in Patent Document 1 and Patent Document 2 have an optimum pH near a neutral pH, and thus are not suited for a use in an alkaline condition. Also, the oxidases have been difficult to be used in practical because the stability near a neutral pH which is the optimum pH is low. Further, there has been a problem in these neutral phenol oxidases that color matching with a direct dye is difficult as they have a property of catalyzing the decomposition/discoloring of a direct dye.

The laccase derived from *Myceliophthora thermophila* disclosed in Patent Document 3 also has an optimum pH of 6.5, thus is not suited for a use in an alkaline condition.

Patent Document 1: Pamphlet of Int. Pub. No. 2004/020617

Patent Document 2: Pamphlet of Int. Pub. No. 2004/078958

Patent Document 3: PCT Japanese Translation Patent Publication No. 10-501137

Non-Patent Document 1: 'SCIENCE', 1997, 227(5331), 1453-1474

Non-Patent Document 2: 'JOURNAL OF BACTERIOLOGY', August 2001, 4866-4875

Non-Patent Document 3: 'THE JOURNAL OF BIOLOGICAL CHEMISRY', August 2003, Vol. 278, 34, 31958-31963

SUMMARY OF THE INVENTION

The present invention is made under these circumstances and an object of which is to provide:

(1) modified-type CueO excellent in enzymatic activity for oxidizing p-phenylenediamine or the like, as compared to wild-type CueO; and (2) a composition for dyeing keratin fiber in which the oxidation polymerization of an oxidation dye proceeds efficiently by employing an enzyme in place of an oxidizing agent such as hydrogen peroxide and which is capable of being prepared into a one-part agent, where the composition is capable of efficiently dyeing keratin fiber in a wide range of pH region including an alkaline condition, as well as is stable at a wide range of temperature and pH without impairing the toning ability of the direct dye; and a method of dyeing keratin fiber by employing the above-mentioned enzyme.

The present inventors have carried out extensive studies, and as a result, they have found that a recombinant protein obtained by removing from a wild-type CueO at least one member selected from the group consisting of helix 5, helix 6, and helix 7 has characteristics shown below. Thus, they have completed the invention.

(1) The protein has an enzymatic activity that efficiently catalyzes the direct oxidative polymerization of various oxidation dyes, where this enzymatic activity is excellent as compared to that of the wild-type CueO.

(2) The protein exhibits sufficient oxidative polymerization activity over a wide range of pH values from weak acid to alkali, and has an optimum pH in an alkaline region.

(3) The protein is not provided with a property of decomposing a direct dye.

(4) The protein exhibits excellent stability in a wide range of temperature and pH, even in an alkaline region including an optimum pH.

That is, the invention relates to the followings:

[1] a recombinant protein having an enzymatic activity for oxidizing p-phenylenediamine, the protein is obtained by removing from CueO at least one member selected from the group consisting of helix 5, helix 6, and helix 7;

[2] the recombinant protein as described in [1], which is obtained by removing at the least helix 5 from CueO;

[3] the recombinant protein as described in [1] or [2], which is obtained by removing helix 5, helix 6, and helix 7, from CueO, and inserting a spacer thereinto instead;

[4] the recombinant protein as described in [3], which comprises an amino acid sequence represented by SEQ ID NO: 4;

[5] a gene encoding the recombinant protein described in any one of [1] to [4];

[6] a recombinant vector comprising the gene described in [5];

[7] a transformant comprising the recombinant vector described in [6];

[8] the transformant as described in [7], wherein Deposit Number is FERM BP-10431;

[9] a process for producing the recombinant protein described in any one of [1] to [4], comprising culturing the transformant described in [7] or [8], and collecting a produced recombinant protein;

[10] a composition for dyeing keratin fiber, comprising the recombinant protein described in any one of [1] to [4] and an oxidation dye;

[11] the composition for dyeing keratin fiber as described in [10], further comprising an alkaline compound;

[12] the composition for dyeing keratin fiber as described in [10] or [11], wherein the keratin fiber is hair;

[13] a method of dyeing keratin fiber, comprising bringing keratin fiber into contact with an oxidation dye in the presence of the recombinant protein described in any one of [1] to [4] under an oxygen-containing atmosphere; and

[14] the dyeing method as described in [13], wherein the contacting process is carried out under an alkaline condition.

DETAILED DESCRIPTION OF THE INVENTION

Hereinbelow, the invention will be explained.

First, the recombinant protein of the invention will be described.

The recombinant protein of the invention is a protein having an enzymatic activity for oxidizing p-phenylenediamine, and is obtained by removing from CueO at least one member selected from the group consisting of helix 5, helix 6, and helix 7.

The above-mentioned CueO may either be naturally occurring CueO (wild-type CueO) or CueO modified from wild-type CueO as long as it sustains the performance of wild-type CueO.

It is not particularly limited that the CueO is derived from which organism, but CueO derived from *Escherichia coli* is preferable.

The CueO may either be immature CueO including a signal sequence or a mature CueO not including a signal sequence.

In the invention, helix 5 in CueO refers to α-helix formed from an amino acid sequence of from Pro at $357^{th}$ position to Gly at $372^{nd}$ position in SEQ ID NO: 1.

SEQ ID NO: 1 represents an amino acid sequence for an immature type of wild-type CueO derived from *Escherichia coli*. An amino acid sequence of from $1^{st}$ to $28^{th}$ positions is a signal sequence which is cleaved when CueO is transferred into periplasm.

An amino acid sequence represented by SEQ ID NO: 2 is a sequence obtained by removing the signal sequence of from $1^{st}$ to $28^{th}$ positions from the amino acid sequence represented by SEQ ID NO: 1, and is an amino acid sequence representing a mature type of wild-type CueO derived from *Escherichia coli*.

Thus, helix 5 in CueO for SEQ ID NO: 2 is formed with an amino acid sequence of from Pro at $329^{th}$ position to Gly at $344^{th}$ position.

In the invention, helix 6 for CueO refers to α-helix formed with an amino acid sequence of from Asp at $373^{rd}$ position to Ala at $377^{th}$ position in SEQ ID NO: 1 (that is, an amino acid sequence of from Asp at $345^{th}$ position to Ala at $349^{th}$ position in SEQ ID NO: 2).

In the invention, helix 7 for CueO refers to α-helix formed with an amino acid sequence of from Asp at $403^{rd}$ position to His at $406^{th}$ position in SEQ ID NO: 1 (that is, an amino acid sequence of from Asp at $375^{th}$ position to His at $378^{th}$ position in SEQ ID NO: 2).

The helix 5, the helix 6, and the helix 7 for CueO cover the top part of Type I copper included in CueO, as shown in FIG. 1. When CueO is oxidizing a substrate, it is thought to go thorough a process of transferring an electron from the substrate to Type I copper when the substrate comes close to the Type I copper. According to the invention, when any of helix 5, helix 6, and helix 7 covering the top part of Type I copper is removed, a substrate can more easily come close to the Type I copper, and thus thought to improve the enzymatic activity for oxidizing the substrate.

The helix 6 and the helix 7 are originally bonded via a structure unknown sequence, but they are shown as disconnected in FIG. 1 as the structure between them is not clear.

For the invention, removal of helix 5 may include a complete removal of an amino acid sequence constituting the helix 5 (a sequence of from Pro at $357^{th}$ position to Gly at $372^{nd}$ position in SEQ ID NO: 1, that is, a sequence of from Pro at $329^{th}$ position to Gly at $344^{th}$ position in SEQ ID NO: 2), or may also include a partial removal of the amino acid sequence. In the latter case, there are no particular limitations as long as the removal leads the substrate to easily come close to Type I copper, and elimination of a complete or a part of the helix structure of helix 5 according to such removal. In specific, a case where an amino acid sequence of from Met at $358^{th}$ position to Gly at $372^{nd}$ position in SEQ ID NO: 1 (that is, an amino acid sequence of from Met at $330^{th}$ position to Gly at $344^{th}$ position in SEQ ID NO: 2) is removed, a case where almost half of the amino acid sequence constituting the helix 5 is removed to reduce the helix structure of helix 5, or the like, can be mentioned.

For the invention, removal of helix 6 may also include a complete removal of an amino acid sequence constituting the helix 6 (a sequence of from Asp at $373^{rd}$ position to Ala at $377^{th}$ position in SEQ ID NO: 1, that is, a sequence of from Asp at $345^{th}$ position to Ala at $349^{th}$ position in SEQ ID NO:

2), or may also include a partial removal of the amino acid sequence as long as it leads the substrate to easily come close to Type I copper.

For the invention, removal of helix 7 may include a complete removal of an amino acid sequence constituting the helix 7 (a sequence of from Asp at $403^{rd}$ position to His at $406^{th}$ position in SEQ ID NO: 1, that is, a sequence of from Asp at $375^{th}$ position to His at $378^{th}$ position in SEQ ID NO: 2), or may also include a partial removal of the amino acid sequence as long as it leads the substrate to easily come close to Type I copper.

The recombinant protein of the invention is a protein obtained by removing from CueO at least one member selected from the group consisting of helix 5, helix 6, and helix 7. In specific, the recombinant protein may be any of a protein obtained by removing any one of helices 5, 6, and 7, a protein obtained by removing helices 5 and 6, a protein obtained by removing helices 5 and 7, a protein obtained by removing helices 6 and 7, and a protein obtained by removing helices 5, 6, and 7. From the viewpoint of oxidative polymerizability, preferably helix 5 is at least removed, and more preferably helix 5, helix 6, and helix 7 are removed.

A preferred embodiment of the recombinant protein of the invention is a protein obtained by removing helix 5, helix 6, and helix 7, from CueO, and instead inserting a spacer thereinto.

In the case of removing helices 6 and 7 or helices 5, 6, and 7, it is more preferable that the structure unknown sequence existing between the helix 6 and the helix 7 (from Gly at $378^{th}$ position to Phe at $402^{nd}$ position in SEQ ID NO: 1) be removed.

According to the invention, the recombinant protein obtained by removing at least one member selected from the group consisting of helix 5, helix 6, and helix 7 does not include the amino acid sequence as described above, but may be formed as a peptide chain by connecting the upstream peptide chain with the downstream peptide chain. The upstream peptide chain can be connected directly with the downstream peptide chain, but they are preferably connected via a spacer to maintain the conformation of CueO. The spacer will be described later.

According to the invention, the term 'enzymatic activity for oxidizing p-phenylenediamine' refers to a property of oxidizing p-phenylenediamine under the conditions shown in Test Example 1 of the present specification. That is, the term 'having an enzymatic activity for oxidizing p-phenylenediamine' means that when a target enzyme is mixed with p-phenylenediamine in an aqueous solution of pH 5.5 at a normal temperature (23° C.) in a ratio of 0.0005 moles relative to 1 mole of p-phenylenediamine, and allowed to react for 30 seconds, the absorbance measured at 470 nm shows a change.

The preferred recombinant protein according to the invention is excellent in point of an enzymatic activity for oxidizing p-phenylenediamine as compared to that of wild-type CueO derived from *Escherichia coli* (SEQ ID NO: 2).

The recombinant protein of the invention preferably has at least one or all of an enzymatic activity for oxidizing p-aminophenol, an enzymatic activity for oxidizing o-aminophenol, an enzymatic activity for oxidizing syringaldazine, an enzymatic activity for oxidizing bilirubin, and an enzymatic activity for oxidizing 2,2'-azino-bis(3-ethylbenzothiazoline-6-sulfonate) (ABTS). Each of the enzymatic activities can be measured in accordance with the condition shown in Test Example 1 of the present specification and the condition shown above in relation to p-phenylenediamine.

The preferred recombinant protein of the invention is excellent in point of all of enzymatic activities mentioned above as compared to that of wild-type CueO derived from *Escherichia coli* (SEQ ID NO: 2).

The spacer in the present specification is an amino acid residue or sequence inserted in the recombinant protein of the invention obtained by removing at least one member selected from the group consisting of helix 5, helix 6, and helix 7, in place of the removed sequence so as to more preferably maintain the conformation of CueO.

The amino acid residue or sequence constituting the spacer is not particularly limited as long as the recombinant protein exhibits the above-mentioned enzymatic activities, but is preferably a single amino acid residue or a sequence obtained from 2 to 15 amino acid residues. Of these, preferred are a single amino acid residue, and sequences obtained from 2 to 10 amino acid residues.

In specific, for the embodiment in which helix 5, helix 6, and helix 7 are removed, in order to maintain a β-sheet structure adjacent to the helices 5 to 7, a spacer of a single amino acid residue is preferably Gly or Pro, and a spacer of two amino acid residues is preferably Gly-Gly or Ala-Ala. In particular, Gly-Gly is preferable in point of providing a flexible property. A spacer of nine amino acid residues is preferably Ala-Ala-Gly-Ala-Ala-Gly-Ala-Ala-Ala (SEQ ID NO: 42). A spacer of ten amino acid residues is preferably Ala-Ala-Gly-Ala-Ala-Gly-Ala-Ala-Gly (SEQ ID NO: 43).

A specific example of the recombinant protein of the invention includes a protein obtained by removing an amino acid sequence represented by SEQ ID NO: 13 (an amino acid sequence of from Pro at $357^{th}$ position to His at $406^{th}$ position in SEQ ID NO: 1, that is, an amino acid sequence of from Pro at $329^{th}$ position to His at $378^{th}$ position in SEQ ID NO: 2) in wild-type CueO and then inserting a spacer thereinto.

In this specific example, when Gly-Gly is used as the spacer, the amino acid sequence thereof can be represented by SEQ ID NO: 3 or SEQ ID NO: 4. The amino acid sequence represented by SEQ ID NO: 3 is for an immature type containing a signal sequence of from $1^{st}$ to $28^{th}$ positions. The amino acid sequence represented by SEQ ID NO: 4 is for a mature type not containing a signal sequence of from $1^{st}$ to $28^{th}$ positions. In addition, when Ala-Ala is used as the spacer, the amino acid sequence thereof can be represented by SEQ ID NO: 36. This amino acid sequence is for a mature type not containing a signal sequence.

In addition, specific examples of the recombinant protein of the invention include: a protein obtained by removing helix 6 and helix 7 in wild-type CueO and instead inserting a spacer thereinto (more specifically, those in which the amino acid sequence is represented by SEQ ID NO: 37, which is a mature type); a protein obtained by removing helix 5 in wild-type CueO and instead inserting a spacer thereinto (more specifically, those in which the amino acid sequence is represented by SEQ ID NO: 38, which is a mature type); a protein obtained by removing helix 6 and helix 7, as well as almost half of the amino acid sequence constituting the helix 5, in wild-type CueO, and instead inserting a spacer thereinto (more specifically, those in which the amino acid sequence is represented by SEQ ID NO: 39, which is a mature type); and the like.

A most preferred embodiment of the recombinant protein of the invention is a protein including an amino acid sequence represented by SEQ ID NO: 4, SEQ ID NO: 36, SEQ ID NO: 37, SEQ ID NO: 38, or SEQ ID NO: 39. For this embodiment, in addition to the amino acid sequence represented by above-mentioned SEQ ID NO, an amino acid sequence added with a sequence giving no effect on the enzymatic activity such as a histidine tag to C-terminus or N-terminus of the amino acid sequence represented by the above-mentioned SEQ ID NO is also included. The amino acid sequence which is obtained by adding histidine to C-terminus of the amino acid sequence represented by SEQ ID NO: 4 is represented by SEQ ID NO: 5.

For the recombinant protein of the invention, there may also include a protein which contains an amino acid sequence obtained by deletion, substitution, and/or addition of one or more amino acid(s) in the amino acid sequence described in the present specification, and has an enzymatic activity for oxidizing p-phenylenediamine.

The substitution, deletion, and/or addition in the amino acid sequence can be carried out by a site-directed mutagenesis method which is a well-known technique, for example, can be carried out according to a method described in Proc. Natl. Acad. Sci. USA, 81, 4662-5666, 1984; Nucleic Acid Res. 10, 6487-6500, 1982; WO 85/00817; Nature 316, 601-605, 1985, or the like.

The term 'deletion, substitution, and/or addition of one or more amino acid(s)' means that deletion, substitution, and/or addition of number of amino acids that can be subjected to substitution, deletion, and/or addition according to a well-known method such as a site-directed mutagenesis method, take(s) place in the amino acid sequence described in the present specification.

For example, at least one, preferably 1 to about 10, more preferably 1 to 5 amino acid(s) in the amino acid sequence described in the present specification may be deleted; at least one, preferably 1 to about 10, more preferably 1 to 5 amino acid(s) may be added to the amino acid sequence described in the present specification; or at least one, preferably 1 to about 10, more preferably 1 to 5 amino acid(s) in the amino acid sequence described in the present specification may be replaced with other amino acids.

It can be simply confirmed that such amino acid sequence has an enzymatic activity for oxidizing p-phenylenediamine according to the above-mentioned method.

As above, it is preferable that the protein of the invention have at least one or all of an enzymatic activity for oxidizing p-aminophenol, an enzymatic activity for oxidizing o-aminophenol, an enzymatic activity for oxidizing syringaldazine, an enzymatic activity for oxidizing bilirubin, and an enzymatic activity for oxidizing 2,2'-azino-bis(3-ethylbenzothiazoline-6-sulfonate) (ABTS). Confirming these enzymatic activities can also be done simply by the method described above.

The recombinant protein of the invention can be simply produced by the method employing a transformant described later.

Next, the gene, the recombinant vector, and the transformant, of the invention will be described.

The gene of the invention encodes the recombinant protein of the invention described above.

The base sequence of the gene is not particularly limited as along as it codes for the recombinant protein of the invention described above. In specific, a base sequence represented by SEQ ID NO: 6, 7, 14, 20, 26, 32, or 40 can be exemplified.

The gene of the invention also includes a gene composed of a DNA hybridizing with a DNA composed of a base sequence which is complementary to the DNA composed of the base sequence described in the present specification under stringent conditions, and encoding a protein having an enzymatic activity for oxidizing p-phenylenediamine. In the invention, the stringent condition, for example, is a condition under a sodium concentration of 600 to 900 mM and a temperature of 60 to 68° C., preferably 65° C.

The process for producing the gene of the invention will be described.

The gene of the invention can be produced, for example, by a PCR method using wild-type CueO gene as a template. In specific, a base sequence of upstream (hereinafter, referred to as 'upstream sequence') and a base sequence of downstream (hereinafter, referred to as 'downstream sequence') from the base sequence to be removed from the base sequence coding for wild-type CueO are amplified, respectively, with the use of suitable primers. On this occasion, a base sequence coding for the spacer mentioned above and/or a complimentary sequence thereof can be inserted in the primer, which then allows 3' end of upstream sequence and/or 5' end of downstream sequence to include the base sequence coding for the spacer mentioned above and/or the complimentary sequence thereof.

The PCR condition is not particularly defined and well-known condition can be employed. For example, the condition can be exemplified by 25 cycles of denaturalization at 94° C. for 30 seconds, annealing at 55° C. for 1 minute, and extension at 72° C. for 1 minute.

Next, thus obtained 3' end of upstream sequence and 5' end of downstream sequence are linked to produce the gene of the invention encoding the target recombinant protein. The reaction condition for the linking is not particularly defined. For example, the reaction for linking can be carried out under a condition of denaturalization at 94° C. for 5 minutes and slow cooling to 40° C. at a rate of −2° C./minute.

Thereafter, the PCR technique may be repeated with the use of suitable primers so as to amplify the gene of the invention. The PCR condition for the second time is also not particularly defined and well-known condition can be employed. For example, the condition can be exemplified by 25 cycles of denaturalization at 94° C. for 30 seconds, annealing at 55° C. for 1 minute, and extension at 72° C. for 1 minute.

The recombinant vector of the invention contains the gene of the invention described above.

There is no particular limitation for the vector for a use in the invention, but examples of a plasmid derived from *Escherichia coli* include pBR322, pBR325, pUC19, pUC18, pUC119, and the like. Preferred is pUC18.

There is no particular limitation on the condition for producing the recombinant vector of the invention, and a well-known method can be employed. In specific, the recombinant vector can be produced according to an overnight reaction at 16° C. with the use of Takara Ligation Kit Ver. 2.1 (manufactured by Takara Bio Inc.).

The transformant of the invention contains the recombinant vector of the invention described above.

There is no particular limitation for a host for a use in producing the transformant of the invention, but examples thereof include a microorganism, an animal cell, a plant cell, and the like. Preferred is a microorganism, and more preferred is *Escherichia coli*. *Escherichia coli* to be used is not particularly limited, but examples thereof include XL1-Blue, BL21, JM109, NM522, DH5α, HB101, DH5, and the like.

There is no particular limitation for the production method of the transformant of the invention, and the production can be carried out according to a well-known method such as electroporation.

The production method of the recombinant protein of the invention can be carried out by culturing the transformant of the invention described above according to a usual method, and collecting the produced recombinant protein.

Upon culturing, when the host is *Escherichia coli*, LB medium, M9 medium, or the like can be used as the medium. To the medium, an agent such as isopropylthio-β-D-galactoside (IPTG) or ampicillin can be added. The culturing, for example, can be carried out for about 1 to 24 hours at a temperature between 30 and 37° C., if necessary, under aeration or stirring.

There is no particular limitation to a collection of a recombinant protein from the medium after culturing the transformant, but can be carried out by breaking cells according to an osmotic shock technique or the like to give a crude enzyme solution and then subjecting purification. For the purification technique, a well-known method such as salting out, solvent precipitation, dialysis, ultrafiltration process, polyacrylamide gel electrophoresis, ion-exchange chromatography, affinity chromatography, reversed-phase high-performance liquid chromatography, isoelectric focusing, or the like can be employed.

Next, the composition for dyeing keratin fiber of the invention will be described.

The composition for dyeing keratin fiber of the invention contains the recombinant protein and an oxidation dye. In the case of employing a recombinant protein produced by a cell body of the transformant or the like, other than a pure protein which had been purified, a crude product containing a recombinant protein can also be used.

The blending ratio of the recombinant protein in the composition for dyeing keratin fiber of the invention can be variously adjusted in accordance with the type of keratin fiber to be used, conditions upon dyeing, kind of an oxidation dye, and the like, thus is not particularly limited. Preferably, the blending ratio is in the range of from 0.001 to 10 parts by weight, and more preferably from 0.01 to 1 part(s) by weight, relative to a total amount of 100 parts by weight of the composition.

The composition for dyeing keratin fiber of the invention contains an oxidation dye. The oxidation dye achieves dyeing by color development via an oxidation reaction and a polymerization reaction. The oxidation dye includes 'dye precursor' for developing color by undergoing oxidative polymerization, and 'coupler' for giving various color tones by undergoing polymerization with the dye precursor.

The dye precursor includes o- or p-phenylenediamine, aminophenol, and the like, and the coupler includes m-phenylenediamine, aminophenol, and the like.

There is no particular limitation for the dye precursor, but specific examples thereof may include p-phenylenediamine, 5-amino-ortho-cresol, o-aminophenol, m-aminophenol, p-aminophenol, 2,6-diaminopyridine, 5-(2-hydroxyethylamino)-2-methylphenol, N,N-bis(β-hydroxy)-p-phenylenediamine sulfate, p-nitro-o-phenylenediamine, p-nitro-2',4'-diaminoazobenzene sodium sulfate, toluene-2,5-diamine, 5-amino-o-cresol sulfate, p-aminophenol sulfate, o-chloro-p-phenylenediamine sulfate, 4,4'-diaminodiphenylamine-sulfate, p-methylaminophenol sulfate, p-phenylenediamine sulfate, m-phenylenediamine sulfate, toluene-2,5-diamine sulfate, 2,4-diaminophenoxyethanol hydrochloride, toluene-2,5-diamine hydrochloride, m-phenylenediamine hydrochloride, 2,4-diaminophenol hydrochloride, 3,3'-iminodiphenol, p-phenylenediamine hydrochloride, N-phenyl-p-phenylenediamine hydrochloride, N-phenyl-p-phenylenediamine acetate, 1,5-dihydroxynaphthalene, tolylene-3,4-diamine, p-methylaminophenol, N,N'-bis(4-aminophenyl)-2,5-diamino-1,4-quinonediimine, o-aminophenol sulfate, 2,4-diaminophenol sulfate, m-aminophenol sulfate, and the like. Compounds exemplified above are those published in Japanese Standards of Quasi-drug Ingredients (JSQI).

For the invention, an indoline compound or an indole compound can be used as the oxidation dye.

There is no particular limitation for the indoline compound, but examples thereof include indoline, 5,6-dihydroxyindoline, N-methyl-5,6-dihydroxyindoline, N-ethyl-5,6-dihydroxyindoline, N-butyl-5,6-dihydroxyindoline, 4-hydroxy-5-methoxyindoline, 6-hydroxy-7-methoxyindoline, 6,7-dihydroxyindoline, 4,5-dihydroxyindoline, 4-methoxy-6-hydroxyindoline, N-hexyl-5,6-dihydroxyindoline, 2-methyl-5,6-dihydroxyindoline, 3-methyl-5,6-dihydroxyindoline, 4-hydroxyindoline, 2,3-dimethyl-5,6-dihydroxyindoline, 2-methyl-5-ethyl-6-hydroxyindoline, 2-methyl-5-hydroxy-6-β-hydroxyethylindoline, 4-hydroxypropylindoline, 2-hydroxy-3-methoxyindoline, 6-hydroxy-5-methoxyindoline, 6-hydroxyindoline, 5-hydroxyindoline, 7-hydroxyindoline, 7-aminoindoline, 5-aminoindoline, 4-aminoindoline, 5,6-dihydroxyindolinecarboxylic acid, 1-methyl-5,6-dihydroxyindoline, salts thereof, and the like.

There is no particular limitation for the indole compound, but examples thereof include 4,5-dihydroxyindole, 5,6-dihydroxyindole, 6,7-dihydroxyindole, N-methyl-5,6-dihydroxyindole, N-ethyl-5,6-dihydroxyindole, N-hexyl-5,6-dihydroxyindole, 2-methyl-5,6-dihydroxyindole, 3-methyl-5,6-dihydroxyindole, 4-hydroxyindole, 2,3-dimethyl-5,6-dihydroxyindole, 2-methyl-5-ethyl-6-hydroxyindole, 2-methyl-5-hydroxy-6-β-hydroxyethylindole, 4-hydroxypropylindole, 2-hydroxy-3-methoxyindole, 4-hydroxy-5-methoxyindole, 6-hydroxy-7-methoxyindole, 6-hydroxy-5-methoxyindole, 6-hydroxyindole, 5-hydroxyindole, 7-hydroxyindole, 7-aminoindole, 5-aminoindole, 4-aminoindole, 5,6-dihydroxyindolecarboxylic acid, 1-methyl-5,6-dihydroxyindole, salts thereof, and the like.

The oxidation dye for a use in the invention is preferably p-phenylenediamine, p-aminophenol, o-aminophenol, 2,4-diaminophenol, toluene-2,5-diamine, and salts thereof, from the viewpoint of substrate specificity of the recombinant protein of the invention.

These oxidation dyes may either be used alone or in combination of plural kinds. Preferably, one or plural kinds of compounds belonging to the dye precursor is/are used, or a combination of one or plural kinds of compounds belonging to the dye precursor and one or plural kinds of compounds belonging to the coupler is used.

The blending amount of the oxidation dye in the composition for dyeing keratin fiber of the invention is not particularly limited, and suitably adjusted to exhibit preferable dyeing ability. For example, the blending amount is in the range of 0.01 to 20 weight %, preferably 0.1 to 10 weight %, relative to a total amount of the composition.

In addition to the oxidation dye, a direct dye can also be blended in the composition for dyeing keratin fiber of the invention so as to adjust the color tone to be obtained.

There is no particular limitation for the direct dye, and examples thereof include 2-amino-4-nitrophenol, 2-amino-5-nitrophenol, 1-amino-4-methylaminoanthraquinone, nitro-p-phenylenediamine hydrochloride, 1,4-diaminoanthraquinone, nitro-p-phenylenediamine, picramic acid, sodium picramate, 2-amino-5-nitrophenol sulfate, resorcinol, nitro-p-phenylenediamine sulfate, p-nitro-o-phenylenediamine sulfate, p-nitro-m-phenylenediamine sulfate, Natural Orange 6 (2-hydroxy-1,4-naphthoquinone), Acid Orange 8, Acid Violet 17, Remasol brilliant blue, Evans blue, Acid Blue 80, and the like.

The blending amount of the direct dye in the composition for dyeing keratin fiber of the invention is not particularly limited, and variously adjusted in accordance with the desired color tone. For example, the blending amount is in the range of 0.0 to 20 weight % relative to a total amount of the composition.

The composition for dyeing keratin fiber of the invention preferably further contains an alkaline compound. The recombinant protein of the invention exhibits enzymatic performance under a weak acid or alkaline condition, and since it has an optimum pH in an alkaline region, from the viewpoint of dyeing ability, it is preferable to make the composition of the invention alkaline by blending an alkaline compound. By making the composition alkaline, dyeing effect can be improved as keratin fiber swells, thereby allows dye to penetrate into hair cortex and to deposit therein.

There is no particular limitation for the alkaline compound to be blended in the composition for dyeing keratin fiber of the invention, and generally those capable of being blended in the dyeing agent can be used. Examples of the alkaline compound include amine compounds such as monoethanolamine, monoisopropanolamine, triethanolamine, and diethanolamine, inorganic compounds such as ammonia, sodium hydroxide, potassium hydroxide, and ammonium carbonate, and the like.

The blending amount of the alkaline compound in the composition for dyeing keratin fiber of the invention is not particularly limited, and a suitable amount to give a desired pH (preferably pH of 7.5 to 10.5) can be blended. For example, the blending amount is in the range of 0.0 to 20 weight % relative to a total amount of the composition.

To the composition for dyeing keratin fiber of the invention, various components can also be blended in addition to the components described above. There is no particular limitation, but specific examples of the component include a reducing agent such as thiolactic acid, sodium sulfite, and N-acetyl-L-cysteine, a surfactant, an oily component, silicones, a viscosity improver, a solvent, water, a chelating agent, flavor, and the like.

The composition for dyeing keratin fiber of the invention is preferably an aqueous solution.

The composition of the invention is for dyeing keratin fiber. The keratin fiber include other various fibers, in addition to hair of mammals such as humans. There is no particular limitation for the fiber, and it may be any of natural and synthetic fibers. Examples thereof include cotton, diacetate, flax, linen, lyocell, polyacryl, polyamide, polyester, ramie, rayon, Tencel, triacetate, fur, fell, leather, silk, wool, and the like. In addition, there is no particular limitation on a form of the fiber, and it may be in any form of fabric, yarn, clothing material, film, and the like.

The composition for dyeing keratin fiber of the invention can be prepared into a one-part type composition by mixing the above-mentioned components in an oxygen-free atmosphere and charging the mixture into a container in an oxygen-free atmosphere.

Further, the composition for dyeing keratin fiber of the invention can be prepared into a two-part type composition comprising a first composition containing the recombinant protein and the second composition containing an oxidation dye. In this case, mixing of the components and preservation may not have to be done in an oxygen-free atmosphere.

When the composition for dyeing keratin fiber of the invention is a one-part type composition, it is directly applied to keratin fiber, and when the composition is a two-part type composition, two compositions are mixed and subsequently applied to keratin fiber. In this manner, keratin fiber can be simply and efficiently dyed.

The method of dyeing keratin fiber of the invention includes bringing keratin fiber into contact with an oxidation dye in the presence of the recombinant protein under an oxygen-containing atmosphere. There is no particular limitation for the oxygen-containing atmosphere, but usually is air. The temperature upon bringing contact is not particularly limited, but is preferably between 10 and 100° C. When applying to hair, the temperature is preferable to be between 20 and 40° C. from the viewpoint of effect that may be caused on the human body.

The recombinant protein of the invention exhibits sufficient oxidative polymerization activity under a weak acid and alkaline condition. Thus the above-mentioned contacting treatment is preferably carried out under a weak acid or alkaline condition (e.g., pH 6 to 11). However, since the recombinant protein of the invention has an optimum pH in an alkaline region, the contacting treatment is more preferably carried out under an alkaline condition (preferably, pH 7.5 to 10.5). Details of the dyeing method of the invention are same as those described for the composition of the invention.

ADVANTAGE OF THE INVENTION

The invention has above-mentioned constitutions, and thus modified CueO excellent in enzymatic activity for oxidizing p-phenylenediamine or the like as compared to wild-type CueO can be provided.

Further, a composition for dyeing keratin fiber in which the oxidation polymerization of an oxidation dye proceeds efficiently by employing an enzyme in place of an oxidizing agent such as hydrogen peroxide and which is capable of being prepared into a one-part agent, where the composition is capable of efficiently dyeing keratin fiber in a wide range of pH region including an alkaline condition, as well as is stable at a wide range of temperature and pH without impairing the toning ability of the direct dye; and a method of dyeing keratin fiber by employing the above-mentioned enzyme, can be provided.

BEST MODE FOR CARRYING OUT THE INVENTION

Reference Production Example 1

Preparation of Expression Vector Containing Wild-Type CueO Gene

An expression vector in which a base sequence obtained by adding a base sequence coding for a histidine tag to a base sequence of wild-type immature CueO gene is introduced, was prepared in the following order, such that a modified CueO gene is used as a template when cloning.

A wild-type immature CueO gene was amplified by a PCR technique with the use of genomic DNA extracted from *E. coli* JM109 as the template. For the amplification, a PCR reaction was carried out using synthetic oligonucleotide primers and a PCR reaction solution both shown below, with the reaction cycle also shown below.

```
N-EcoRI:
                                      (SEQ ID NO: 9)
5'-gaagaattcatgcaacgtcgtgatttcttaaaat-3'
(gaattc at positions 4 to 9 is EcoRI
recognition site)

3'-His-Bam:
                                      (SEQ ID NO: 10)
5'-ttggatccttaatgatgatgatgatgatggcctaccgtaaaccct
aac-3'
(ggatcc at positions 3 to 8 is BamHI
recognition site,
and atgatgatgatgatgatg at positions 12 to 29 is a
sequence coding for a histidine tag)
```

PCR Reaction Solution

| | |
|---|---|
| E. coli genomic DNA (0.5 µg/µL) | 1 µL |
| Primers (10 pmol/µL) | 1 µL of each |
| PCR buffer solution (×10) | 5 µL |
| dNTP mix. (2.5 mM) | 4 µL |
| dimethylsulfoxide | 2.5 µL |
| Purified water | 35.25 µL |
| Takara EX Taq | 0.25 µL |

Reaction Cycle
 (1) Preheat: 95° C., 2 mins
 (2) Denaturalization: 95° C., 1 min
 (3) Annealing: 50° C., 1 min
 (4) Extension: 72° C., 1 min→returns to (2) (25 cycles)
 (5) Extension: 72° C., 10 mins After the above PCR reaction, the amplified product was concentrated by ethanol precipitation described below.

Ethanol Precipitation

To 50 µL of a sample, 5 µL of 3M sodium acetate and 100 µL of 100% ethanol were added, and the mixture was left still at −80° C. for 10 minutes. Thereafter, centrifugation was carried out at 14,000 rpm for 5 minutes, and the supernatant was discarded. To the pellet, 500 µL of 70% ethanol was added for washing, and then centrifugation was again carried out at 14,000 rpm for 5 minutes. The supernatant was discarded. The remaining pellet was dried under reduced pressure for about 5 minutes, and dissolved in 30 µL of a reaction solution for restriction enzyme digestion.

1. Restriction Enzyme Digestion

The restriction enzyme treatment of an amplified fragment and a pUC18 vector was carried out in the following reaction system:

Reaction Solution (for Treatment of CueO Amplified Fragment)

| | |
|---|---|
| CueO amplified fragment | about 20 µg |
| TOYOBO H buffer solution | 3.0 µL |
| EcoRI (manufactured by TOYOBO) | 0.3 µL |
| BamHI (manufactured by TOYOBO) | 0.3 µL |
| Purified water | 26.4 µL |
| Total | 30.0 µL |

Reaction System (for Treatment of pUC18)

| | |
|---|---|
| pUC18 | about 20 µg |
| TOYOBO H buffer solution | 3.0 µL |
| EcoRI (manufactured by TOYOBO) | 0.3 µL |
| BamHI (manufactured by TOYOBO) | 0.3 µL |
| alkaline phosphatase | 1.0 µL |
| Purified water | 25.4 µL |
| Total | 30.0 µL |

After preparing each solution, it was left overnight at 37° C. for digestion, respectively.

2. Agarose Gel Electrophoresis

6 µL of dye was added for every 30 µL of the sample solution, and the resultant was loaded on a 1% agarose gel (1×TAE buffer solution). Electrophoresis was run at 100 V for 1 hour, and then DNA bands were stained using an ethidium bromide solution. Under confirming with the UV illuminator, the target fragment of 1.5 kbp and pUC18 of 2.7 kbp were cut.

3. DNA Fragment Extraction

The DNA fragment and pUC18 were extracted from the agarose gel according to a protocol of QIAEX II (manufactured by QUIAGEN). For the elution, 10 µL of a TE buffer solution was used, respectively.

4. Ligation

The EcoRI-BamHI digested fragment of CueO gene and the digested fragment of pUC18 were linked in the reaction solution shown below according to a protocol of Takara DNA Ligation Kit Ver. 2.1 (manufactured by Takara Bio Inc.).

Reaction Solution

| | |
|---|---|
| CueO gene gel extraction fragment | 4.5 µL |
| pUC18 gel extraction fragment | 0.5 µL |
| Ligation Kit Ver 2.1, Sol. I | 5.0 µL |
| Total | 10.0 µL |

After preparing the solution, it was left overnight at 16° C. for a reaction to take place using Thermal Cycler.

5. Butanol Concentration

To 10 µL of the ligation solution, 200 µL of butanol was added, and the mixture was stirred. Thereafter, centrifugation was carried out at 14,000 rpm for 5 minutes, and the supernatant was discarded. To the pellet, 400 µL of diethylether was added, and then centrifugation was again carried out at 14,000 rpm for 5 minutes. The supernatant was discarded. The remaining pellet was naturally dried for about 10 minutes, and then dissolved in 10 µL of sterile water. Thus obtained expression vector was given as pUC-CueO.

Example 1

Production of Modified CueO (1):CueO (Δα5-7) Gene of Invention

The modified CueO (1) gene of the invention obtained by introducing mutation into the wild-type CueO gene was produced by the following procedures.

An amino acid sequence of the target modified CueO (1) (SEQ ID NO: 5) is an amino acid sequence obtained by removing sequences constituting helices 5, 6, and 7, and an amino acid sequence of the structure unknown sequence existing between the helix 6 and the helix 7 (from Pro at $329^{th}$ position to His at $378^{th}$ position in SEQ ID NO: 2, shown by SEQ ID NO: 13) and instead inserting two residues of Gly-Gly as the spacer, and adding a histidine tag to C-terminus.

The upstream fragment (N-terminus side) and the downstream fragment (C-terminus side) of the mutation-inserted site were amplified by a PCR technique with the use of the wild-type CueO expression vector pUC-CueO obtained in Reference Production Example 1 as the template, (first PCR). For the upstream fragment amplification, the above-mentioned N-EcoRI and a synthetic oligonucleotide primer shown below were used.

```
                                    (SEQ ID NO: 11)
HdeLGG-Fw:
5'-gttggcaccaccgtccatggaagattgcagcttgcgtac-3'
(accacc at positions 7 to 12 corresponds to
two residues of Gly-Gly)
```

For the downstream fragment amplification, the above-mentioned 3'-His-Bam and a synthetic oligonucleotide primer shown below were used.

HdelGG-Rv:
(SEQ ID NO: 12)
5'-ctctccatggacggtggtgccaacaaaatcaacggtc-3'
(ggtggt at positions 13 to 18 corresponds to
two residues of Gly-Gly)

For the reaction, a PCR reaction solution shown below was used.

First PCR Reaction Solution

| | |
|---|---|
| Expression vector pUC-CueO (30 ng/μL) | 1 μL |
| Primers (10 pmol/μL) | 1 μL of each |
| PCR buffer solution (×10) | 5 μL |
| dNTP mix. (2.5 mM) | 4 μL |
| dimethylsulfoxide | 2.5 μL |
| Purified water | 35.25 μL |
| Takara EX Taq | 0.25 μL |

Reaction Cycle
(1) Preheat: 94° C., 3 mins
(2) Denaturalization: 94° C., 30 sec
(3) Annealing: 50° C., 1 min
(4) Extension: 72° C., 1 min→returns to (2) (25 cycles)
(5) Extension: 72° C., 7 mins After the above PCR reaction, the amplified product was concentrated by ethanol precipitation as described above, and then separated by agarose gel electrophoresis as described above. As above, the target bands (upstream PCR fragment (1.1 kbp), downstream PCR fragment (0.4 kbp)) were extracted and purified by QIAEXII.

1. Annealing

Using the reaction solution and reaction program shown below, the DNA fragment extracted and purified from gel was subjected to annealing.

Reaction Solution

| | |
|---|---|
| Upstream PCR fragment (1.1 kbp) | 1.0 μL |
| Downstream PCR fragment (0.4 kbp) | 1.0 μL |
| dNTP mix. (2.5 mM) | 10 μL |
| PCR buffer solution (×10) | 10 μL |
| Purified water | 75.5 μL |

Reaction Program
(1) Denaturalization: 94° C., 5 mins
(2) Cooling to 40° C. (−2° C./min) for annealing
(3) keeping at 40° C.

2. Template Strand Synthesis

To the annealing reaction solution, 0.5 μL of TOYOBO Blend Taq DNA polymerase was added, and a template strand was synthesized under the reaction program below.

Reaction Cycle
(1) 60° C., 1 min
(2) Extension: 72° C., 2 mins
(3) Denaturalization: 94° C., 30 sec
(4) cooling to 50° C. (−15° C./min) for annealing
(5) Annealing: 50° C., 1 min
(6) Extension: 72° C., 1 min→returns to (3) (5 cycles)

3. Amplification of Whole Region of Modified CueO (1) Gene

To the template strand synthesis reaction solution, 10 pmol/μL of N-EcoRI and 1 μL of 3'His-Bam primers were added, and the PCR reaction was carried out according to the reaction cycle shown below.

Reaction Cycle
(1) Preheat: 94° C., 3 mins
(2) Denaturalization: 94° C., 30 sec
(3) Annealing: 55° C., 1 min
(4) Extension: 72° C., 1 min→returns to (2) (25 cycles)
(5) Extension: 72° C., 7 mins After the above PCR reaction, the amplified product was concentrated by ethanol precipitation described below.

In the above manner, the modified CueO (1) gene (DNA fragment of 1.4 Kbp) having a base sequence represented by SEQ ID NO: 40 was obtained.

Example 2

Production of Recombinant Vector of Invention

Thus obtained DNA fragment of 1.4 Kbp according to the above method was digested with EcoRI and BamHI, and ligated to plasmid vector pUC18 digested in the same manner. From the obtained recombinant vector, a base sequence represented by SEQ ID NO: 40 was confirmed. The obtained recombinant vector was given as pUC18-CueO(Δα5-7).
given as pUC18-CueO(Δα5-7).

Example 3

Production of Transformant of Invention

10 μL of the sample solution that had been subjected to butanol concentration according to the above procedure was added to 50 μL of E. coli BL21 (DE3) competent cell, and subjected to stirring. Then, whole amount was put in a cuvette (1 mm electrode gap). Electroporation was carried out using a Micro Pulser manufactured by Bio-Rad with Program EC1. E. coli was suspended in 1 mL of LB medium, recovered, and shaked at 37° C. for 1 hour. Thereafter, the cultured cell was plated on an LB agar medium containing ampicillin. The plate was left overnight at 37° C.

The competent cell was prepared in accordance with the Bio-Rad instruction.

The obtained transformant E. coli BL21 (DE3)/pUC18-CueO(Δα5-7) has been deposited in patent organism deposition center in National Institute of Advanced Industrial Science and Technology (zip code 305-8566, Tsukuba Central 6, 1-1-1, Tsukuba, Ibaraki), on 5 Oct. 2005, under the Budapest Treaty (Deposition No: FERM BP-10431).

Example 4

Production and Purification of Recombinant Protein of Invention (1) Culturing Transformant The transformant E. coli BL21 (DE3)/pUC-CueO(Δα5-7) was cultured by following two steps, and the recombinant protein of the invention was expressed.

1-1. Pre-Culture (Test Tube)

O/N aerobic culturing was subjected in 4 mL of LB medium containing 0.1 mg/mL ampicillin, at 37° C.

1-2. Main Culture (2 L Conical Flask with Baffle)

1 mM $CuCl_2$ and 0.5 mM IPTG were added to the above medium, and aerobic culturing was subjected at 32° C. for 12 hours.

Thereafter, cells were harvested by centrifugation, and washed with 0.85% aqueous sodium chloride solution, and then osmotic shock was performed straight after.

(2) Collection and Purification of Recombinant Protein 2-1. Osmotic Shock

The cells were suspended in a solution containing 20% sucrose, 100 mM Tris-HCl buffer solution (pH 7.5), and 10 mM EDTA, that is cooled with ice, and left still for 10 minutes in an ice bath. Thereafter, the cells were collected by centrifugation.

Next, the cells were suspended in ice-cold distilled water containing a protease inhibitor, and left still for 10 minutes in an ice bath. Thereafter, the supernatant was collected by centrifugation. This was a crude enzyme solution.

2-2. IMAC

The crude enzyme solution was overlaid on BD TALON column (40 mL) equilibrated with a 50 mM potassium phosphate buffer solution (pH 7.0), and then washed with the same buffer solution.

The adsorbed protein was eluted with the same buffer solution containing 150 mM imidazole. The elution fraction was concentrated, and dialyzed against 20 mM Tris-HCl buffer solution (pH 8.0).

2-3. Anion Exchange Chromatography

The sample was overlaid on BIO-RAD UnoQ-12 column (12 mL) equilibrated with a 20 mM Tris-HCl buffer solution (pH 8.0), and then washed with the same buffer solution (flow rate of 1 mL/min).

The adsorbed protein was eluted with a linear gradient from 0 to 1M potassium chloride solution (120 mL) using the same buffer solution. The active fraction was collected and concentrated.

The modified CueO (1) (amino acid sequence is represented by SEQ ID NO: 5, hereinafter, referred to as 'mCueO (1)') which is the recombinant protein of the invention purified in the above manner was used in Test Examples and Examples below.

Test Example 1

Evaluation on Oxidative Polymerization Activity of mCueO (1) for Representative Substrates of Laccase (1) Preparation of Substrate Solutions 2,6-dimethoxyphenol, p-phenylenediamine, 2,2'-azino-bis (3-ethylbenzothiazoline-6-sulfonate) (ABTS), 2-methoxyphenol, and catechol were dissolved in an ion-exchange distilled water, respectively, to each give a 50 mM aqueous solution.

4-hydroxyindole and p-aminophenol were dissolved in dimethylsulfoxide (DMSO), respectively, to each give a 50 mM DMSO solution.

o-aminophenol was dissolved in DMSO, and then dissolved in an ion-exchange distilled water, to give a 50 mM DMSO (10%)-aqueous solution.

1-nitroso-2-naphthol-3,6-disulfonic acid disodium (NNS) was dissolved in an ion-exchange distilled water to give a 5 mM aqueous solution.

Bilirubin was dissolved in DMSO to give a 0.5 mM DMSO solution.

Syringaldazine was dissolved in ethanol to give a 5 mM ethanol solution.

L-tyrosine was dissolved in a 0.1 M phosphate buffer solution (pH 6.5), to give a 1 mM solution.

(2) Activity Measurement Method

For the following method, an acetate buffer solution (pH 5.5) was used as the buffer solution.

For the substrates other than NNS and bilirubin, 0.88 mL of a 0.1 M buffer solution and 0.1 mL of the substrate solution were mixed in a cuvette (1.5 mL UV disposable cell, manufactured thereto, and mixed by inversion. The change in absorbance at each wavelength (measurement wavelength shown in Table 1) from 0 to 30 seconds was measured using a spectrophotometer (UV-2459, manufactured by SHIMADZU).

For NNS and bilirubin, 0.96 mL of a 0.1 M buffer solution and 0.02 mL of the substrate solution were mixed in a cuvette (1.5 mL UV disposable cell, manufactured by TOP), 0.02 mL of an aqueous solution of mCueO (1) was added thereto, and mixed by inversion. The change in absorbance at each wavelength (measurement wavelength shown in Table 1) from 0 to 30 seconds was measured using a spectrophotometer (UV-2459, manufactured by SHIMADZU).

A unit of the oxidative polymerization activity (U) shows an activity per 1 mg of mCueO (1), when given that the activity that changes absorbance by 1 in 1 minute is 1.

For comparison, the oxidative polymerization activity of an enzyme prepared by adding a histidine tag to the C-terminus of wild-type mature CueO (SEQ ID NO: 8, hereinafter, simply referred to as 'wild-type CueO') was measured in the same manner. A unit of the oxidative polymerization activity (U) shows an activity per 1 mg of wild-type CueO, when given that the activity that changes absorbance by 1 in 1 minute is 1. The change in absorbance in 30 seconds which is measured in the above manner was given in terms of change in absorbance in 1 minute (same applies below). The obtained results are shown in Table 1 below.

TABLE 1

| Substrate | Measurement wavelength (nm) | Activity (U) | |
|---|---|---|---|
| | | Wild-type CueO | mCueO(1) |
| p-Phenylenediamine | 470 | 9.70 | 324.48 |
| 2-Methoxyphenol | 470 | 0.00 | 0.00 |
| Catechol | 400 | 0.00 | 0.00 |
| p-Aminophenol | 400 | 3.37 | 20.02 |
| o-Aminophenol | 420 | 14.06 | 61.13 |
| Syringaldazine | 530 | 4.73 | 141.47 |
| Bilirubin | 530 | 0.53 | 33.32 |
| ABTS | 420 | 40.22 | 1109.26 |
| NNS | 490 | 0.00 | 0.00 |
| L-Tyrosine | 490 | 0.00 | 0.00 |

From the above results, it was realized that mCueO (1) exhibits similar substrate specificity to the wild-type CueO, but exhibits more excellent oxidative polymerization ability than the wild-type CueO.

Test Example 2

Evaluation on Oxidative Polymerization Activity of mCueO (1) for Various Substrates (1) Preparation of Substrate Solutions For substrates other than catechin, lignin (derived from rice), and lignin (derived from conifer), each substrate was dissolved in DMSO, and then dissolved in an ion-exchange water, to give a 1 mM DMSO (1.0%) aqueous solution.

For catechin, lignin (derived from rice), and lignin (derived from conifer), each substrate was dissolved in DMSO, and then dissolved in an ion-exchange distilled water, to give a 2 mg/mL DMSO (1.0%) aqueous solution.

(2) Activity Measurement Method

For the following method, an acetate buffer solution (pH 5.5) was used as the buffer solution.

0.88 mL of a 0.1 M buffer solution and 0.1 mL of the substrate solution were mixed in a cuvette (1.0 mL quartz cell, manufactured by SHIMADZU), 0.02 mL of an aqueous solution of mCueO (1) was added thereto, and mixed by inversion. The change in absorbance at each wavelength (measurement wavelength shown in Table 2) from 0 to 30 seconds was measured using a spectrophotometer (UV-2459, manufactured by SHIMADZU).

A unit of the oxidative polymerization activity (U) shows an activity per 1 mg of mCueO (1), when given that the activity that changes absorbance by 1 in 1 minute is 1.

For comparison, the oxidative polymerization activity of wild-type CueO was measured in the same manner. A unit of the oxidative polymerization activity (U) shows an activity per 1 mg of wild-type CueO, when given that the activity that changes absorbance by 1 in 1 minute is 1.

The obtained results are shown in Table 2 below.

1.78 mL of each 200 mM Britton-Robinson buffer solution with a pH value of from 2 to 12 and 0.2 mL of a 100 mM p-phenylenediamine aqueous solution were mixed in a cuvette (1.5 mL UV disposable cell, manufactured by TOP), 0.02 mL of an aqueous solution of mCueO (1) was added to the respective mixture, and mixed by inversion. For thus obtained mixtures each with different pH value, the change in absorbance at 487 nm from 0 to 30 seconds was measured using a spectrophotometer (UV-2459, manufactured by SHIMADZU).

The oxidative polymerization activity was calculated as the activity per 1 mg of mCueO (1) when given that the activity that changes the absorbance by 1 in minute is 1. Then, activity at pH 7.51 among the calculated oxidative polymerization activities was given as 100 to show the relative activity (%) in relation to each pH value upon the oxidative polymerization reaction in FIG. 2.

TABLE 2

| | | Measurement wavelength (nm) | Activity (U) Wild-type CueO | mCueO(1) |
|---|---|---|---|---|
| Diamine compound | o-Phenylenediamine | 430 | 0.00 | 0.00 |
| | m-Phenylenediamine | 405 | 0.00 | 0.00 |
| | p-Phenylenediamine | 470 | 19.55 | 84.22 |
| | N,N-Dimethyl-p-phenylenediamine | 470 | 59.35 | 79.10 |
| | Tolylene-3,4-diamine | 470 | 0.00 | 0.00 |
| | p-Aminodiphenylamine | 470 | 48.86 | 567.28 |
| | 2-Chloro-1,4-phenylenediamine | 450 | 3.10 | 20.33 |
| | 2,5-Diaminotoluene sulfate | 470 | 44.55 | 155.53 |
| Aminophenol compound | o-Aminophenol | 420 | 14.06 | 61.13 |
| | m-Aminophenol | 405 | 0.00 | 0.00 |
| | p-Aminophenol | 405 | 3.37 | 20.02 |
| | 5-Aminoorthocresol | 405 | 0.00 | 0.00 |
| | 2,4-Diaminophenol dihydrochloride | 470 | 69.83 | 845.99 |
| | p-Methylaminophenol sulfate | 470 | 6.51 | 38.47 |
| Phenol compound | 2-Methoxyphenol | 450 | 0.00 | 0.00 |
| | 2,6-Dimethoxyphenol | 470 | 1.43 | 4.61 |
| | 2,6-Dimethoxy-4-metylphenol | 405 | 0.00 | 0.00 |
| | Catechol | 405 | 0.00 | 0.00 |
| | Resorcinol | 405 | 0.00 | 0.00 |
| | Hydroquinone | 405 | 0.00 | 0.00 |
| | Trimethylhydroquinone | 405 | 0.00 | 0.00 |
| | Protocatechuic acid | 405 | 0.00 | 0.00 |
| | Pyrogallol | 405 | 9.44 | 49.31 |
| | Gallic acid | 405 | 1.78 | 5.17 |
| | Propyl gallate | 405 | 0.00 | 0.00 |
| Naphthol compound | 1-Naphthol | 405 | 0.00 | 0.00 |
| | 1,3-Dihydroxynaphthalene | 450 | 2.53 | 11.73 |
| | 1,5-Dihydroxynaphthalene | 470 | 0.78 | 5.32 |
| | 2,6-Dihydroxynaphthalene | 405 | 0.00 | 0.00 |
| Indoles | 4-Hydroxyindole | 405 | 3.33 | 29.39 |
| | 5-Hydroxyindole | 405 | 0.00 | 0.00 |
| Others | Catechin | 405 | 0.00 | 0.00 |
| | Lignin (derived from rice) | 450 | 0.00 | 0.00 |
| | Lignin (derived from conifer) | 450 | 0.00 | 0.00 |

From the above results, it was realized that mCueO (1) exhibits similar substrate specificity to the wild-type CueO, but exhibits more excellent oxidative polymerization ability than the wild-type CueO.

Test Example 3

Evaluation on pH Dependency of Oxidative Polymerization Activity of mCueO (1)

The pH dependency of oxidative polymerization activity of mCueO (1) was evaluated by the following procedures with the use of p-phenylenediamine as the substrate.

From FIG. 2, it was realized that mCueO (1) exhibits sufficient oxidative polymerization activity under neutral and alkaline conditions of pH values of about 6 to 9, and that the optimum pH of mCueO (1) is 7.5 to 8.

Test Example 4

Evaluation on Temperature Dependency of Oxidative Polymerization Activity of mCueO (1)

The temperature dependency of oxidative polymerization activity of mCueO (1) was evaluated by the following procedures with the use of p-phenylenediamine as the substrate.

1.93 mL of a 100 mM potassium phosphate buffer solution (pH 6.0) and 0.05 mL of a 400 mM p-phenylenediamine aqueous solution were mixed in a cuvette (1.5 mL UV disposable cell, manufactured by TOP), preheated at various temperature conditions (30, 35, 40, 45, 50, 55, 60, and 65° C.), 0.02 mL of an aqueous solution of mCueO (1) was added thereto, and mixed by inversion. For each mixture thus obtained, the change in absorbance at 487 nm from 0 to 30 seconds was measured using a spectrophotometer (UV-2459, manufactured by SHIMADZU).

The oxidative polymerization activity was calculated as the activity per 1 mg of mCueO (1) when given that the activity that changes the absorbance by 1 in minute is 1. Then, activity at 65° C. among the calculated oxidative polymerization activities was given as 100 to show relative activity (%) in relation to each temperature upon the oxidative polymerization reaction in FIG. 3.

From the result, it was realized that oxidative polymerization activity of mCueO (1) increases at higher temperature, and that sufficient oxidative polymerization activity can be exhibited at a wide range of temperatures.

Test Example 5

Evaluation on Direct Dye Decomposition Activity of mCueO (1)

The decomposition activity of mCueO (1) with respect to various direct dyes was evaluated by the following procedures.

(1) Preparation of Dye Solution

Natural Orange 6 (2-hydroxy-1,4-naphthoquinone), Acid Orange 8, Acid Violet 17, Remasol brilliant blue, Evans blue, and Acid Blue 80, were dissolved in an ion-exchange distilled water, respectively, to each give a 0.2 mg/mL aqueous solution.

(2) Activity Measurement Method

For the following method, an acetate buffer solution (pH 5.5), a phosphate buffer solution (pH 7.0), or a tris hydrochloric acid buffer solution (pH 9.0) was used as the buffer solution.

0.88 mL of a 0.1 M buffer solution and 0.1 mL of the dye solution were mixed in a cuvette (1.5 mL UV disposable cell, manufactured by TOP), 0.02 mL of an aqueous solution of mCueO (1) was added thereto, and mixed by inversion. The change in absorbance at wavelength between 300 and 700 nm at every after 0, 1, and 2 hours was measured using a spectrophotometer (UV-2459, manufactured by SHIMADZU).

The amount of change in absorbance from just after mixing (0 hour) to after 2 hours from mixing was shown in Table 3.

TABLE 3

| Dye | pH 5.5 | pH 7.0 | Ph 9.0 |
| --- | --- | --- | --- |
| Natural Orange 6 | 0 | 0 | 0 |
| Acid Orange 8 | 0 | 0 | 0 |
| Acid Violet 17 | 0 | 0 | 0 |
| Remasol brilliant blue | 0 | 0 | 0 |
| Evans blue | 0 | 0 | 0 |
| Acid Blue 80 | 0 | 0 | 0 |

From the above results, it was realized that mCueO (1) exhibits no activity of decomposing the direct dye in each of pH conditions.

Test Example 6

Evaluation (1) on pH Stability of mCueO (1)

After subjecting mCueO (1) to a pre-treatment in various pH conditions, the oxidative polymerization activity of mCueO (1) was measured using 2,2'-azino-bis(3-ethylbenzothiazoline-6-sulfonate) (ABTS) as the substrate, thereby evaluating the pH stability of mCueO (1). In specific, the stability was evaluated by the following procedures.

mCueO (1) was dissolved in each 200 mM Britton-Robinson buffer solution with a pH value of from 2 to 12, and incubated at room temperature for 1 hour for the pre-treatment.

Next, 0.2 mL of each mixture from the pre-treatment was mixed with 1.78 mL of a 100 mM potassium phosphate buffer solution (pH 6.0) and 0.2 mL of a 20 mM ABTS aqueous solution in a cuvette (1.5 mL UV disposable cell, manufactured by TOP), and the change in absorbance at 420 nm from 0 to 30 seconds for each mixture was measured using a spectrophotometer (UV-2459, manufactured by SHIMADZU).

The oxidative polymerization activity was calculated as the activity per 1 mg of mCueO (1) when given that the activity that changes the absorbance by 1 in minute is 1. Then, activities after the pre-treatment in pH 6.5 and 8.5 among the calculated oxidative polymerization activities were given as 100 to show the relative remaining activity (%) in relation to each pH value upon the pre-treatment in FIG. 4.

From the above result, it was realized that mCueO (1) maintains sufficient oxidative polymerization activity under a wide range of pH region from 4 to 12, thus is excellent in pH stability.

Test Example 7

Evaluation (2) on pH Stability of mCueO (1)

The pH stability of mCueO (1) was evaluated in the same manner as in Test Example 6, except that the pre-treatment condition was changed to incubation at 50° C. for 10 minutes and cooling with ice after the incubation.

The oxidative polymerization activity was calculated as the activity per 1 mg of mCueO (1) when given that the activity that changes the absorbance by 1 in minute is 1. Then, activity after the pre-treatment in pH 9.96 among the calculated oxidative polymerization activities were given as 100 to show the relative remaining activity (%) in relation to each pH value upon the pre-treatment in FIG. 5.

From the above result, it was realized that even if the temperature during the pre-treatment is increased, mCueO (1) still maintains sufficient oxidative polymerization activity under a wide range of pH region from 4 to 11, thus is excellent in pH stability.

Test Example 8

Evaluation on Thermal Stability of mCueO (1)

After subjecting mCueO (1) to a pre-treatment in various temperature conditions, the oxidative polymerization activity of mCueO (1) was measured using ABTS as the substrate, thereby evaluating the thermal stability of mCueO (1). In specific, the stability was evaluated by the following procedures.

mCueO (1) was dissolved in a 100 mM potassium phosphate buffer solution (pH 6.0), and incubated at different temperature conditions (20, 30, 40, 50, 60, 70, and 80° C.) each for 30 minutes for the pre-treatment.

Next, each mixture from the pre-treatment was cooled with ice. 0.02 mL of each cooled mixture was mixed with 1.78 mL of a 100 mM potassium phosphate buffer solution (pH 6.0) and 0.2 mL of a 20 mM ABTS aqueous solution in a cuvette (1.5 mL UV disposable cell, manufactured by TOP). The change in absorbance at 420 nm from 0 to 30 seconds for each mixture was measured using a spectrophotometer (UV-2459, manufactured by SHIMADZU).

The oxidative polymerization activity was calculated as the activity per 1 mg of mCueO (1) when given that the activity that changes the absorbance by 1 in minute is 1. Then, activities after the pre-treatment at 20 and 30° C. among the calculated oxidative polymerization activities were given as 100 to show the relative remaining activity (%) in relation to each temperature upon the pre-treatment in FIG. 6.

From the above result, it was realized that mCueO (1) maintains sufficient oxidative polymerization activity under a wide temperature range of from 20 to 50° C., thus is excellent in thermal stability.

Test Example 9

Evaluation on Change in Thermal Stability of mCueO (1) with Time

After keeping mCueO (1) at 60° C. for an appropriate period of time, the oxidative polymerization activity of mCueO (1) was measured using ABTS as the substrate, thereby evaluating the change in thermal stability of mCueO (1) with time. In specific, the change in thermal stability with time was evaluated by the following procedures.

mCueO (1) was dissolved in a 100 mM potassium phosphate buffer solution (pH 6.0), and incubated at 60° C. for different period of time (0 to 300 minutes) selected appropriately for the pre-treatment.

Next, each mixture from the pre-treatment was cooled with ice. 0.02 mL of each cooled mixture was mixed with 1.78 mL of a 100 mM potassium phosphate buffer solution (pH 6.0) and 0.2 mL of a 20 mM ABTS aqueous solution in a cuvette (1.5 mL UV disposable cell, manufactured by TOP). The change in absorbance at 420 nm from 0 to 30 seconds for each mixture was measured using a spectrophotometer (UV-2459, manufactured by SHIMADZU).

The oxidative polymerization activity was calculated as the activity per 1 mg of mCueO (1) when given that the activity that changes the absorbance by 1 in minute is 1. Then, activity before subjecting the pre-treatment (0 minute) among the calculated oxidative polymerization activities was given as 100 to show the relative activity (%) in relation to each treatment time upon the pre-treatment in FIG. 7.

From the above result, it was realized that the oxidative polymerization activity of mCueO (1) reduces with time by applying heat to mCueO (1), and that a half-life of the oxidative polymerization activity of mCueO (1) at 60° C. is 30 minutes.

Example 5

Dye of Keratin Fiber with Composition of Invention (1) Preparation of Dyeing Base Agent 0.5 g of p-phenylenediamine, 0.75 g of hydroxyethyl cellulose, 1.0 g of polyoxyethylene (20) hardened castor oil (HC-20), and 0.5 g of lactic acid were mixed, pH of the mixture was adjusted to pH 9.0 with monoethanolamine, and the weight was adjusted to 50 g with ion-exchange distilled water.

(2) Dyeing Test

In Example 5, 2 g of the dyeing base agent and an aqueous solution of mCueO (1) (4 U equivalent amount) were mixed, and thus obtained mixture was applied to 1 g of a bundle of human white hair and one piece of wool cloth (3×5 cm). The bundle of human white hair and wool cloth after the application were each kept at 30° C. for 30 minutes.

As a control, the same procedure was carried out except that the mCueO (1) solution was not added and only the dyeing base agent was directly applied.

Herein, the unit U represents the activity per 1 mg of mCueO (1) when given that using 5 mM p-phenylenediamine as the substrate and under pH of 9.0 the activity that changes absorbance at 470 nm by 1 in 1 minute is 1.

(3) Color Difference Measurement

For the bundle of human white hair and wool cloth before being dyed, and dyed bundle of human hair and wool cloth, L value, a value, and b value were measured using a colorimeter (manufactured by MINOLTA Inc., Trade Name: Chromomometer CM-3610d). A ΔE value was calculated on the basis of these L value, a value, and b value, using the following Formula (1). The results are shown in Table 4.

Herein, the ΔE value represents the color difference between color tone before the dye and color tone after the dye. The larger the numerical value the higher the dyeing effect.

Expression 1

$$\Delta E = \sqrt{(\Delta L)^2 + (\Delta a)^2 + (\Delta b)^2} \quad (1)$$

TABLE 4

|  | Bundle of human white hair | Wool cloth |
|---|---|---|
| Example 1 | 45.5 | 50.7 |
| Control | 17.4 | 7.7 |

From the above result, it was shown that high dyeing effect can be achieved on any of hair and wool cloth by using mCueO (1).

the ΔE value of commercially available hair manicure is around 40, and thus as from the result above, the composition of the invention can be suitably used for dyeing hair.

Example 6

Production of Modified CueO (2):CueO (Δα5-7)' of Invention 6-1. Production of Recombinant Vector An amino acid sequence of the modified CueO (2) (SEQ ID NO: 15) which is the target in present Example is an amino acid sequence obtained by removing sequences constituting helices 5, 6, and 7, and an amino acid sequence of the structure unknown sequence existing between the helix 6 and the helix 7 (from Pro at $329^{th}$ position to His at $378^{th}$ position in SEQ ID NO: 2, shown by SEQ ID NO: 13) and instead inserting two residues of Ala-Ala as the spacer, and adding a histidine tag to C-terminus.

The base sequence coding for modified CueO (2) is a sequence obtained by altering the base sequence ggtggt which corresponds to a Gly-Gly sequence in above mCueO (1):CueO (Δα5-7) to a base sequence gcggcc which corresponds to an Ala-Ala sequence. Accordingly, a NotI recognition site is newly added, and thus the recombinant vector containing the base sequence coding for modified CueO (2) becomes the base for allowing the insertion of DNA fragment of various size to the position of a gene corresponding to helices 5, 6, and 7 in CueO.

A gene was synthesized by a PCR technique employing synthetic oligonucleotide primers shown below with the use of the recombinant vector pUC18-CueO(Δα5-7) obtained in Example 2 as the template.

```
                                       (SEQ ID NO: 16)
CueO-2Ala-1:  5'-ctctccatggacgcggccgcaacaaaatc-3'
              (gcggccgc at positions 13 to 20 is
              NotI recognition site)

(SEQ ID NO: 17)
M13(-21):     5'-gttttcccagtcacgac-3'
```

For the reaction, a PCR reaction solution shown below was used.

PCR Reaction Solution

| | |
|---|---|
| pUC18-CueO (Δα5-7) (46 ng/μl) | 1 μl |
| Primers (20 pmol/μl) | 1 μl of each |
| PCR buffer solution | 5 μl |
| dNTP mix. (2.5 mM) | 4 μl |
| Purified water | 37.75 μl |
| TOYOBO blend Taq | 0.25 μl |

Reaction Cycle (1) Preheat: 95° C., 5 mins (2) Denaturalization: 95° C., 0.5 mins (3) Annealing: 50° C., 1 min (4) Extension: 72° C., 1 min→returns to (2) (35 cycles)

(5) Extension: 72° C., 10 mins

After the above PCR reaction, the amplified product was concentrated by ethanol precipitation described below.

Ethanol Precipitation

To 50 μL of a sample, 5 μL of 3M sodium acetate and 100 μL of 100% ethanol were added, and the mixture was left still at −80° C. for 10 minutes. Thereafter, centrifugation was carried out at 14,000 rpm for 5 minutes, and the supernatant was discarded. To the pellet, 500 μL of 70% ethanol was added for washing, and then centrifugation was again carried out at 14,000 rpm for 5 minutes. The supernatant was discarded. The remaining pellet was dried under reduced pressure for about 5 minutes, and dissolved in 10 μL of a solution for restriction enzyme digestion.

Restriction Enzyme Digestion

The restriction enzyme treatment of an amplified fragment and a pUC18-CueO (Δα5-7) vector was carried out in the following reaction systems:

Reaction System (for Treatment of Amplified Fragment)

| | |
|---|---|
| CueO amplified fragment | about 20 μg |
| TOYOBO H buffer solution | 1.0 μL |
| BamHI (manufactured by TOYOBO) | 0.5 μL |
| NcoI (manufactured by TOYOBO) | 0.5 μL |
| Purified water | 8.0 μL |
| Total | 10.0 μL |

Reaction System (for Treatment of pUC18-CueO (Δα5-7))

| | |
|---|---|
| pUC18-CueO (Δα5-7) | about 20 μg |
| TOYOBO H buffer solution | 0.7 μL |
| BamHI (manufactured by TOYOBO) | 0.3 μL |
| NcoI (manufactured by TOYOBO) | 0.3 μL |
| Purified water | 5.7 μL |
| Total | 8.0 μL |

After preparing each solution, it was left overnight at 37° C. for digestion, respectively.

Agarose Gel Electrophoresis

2 μL of dye was added for every restriction digest, and the resultant was loaded on a 2% agarose gel (1×TAE buffer solution). Electrophoresis was run at 100 V for 1 hour, and then DNA bands were stained using an ethidium bromide solution. Under confirming with the UV illuminator, the PCR fragment of 400 bp and pUC18-CueO (Δα5-7) fragment of 3.7 kb were cut.

DNA Fragment Extraction

Each DNA fragment was extracted from the agarose gel according to a protocol of QIAEX II (manufactured by QUIAGEN). For the elution, 10 μL of a TE buffer solution was used, respectively.

Ligation

The PCR product of NcoI-BamHI digested fragment and the digested fragment of pUC18-CueO (Δα5-7) were linked in the reaction solution shown below according to a protocol of Takara DNA Ligation Kit Ver. 2.1 (manufactured by Takara Bio Inc.).

| | |
|---|---|
| PCR product gel extraction fragment | 4.5 μL |
| pUC18-CueO (Δα5-7) gel extraction fragment | 0.5 μL |
| Ligation Kit Ver. 2.1, Sol. I | 5.0 μL |
| Total | 10.0 μL |

After preparing the solution, it was left overnight at 16° C. for a reaction to take place using Thermal Cycler. Thereafter, ethanol precipitation was subjected, and the pellet obtained was dissolved in 10 μL of sterile water.

From the obtained recombinant vector, a base sequence represented by SEQ ID NO: 14 was confirmed. The obtained recombinant vector was given as pUC18-CueO(Δα5-7)'.

6-2. Production of Transformant

5 μL of the sample solution that had been subjected to ethanol precipitation according to the above procedure was added to 50 μL of *E. coli* BL21 (DE3) competent cell, and subjected to stirring. Then, whole amount was put in a cuvette (1 mm electrode gap). Electroporation was carried out using a Micro Pulser manufactured by Bio-Rad with Program EC1. *E. coli* was suspended in 1 mL of LB medium, recovered, and shaked at 37° C. for 1 hour. Thereafter, the cultured cell was plated on an LB agar medium containing ampicillin. The plate was left overnight at 37° C.

The competent cell was prepared in accordance with the Bio-Rad instruction.

6-3. Production and Purification of Recombinant Protein

The transformant obtained was cultured by following two steps, and the recombinant protein of the invention was expressed.

(1) Pre-Culture (Test Tube)

O/N aerobic culturing was subjected in an LB medium containing 0.1 mg/mL ampicillin, at 37° C.

(2) Main Culture (2 L Conical Flask with Baffle)

1 mM CuCl$_2$ and 0.5 mM IPTG were added to 400 mL of the above medium, and aerobic culturing was subjected at 32° C. for 12 hours.

Thereafter, cells were harvested by centrifugation, and washed with 0.85% aqueous sodium chloride solution, and then osmotic shock was performed straight after.

Osmotic Shock

The cells were suspended in a solution containing 20% sucrose and 100 mM Tris-HCl buffer solution (pH 8.0), that is cooled with ice, and left still for 10 minutes in an ice bath. Thereafter, the cells were collected by centrifugation.

Next, the cells were suspended in ice-cold distilled water, and left still for 10 minutes in an ice bath. Thereafter, the cells were collected by centrifugation. This was a crude enzyme solution.

IMAC

The sample was overlaid on Ni-NTA agarose column (40 mL) equilibrated with a 50 mM Tris-HCl buffer solution (pH 8.0), and then washed with the same buffer solution.

The adsorbed protein was eluted with the same buffer solution containing 200 mM imidazole. The elution fraction was concentrated, and dialyzed against 50 mM Tris-HCl buffer solution (pH 8.0).

The recombinant protein of the invention purified in the above manner was given as modified CueO (2):CueO (Δα5-7)' (hereinafter, also referred to as 'mCueO (2)').

The SEQ ID NO: 15 shows an amino acid sequence of immature type, while the amino acid sequence of from 1$^{st}$ to 28$^{th}$ positions is a signal sequence.

Example 7

Production of Modified CueO (3):CueO (Δα6-7)' of Invention

An amino acid sequence of the modified CueO (3) (SEQ ID NO: 21) which is the target in present Example is an amino acid sequence obtained by removing sequences constituting helices 6 and 7, and an amino acid sequence of the structure unknown sequence existing between the helix 6 and the helix 7, and adding a histidine tag to the C-terminus.

A fragment of gene coding for 9 amino acids for maintaining a steric structure and helix 5 (SEQ ID NO: 18, the amino acid sequence thereof is SEQ ID NO: 19) was prepared, and the gene was inserted in pUC18-CueO(Δα5-7)' obtained in Example 6, to prepare a recombinant vector. In specific, a gene was synthesized by a PCR technique employing synthetic oligonucleotide primers shown below.

```
                                        (SEQ ID NO: 22)
CueO-α5-1:
5'-ctctccatggacccgatgctcgatatgatggggatgcagatgctaat
ggagaaatatggcgc-3'
(ccatgg at positions 5 to 10 is NcoI recognition
site)
```

```
                                        (SEQ ID NO: 23)
CueO-α5- 1R:
5'-taaattagcggccgcagcacctgcagcaccagctgcgccatatttct
ccattagcatctgc-3'
(gcggccgc at positions 8 to 15 is NotI recognition
site)
```

For the reaction, a PCR reaction solution shown below was used.

PCR Reaction Solution

| Primers (20 pmol/μL) | 1 μl of each |
|---|---|
| PCR buffer solution | 5 μl |
| dNTP mix. (2.5 mM) | 4 μl |
| Purified water | 38.75 μl |
| TOYOBO blend Taq | 0.25 μl |

Reaction Cycle
 (1) Preheat: 95° C., 5 mins
 (2) Denaturalization: 95° C., 0.5 mins
 (3) Annealing: 50° C., 0.5 mins
 (4) Extension: 72° C., 0.5 mins→returns to (2) (40 cycles)
 (5) Extension: 72° C., 10 mins After the above PCR reaction, the amplified product was concentrated by ethanol precipitation described below.

Ethanol Precipitation

To 50 μL of a sample, 5 μl of 3M sodium acetate and 100 μL of 100% ethanol were added, and the mixture was left still at −80° C. for 10 minutes. Thereafter, centrifugation was carried out at 14,000 rpm for 5 minutes, and the supernatant was discarded. To the pellet, 500 μL of 70% ethanol was added for washing, and then centrifugation was again carried out at 14,000 rpm for 5 minutes. The supernatant was discarded. The remaining pellet was dried under reduced pressure for about 5 minutes, and dissolved in 10 μL of a solution for restriction enzyme digestion.

Restriction Enzyme Digestion

The restriction enzyme treatment of an amplified fragment and a pUC18-CueO(Δα5-7)' vector was carried out in the following reaction systems:

Reaction System (for Treatment of PCR Amplified Fragment)

| PCR amplified fragment | about 20 μg |
|---|---|
| TOYOBO H buffer solution | 1.0 μL |
| NcoI (manufactured by TOYOBO) | 0.5 μL |
| NotI (manufactured by TOYOBO) | 0.5 μL |
| Purified water | 8.0 μL |
| Total | 10.0 μL |

Reaction System (for Treatment of pUC18-CueO(Δα5-7)')

| pUC 18-CueO(Δα5-7)' | about 20 μg |
|---|---|
| TOYOBO H buffer solution | 0.7 μL |
| NcoI (manufactured by TOYOBO) | 0.3 μL |
| NotI (manufactured by TOYOBO) | 0.3 μL |
| Purified water | 5.7 μL |
| Total | 8.0 μL |

After preparing each solution, it was left overnight at 37° C. for digestion, respectively.

Agarose Gel Electrophoresis

2 μL of dye was added for every restriction digest, and the resultant was loaded on a 2% agarose gel (1×TAE buffer solution). Electrophoresis was run at 100 V for 1 hour, and then DNA bands were stained using an ethidium bromide solution. Under confirming with the UV illuminator, the PCR fragment of 90 bp and pUC18-CueO(Δα5-7)' fragment of 4.1 kb were cut.

29

DNA Fragment Extraction

Each DNA fragment was extracted from the agarose gel according to a protocol of QIAEX II (manufactured by QUIAGEN). For the elution, 10 µL of a TE buffer solution was used, respectively.

Ligation

The PCR product of NcoI-NotI digested fragment and the digested fragment of pUC18-CueO(Δα5-7)' were linked in the reaction solution shown below according to a protocol of Takara DNA Ligation Kit Ver. 2.1 (manufactured by Takara Bio Inc.).

| | |
|---|---|
| PCR product gel extraction fragment | 4.5 µL |
| pUC18-CueO(Δα5-7)' gel extraction fragment | 0.5 µL |
| Ligation Kit Ver. 2.1, Sol. I | 5.0 µL |
| Total | 10.0 µL |

After preparing the solution, it was left overnight at 16° C. for a reaction to take place using Thermal Cycler. Thereafter, ethanol precipitation was subjected, and the pellet obtained was dissolved in 10 µL of sterile water.

From the obtained recombinant vector, a base sequence represented by SEQ ID NO: 20 was confirmed. The obtained recombinant vector was given as pUC18-CueO(Δα6-7).

With the use of this vector, the transformant was produced in the same manner as in Example 6, and also the recombinant protein was produced and purified. The recombinant protein of the invention purified in such manner was given as modified CueO (3):CueO(Δα6-7) (hereinafter, also referred to as 'mCueO (3)'). The SEQ ID NO: 21 shows an amino acid sequence of immature type, while the amino acid sequence of from $1^{st}$ to $28^{th}$ positions is a signal sequence.

Example 8

Production of Modified CueO (4):CueO (Δα5) of Invention

An amino acid sequence of the modified CueO (4) (SEQ ID NO: 27) which is the target in present Example is an amino acid sequence obtained by removing a sequence constituting helix 5, and adding a histidine tag to the C-terminus.

A fragment of gene coding for 10 amino acids for maintaining a steric structure and helices 6 and 7 (SEQ ID NO: 24, the amino acid sequence thereof is SEQ ID NO: 25) was prepared, and the gene was inserted in pUC18-CueO(Δα5-7)' obtained in Example 6, to prepare a recombinant vector. In specific, a gene was synthesized by a PCR technique employing synthetic oligonucleotide primers shown below with the use of pUC18-CueO(Δα5-7)' as the template.

(SEQ ID NO: 28)
CueO-α6-1:
5'-tatttagcggccgcaggagcagcaggagcagcaggagatcaggcgat
ggccgggatg-3'
(gcggccgc at positions 4 to 11 is NotI recognition
site)

(SEQ ID NO: 29)
M13(-21):
5'-gttttcccagtcacgac-3'

30

For the reaction, a PCR reaction solution shown below was used.

PCR Reaction Solution

| | |
|---|---|
| pUC18-CueO(Δα5-7)' | 0.5 µL |
| Primers (20 pmol/µL) | 1 µL of each |
| PCR buffer solution | 5 µL |
| dNTP mix. (2.5 mM) | 4 µL |
| Purified water | 37.25 µL |
| TOYOBO blend Taq | 0.25 µL |

Reaction Cycle
 (1) Preheat: 95° C., 5 mins
 (2) Denaturalization: 95° C., 0.5 mins
 (3) Annealing: 50° C., 0.5 mins
 (4) Extension: 72° C., 0.5 mins→returns to (2) (40 cycles)
 (5) Extension: 72° C., 10 mins After the above PCR reaction, the amplified product was concentrated by ethanol precipitation described below.

Ethanol Precipitation

To 50 µL of a sample, 5 µL of 3M sodium acetate and 100 µL of 100% ethanol were added, and the mixture was left still at −80° C. for 10 minutes. Thereafter, centrifugation was carried out at 14,000 rpm for 5 minutes, and the supernatant was discarded. To the pellet, 500 µL of 70% ethanol was added for washing, and then centrifugation was again carried out at 14,000 rpm for 5 minutes. The supernatant was discarded. The remaining pellet was dried under reduced pressure for about 5 minutes, and dissolved in 10 µL of a TE buffer solution.

Agarose Gel Electrophoresis

2 µL of dye was added to the PCR product which had been subjected to the ethanol precipitation, and the resultant was loaded on a 2% agarose gel (1×TAE buffer solution). Electrophoresis was run at 100 V for 1 hour, and then DNA bands were stained using an ethidium bromide solution. Under confirming with the UV illuminator, the PCR fragment of 530 bp was cut.

DNA Fragment Extraction

Each DNA fragment was extracted from the agarose gel according to a protocol of QIAEX II (manufactured by QUIAGEN). For the elution, 10 µL of a TE buffer solution was used, respectively.

TA Cloning

The PCR product was TA, cloned according to a protocol of pGEM-T Easy Vector System I (manufactured by Promega).

After preparing the solution, it was left overnight at 4° C. for a reaction to take place. Thereafter, ethanol precipitation was subjected, and the pellet obtained was dissolved in 10 µL of sterile water.

A base sequence of the obtained recombinant vector was confirmed. The obtained recombinant vector was given as pGEM-α6-7.

Restriction Enzyme Digestion

The restriction enzyme treatment of pGEM-α6-7 and pUC18-CueO(Δα5-7)' was carried out in the following reaction systems:

Reaction System (for pGEM-α6-7)

| | |
|---|---|
| pGEM-α6-7 | about 20 µg |
| TOYOBO H buffer solution | 1.0 µL |
| NotI (manufactured by TOYOBO) | 0.5 µL |

-continued

| | |
|---|---|
| BamHI (manufactured by TOYOBO) | 0.5 μL |
| Purified water | 8.0 μL |
| Total | 10.0 μL |

Reaction System (for pUC18-CueO(Δα5-7)')

| | |
|---|---|
| pUC18-CueO(Δα5-7)' | about 20 μg |
| TOYOBO H buffer solution | 1.0 μL |
| NotI (manufactured by TOYOBO) | 0.5 μL |
| BamHI (manufactured by TOYOBO) | 0.5 μL |
| Purified water | 8.0 μL |
| Total | 10.0 μL |

After preparing each solution, it was left overnight at 37° C. for digestion, respectively.

Agarose Gel Electrophoresis

2 μL of dye was added for every restriction digest, and the resultant was loaded on a 2% agarose gel (1×TAE buffer solution). Electrophoresis was run at 100 V for 1 hour, and then DNA bands were stained using an ethidium bromide solution. Under confirming with the UV illuminator, the fragment of 480 bp and pUC18-CueO(Δα5-7)' fragment of 3.7 kb were cut.

DNA Fragment Extraction

Each DNA fragment was extracted from the agarose gel according to a protocol of QIAEX II (manufactured by QUIAGEN). For the elution, 10 μL of a TE buffer solution was used, respectively.

Ligation

The NotI-BamHI digested fragment of pGEM-α6-7 and pUC18-CueO(Δα5-7)' were linked in the reaction solution shown below according to a protocol of Takara DNA Ligation Kit Ver. 2.1 (manufactured by Takara Bio Inc.).

| | |
|---|---|
| pGEM-α6-7 extraction fragment | 4.5 μL |
| pUC18-CueO(Δα5-7)' gel extraction fragment | 0.5 μL |
| Ligation Kit Ver. 2.1, Sol. I | 5.0 μL |
| Total | 10.0 μL |

After preparing the solution, it was left overnight at 16° C. for a reaction to take place using Thermal Cycler. Thereafter, ethanol precipitation was subjected, and the pellet obtained was dissolved in 10 μL of sterile water.

From the obtained recombinant vector, a base sequence represented by SEQ ID NO: 26 was confirmed. The obtained recombinant vector was given as pUC18-CueO(Δα5).

With the use of this vector, the transformant was produced in the same manner as in Example 6, and also the recombinant protein was produced and purified. The recombinant protein of the invention purified in such manner was given as modified CueO (4):CueO(Δα5) (hereinafter, also referred to as 'mCueO (4)'). The SEQ ID NO: 27 shows an amino acid sequence of immature type, while the amino acid sequence of from $1^{st}$ to $28^{th}$ positions is a signal sequence.

Example 9

Production of Modified CueO (5):CueO(Δα5-7)'+½α5 of Invention

An amino acid sequence of the modified CueO (5) (SEQ ID NO: 33) which is the target in present Example is an amino acid sequence obtained by removing sequences constituting a half of the C-terminus side of helix 5, and helices 6 and 7, and an amino acid sequence of the structure unknown sequence existing between the helix 6 and the helix 7, and adding a histidine tag to the C-terminus. In other words, the modified CueO (5) includes only a half of N-terminus side of helix 5.

A fragment of gene coding for 5 amino acids for maintaining a steric structure and a half of helix 5 (SEQ ID NO: 30, the amino acid sequence thereof is SEQ ID NO: 31) was prepared, and the gene was inserted in pUC18-CueO(Δα5-7)' obtained in Example 6, to prepare a recombinant vector. In specific, a gene was synthesized by a PCR technique employing synthetic oligonucleotide primers shown below.

```
CueO-par α5-1:
                                        (SEQ ID NO: 34)
5'-ctctccatggacccgatgctcgatatgatggggatggga-3'
(ccatgg at positions 5 to 10 is NcoI
recognition site)

CueO-par α5-1R:
                                        (SEQ ID NO: 35)
5'-aataatagcggccgcacctgctcccatcoccatcatatc-3'
(gcggccgc at positions 8 to 15 is NotI
recognition site)
```

For the reaction, a PCR reaction solution shown below was used.

PCR Reaction Solution

| | |
|---|---|
| Primers (20 pmol/μL) | 1 μL of each |
| PCR buffer solution | 5 μL |
| dNTP mix. (2.5 mM) | 4 μL |
| Purified water | 38.75 μL |
| TOYOBO blend Taq | 0.25 μL |

Reaction Cycle
(1) Preheat: 95° C., 5 mins
(2) Denaturalization: 95° C., 0.5 mins
(3) Annealing: 50° C., 0.5 mins
(4) Extension: 72° C., 0.5 mins→returns to (2) (40 cycles)
(5) Extension: 72° C., 10 mins After the above PCR reaction, the amplified product was concentrated by ethanol precipitation described below.

Ethanol Precipitation

To 50 μL of a sample, 5 μL of 3M sodium acetate and 100 μL of 100% ethanol were added, and the mixture was left still at −80° C. for 10 minutes. Thereafter, centrifugation was carried out at 14,000 rpm for 5 minutes, and the supernatant was discarded. To the pellet, 500 μL of 70% ethanol was added for washing, and then centrifugation was again carried out at 14,000 rpm for 5 minutes. The supernatant was discarded. The remaining pellet was dried under reduced pressure for about 5 minutes, and dissolved in 10 μL of a solution for restriction enzyme digestion.

Restriction Enzyme Digestion

The restriction enzyme treatment of an amplified fragment and a pUC18-CueO(Δα5-7)' vector was carried out in the following reaction systems:

Reaction System (for Treatment of PCR Amplified Fragment)

| | |
|---|---|
| PCR amplified fragment | about 20 μg |
| TOYOBO H buffer solution | 1.0 μL |
| NcoI (manufactured by TOYOBO) | 0.5 μL |

-continued

| | |
|---|---|
| NotI (manufactured by TOYOBO) | 0.5 μL |
| Purified water | 8.0 μL |
| Total | 10.0 μL |

Reaction System (for pUC18-CueO(Δα5-7)')

| | |
|---|---|
| pUC18-CueO(Δα5-7)' | about 20 μg |
| TOYOBO H buffer solution | 0.7 μL |
| NcoI (manufactured by TOYOBO) | 0.3 μL |
| NotI (manufactured by TOYOBO) | 0.3 μL |
| Purified water | 5.7 μL |
| Total | 8.0 μL |

After preparing each solution, it was left overnight at 37° C. for digestion, respectively.

Agarose Gel Electrophoresis

2 μL of dye was added for every restriction digest, and the resultant was loaded on a 2% agarose gel (1×TAE buffer solution). Electrophoresis was run at 100 V for 1 hour, and then DNA bands were stained using an ethidium bromide solution. Under confirming with the UV illuminator, the PCR fragment of 50 bp and pUC18-CueO(Δα5-7)' fragment of 4.1 kb were cut.

DNA Fragment Extraction

Each DNA fragment was extracted from the agarose gel according to a protocol of QIAEX II (manufactured by QUIAGEN). For the elution, 10 μL of a TE buffer solution was used, respectively.

Ligation

The PCR product of NcoI-NotI digested fragment and the digested fragment of pUC18-CueO(Δα5-7)' were linked in the reaction solution shown below according to a protocol of Takara DNA Ligation Kit Ver. 2.1 (manufactured by Takara Bio Inc.).

| | |
|---|---|
| PCR product gel extraction fragment | 4.5 μL |
| pUC18-CueO(Δα5-7)' gel extraction fragment | 0.5 μL |
| Ligation Kit Ver. 2.1, Sol. I | 5.0 μL |
| Total | 10.0 μL |

After preparing the solution, it was left overnight at 16° C. for a reaction to take place using Thermal Cycler. Thereafter, ethanol precipitation was subjected, and the pellet obtained was dissolved in 10 μL of sterile water.

From the obtained recombinant vector, a base sequence represented by SEQ ID NO: 32 was confirmed. The obtained recombinant vector was given as pUC18-CueO(Δα5-7)'+½α5.

With the use of this vector, the transformant was produced in the same manner as in Example 6, and also the recombinant protein was produced and purified. The recombinant protein of the invention purified in such manner was given as modified CueO (5):CueO(Δα5-7)'+½α5 (hereinafter, also referred to as 'mCueO (5)'). The SEQ ID NO: 33 shows an amino acid sequence of immature type, while the amino acid sequence of from $1^{st}$ to $28^{th}$ positions is a signal sequence.

Test Example 10

Evaluation on Oxidative Polymerization Activity of mCueO (2) to (5) for Representative Substrates of Laccase (1) Preparation of Substrate Solutions p-phenylenediamine (PPD) and 2,2'-azino-bis(3-ethylbenzothiazoline-6-sulfonate) (ABTS) were dissolved in an ion-exchange distilled water, respectively, to each give a 50 mM aqueous solution.

o-aminophenol (OAP) was dissolved in DMSO, and then dissolved in an ion-exchange distilled water, to each give a 50 mM DMSO (10%)-aqueous solution.

(2) Activity Measurement Method 0.875 mL of a 200 mM acetic acid buffer solution (pH 5.5), 0.025 mL of an aqueous solution (0.5 mg/mL) of each enzyme (mCueO (2) to (5) and wild-type CueO), and 0.1 mL of each substrate solution were mixed in a cuvette (1.5 mL UV disposable cell, manufactured by TOP). The change in absorbance at each measurement wavelength (measurement wavelength for PPD was 470 nm, and for ABTS and OAP was 420 nm) was measured using a spectrophotometer (UV-2459, manufactured by SHIMADZU).

The change in absorbance per min per mol for the wild-type CueO was given as 1 and compared with those of other enzymes. A result in relation to PPD was shown in FIG. 8, a result in relation to OAP was shown in FIG. 9, and a result in relation to ABTS was shown in FIG. 10.

From these results, it was realized that the oxidative polymerization ability of mCueO (2) to (5) is more excellent than that of wild-type CueO.

Preparation Examples

Hereinbelow, Preparation Examples of the composition for dyeing keratin fiber of the invention will be shown. The compositions below are those capable of dyeing white hair to be unnoticeable when applied to white hairs. Herein, the blending amount is shown in weight %.

Preparation Example 1

Gel Type

| | |
|---|---|
| p-phenylenediamine | 1.5 |
| resorcin | 0.3 |
| m-aminophenol | 0.1 |
| Recombinant protein of the invention | 0.1 |
| sodium ascorbate | 1.0 |
| hydroxyethyl cellulose | 1.0 |
| citric acid | adequate amount |
| monoethanolamine | adequate amount |
| purified water | remainder |
| Total | 100.0 |

Preparation Example 2

Cream Type

| | |
|---|---|
| p-phenylenediamine | 1.0 |
| p-aminophenol | 0.8 |
| m-aminophenol | 0.1 |
| cetanol | 6.0 |
| Recombinant protein of the invention | 0.05 |
| polyoxyethylene (20) cetyl ether | 4.0 |
| stearyl trimethylammonium chloride | 1.0 |
| L-cysteine hydrochloride | 0.2 |
| citric acid | adequate amount |
| monoethanolamine | adequate amount |
| purified water | remainder |
| Total | 100.0 |

Preparation Example 3

Cream Type

| | |
|---|---|
| 5,6-dihydroxyindoline | 1.0 |
| 5,6-dihydroxyindole-2-carboxylic acid | 0.5 |
| o-aminophenol | 0.5 |
| ethanol | 5.0 |
| stearyl alcohol | 1.5 |
| Recombinant protein of the invention | 0.2 |
| polyoxyethylene (40) hardened castor oil | 3.0 |
| polyglycerin fatty acid ester | 4.0 |
| N-acetylcysteine | 0.1 |
| xanthane gum | 0.5 |
| Aculyn (registered trademark) 22 | 0.1 |
| hydroxyethyl cellulose | 0.1 |
| monoisopropanolamine | adequate amount |
| monoethanolamine | adequate amount |
| purified water | remainder |
| Total | 100.0 |

Preparation Example 4

Aerosol Type

| | |
|---|---|
| toluene-2,5-diamine | 1.5 |
| p-aminophenol | 0.2 |
| resorcin | 0.1 |
| m-aminophenol | 0.1 |
| polyoxyethylene (5) cetyl ether | 2.0 |
| propyleneglycol | 5.0 |
| sodium sulfite | 0.3 |
| monoethanolamine | adequate amount |
| citric acid | adequate amount |
| Recombinant protein of the invention | 0.3 |
| liquefied petroleum gas | 4.0 |
| purified water | remainder |
| Total | 100.0 |

INDUSTRIAL APPLICABILITY

According to the invention, a recombinant protein excellent in enzymatic activity for oxidizing p-phenylenediamine or the like as compared to wild-type CueO can be provided, and keratin fiber can be simply and efficiently dyed even under an alkaline condition by employing an enzyme in place of an oxidizing agent such as hydrogen peroxide.

DESCRIPTION OF REFERENCE NUMERALS AND SIGNS

Figure 1:
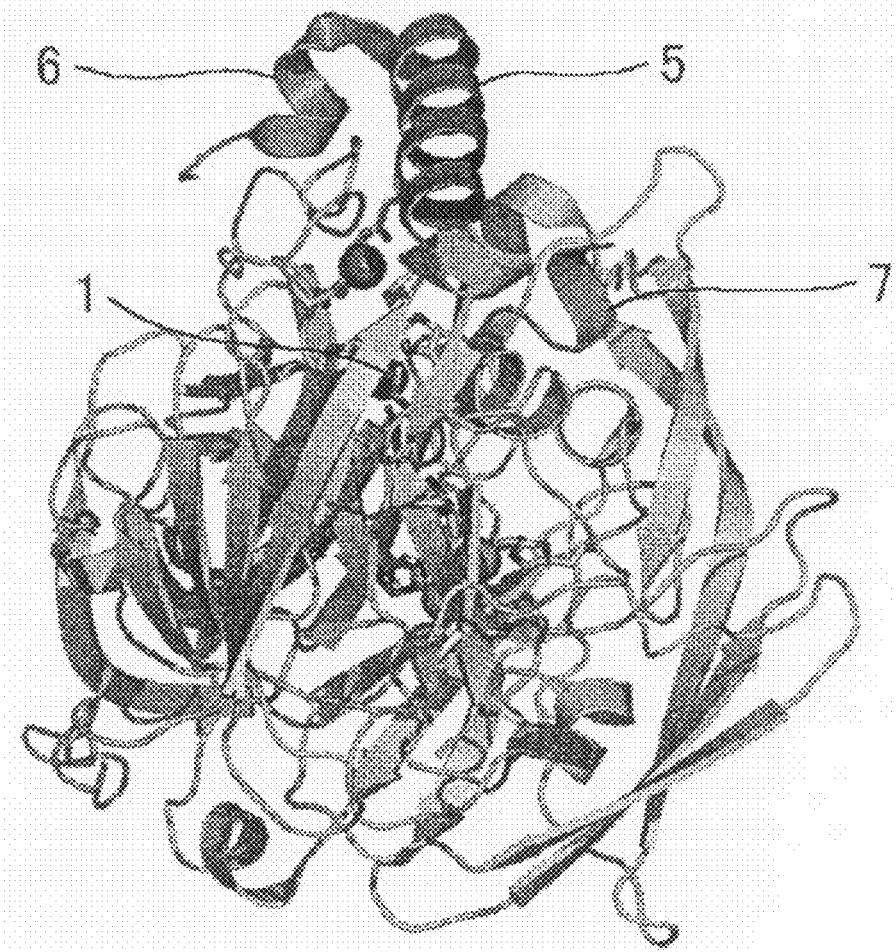
FIG. 1 is a diagram showing a conformation of wild-type CueO (SEQ ID NO: 1) derived from *Escherichia coli*.
Figure 2:
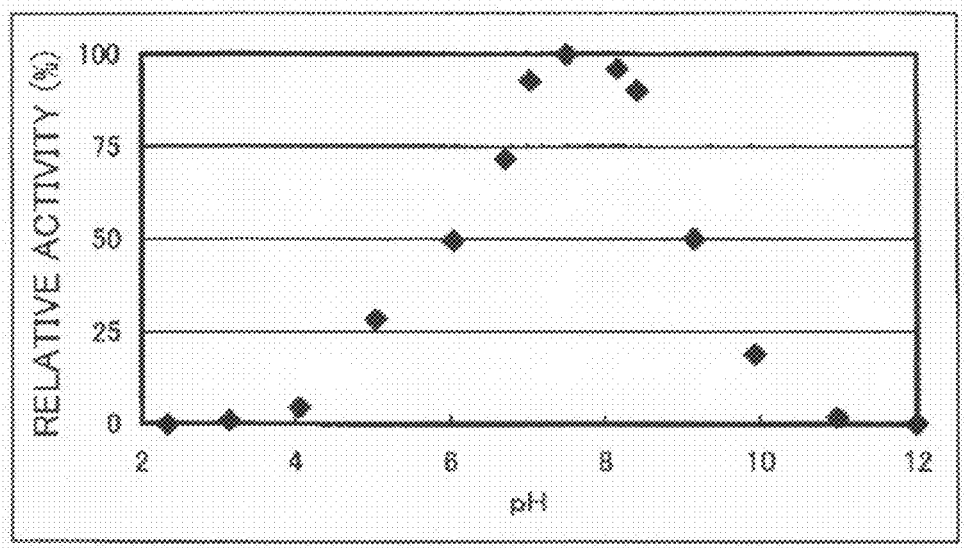
FIG. 2 is a graph showing a result of evaluation on pH dependency of oxidative polymerization activity of mCueO (1) in Test Example 3.
Figure 3:
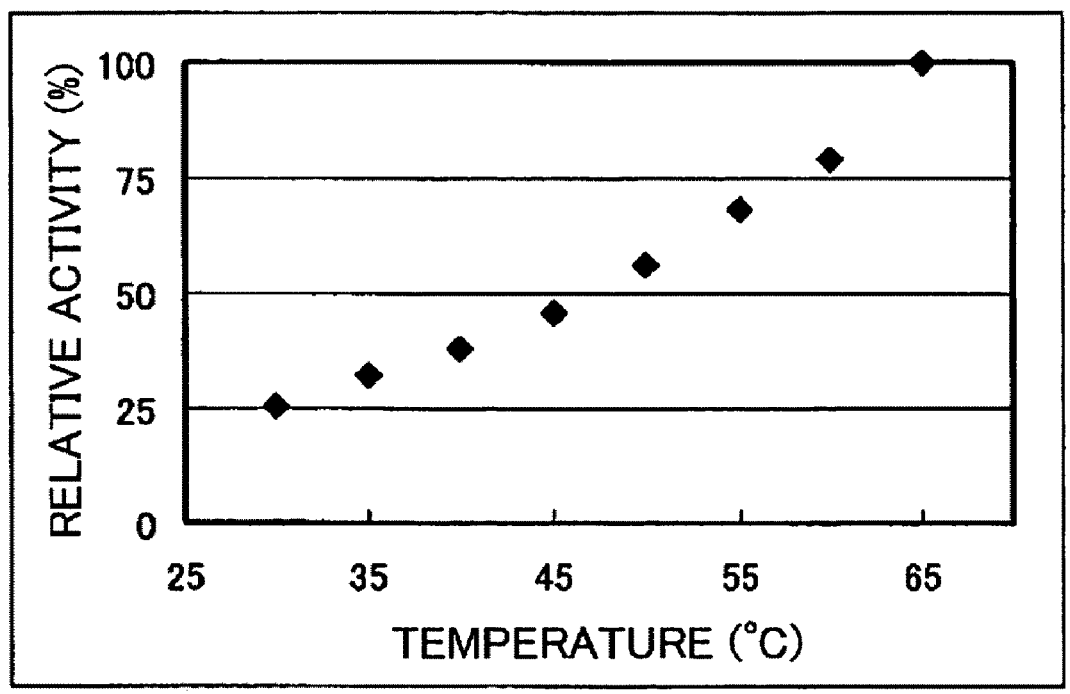
FIG. 3 is a graph showing a result of evaluation on temperature dependency of oxidative polymerization activity of mCueO (1) in Test Example 4.
Figure 4:
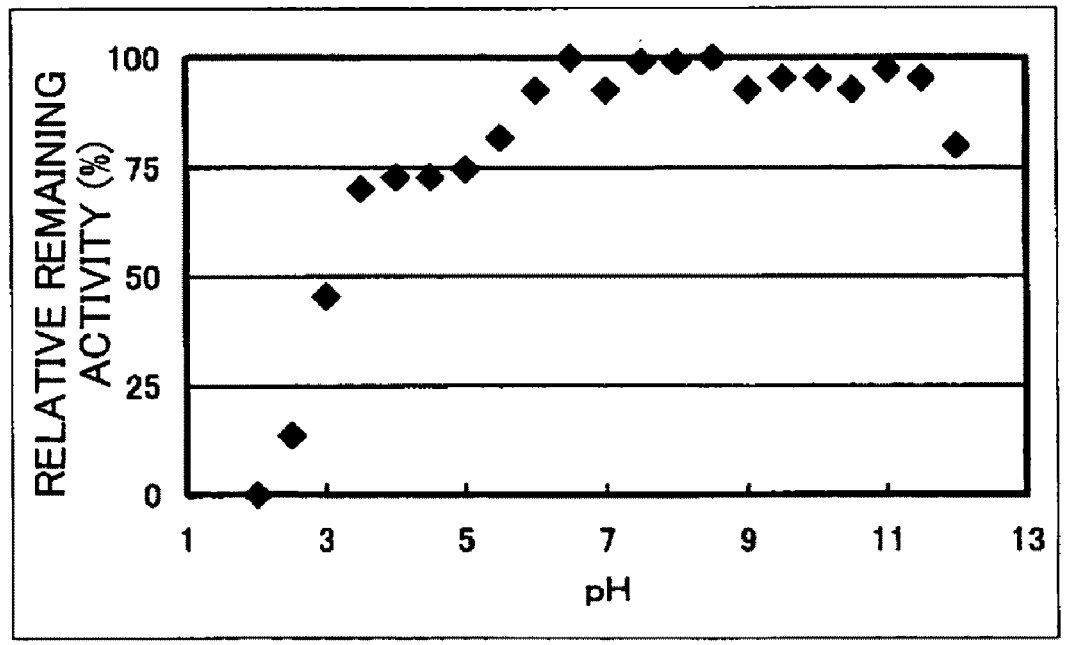
FIG. 4 is a graph showing a result of evaluation on pH stability of mCueO (1) in Test Example 6.
Figure 5:
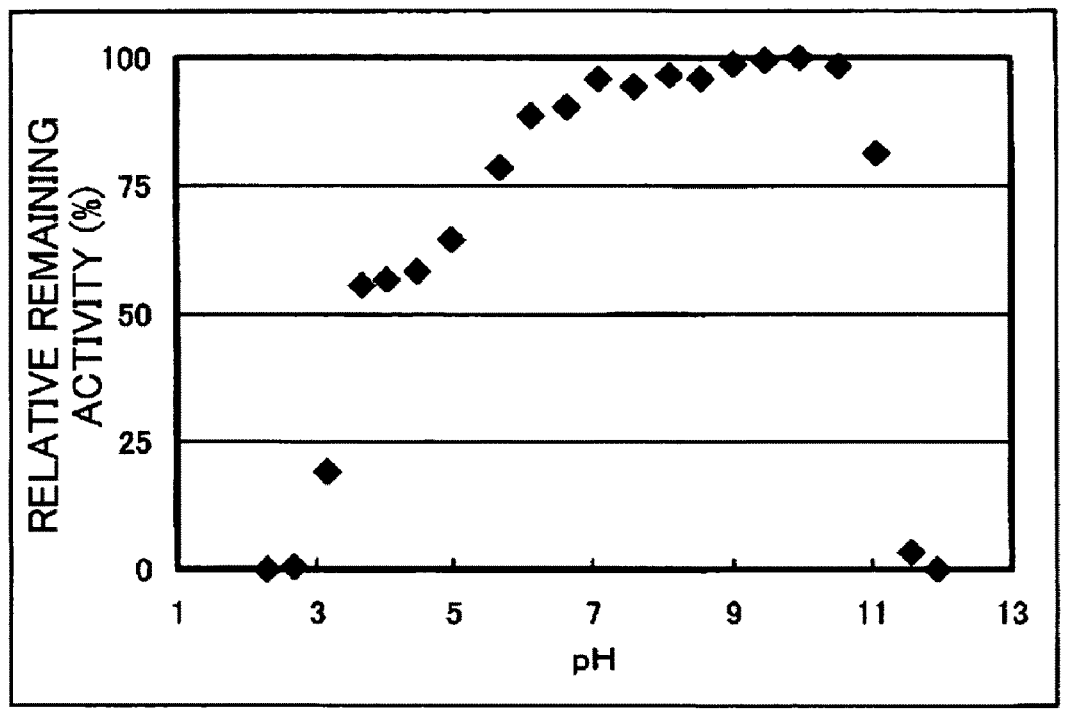
FIG. 5 is a graph showing a result of evaluation on pH stability of mCueO (1) in Test Example 7.
Figure 6:
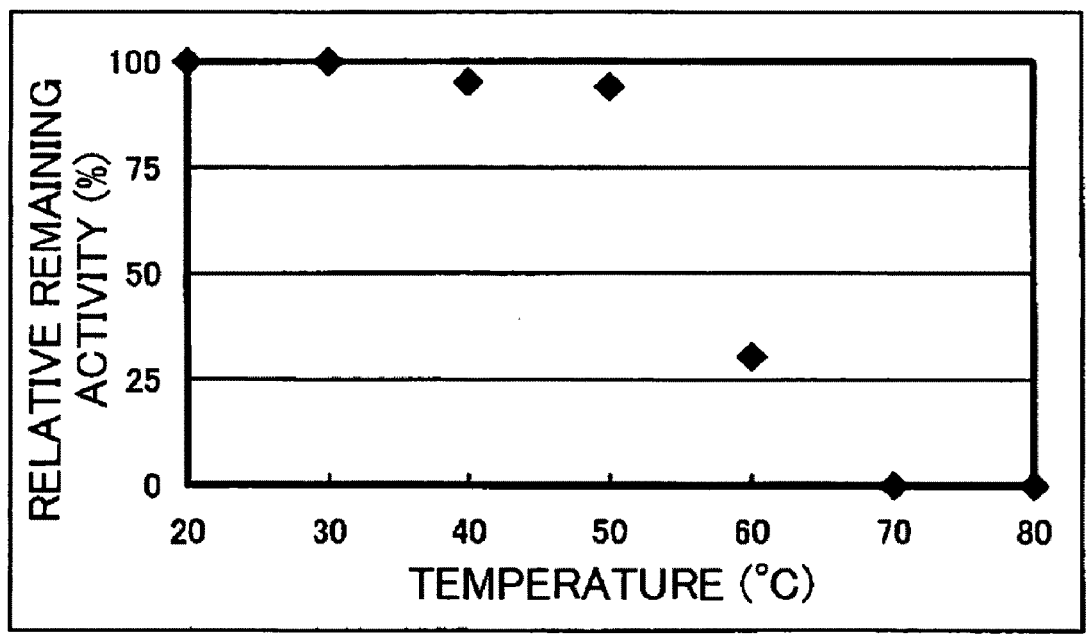
FIG. 6 is a graph showing a result of evaluation on thermal stability of mCueO (1) in Test Example 8.
Figure 7:
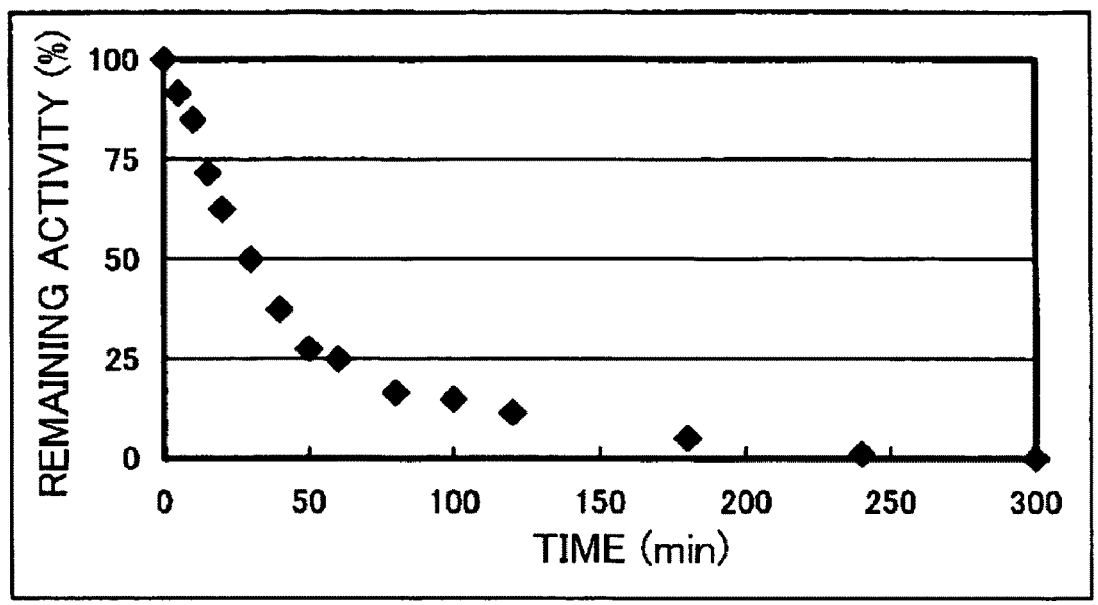
FIG. 7 is a graph showing a result of evaluation on change in thermal stability of mCueO (1) with time in Test Example 9.
Figure 8:
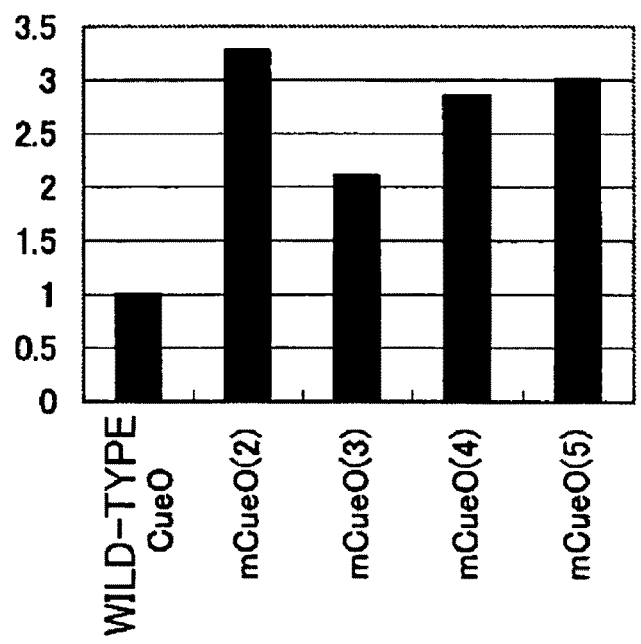
FIG. 8 is a graph showing a result of comparing oxidative polymerization activities of wild-type CueO and mCueO (2) to (5) for PPD in Test Example 10.
Figure 9:
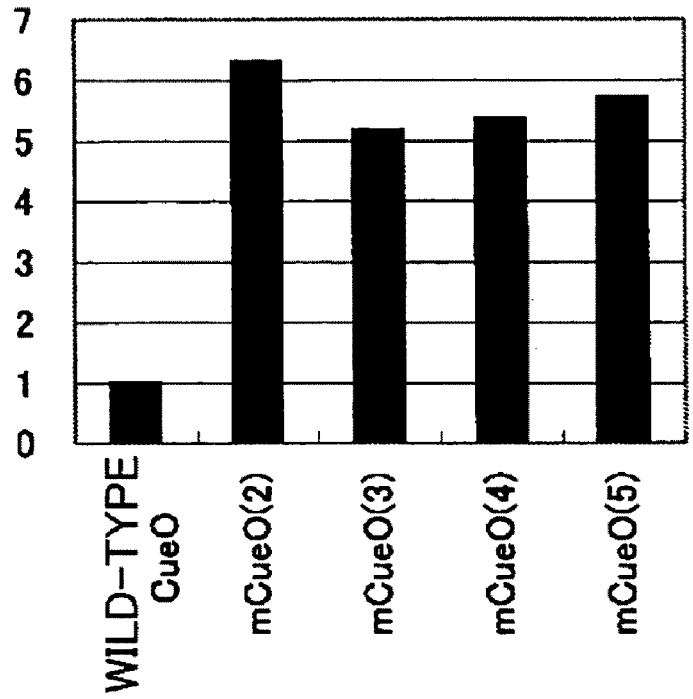
FIG. 9 is a graph showing a result of comparing oxidative polymerization activities of wild-type CueO and mCueO (2) to (5) for OAP in Test Example 10.
Figure 10:
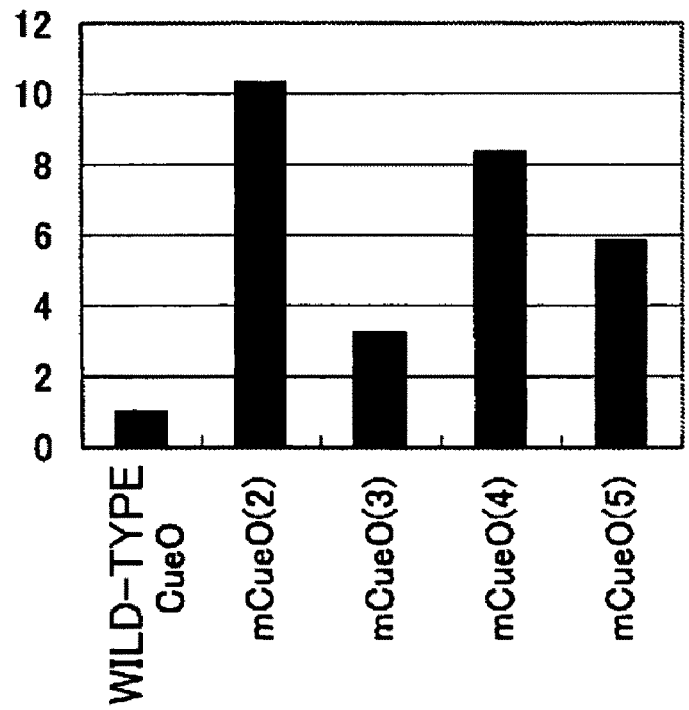
FIG. 10 is a graph showing a result of comparing oxidative polymerization activities of wild-type CueO and mCueO (2) to (5) for ABTS in Test Example 10.

1: Type I Copper
5: Helix 5
6: Helix 6
7: Helix 7

(Sequence Listing Free Text)
SEQ ID NO: 1
Amino acid sequence of wild-type CueO (immature type) derived from *Escherichia coli*
SEQ ID NO: 2
Amino acid sequence of wild-type CueO (mature type) derived from *Escherichia coli*
SEQ ID NO: 3
Amino acid sequence of mCueO (1):CueO(Δα5-7) which is one embodiment of the invention
SEQ ID NO: 4
Amino acid sequence of mCueO (1) (mature type)
SEQ ID NO: 5
Amino acid sequence of mCueO (1) (mature type, a histidine tag is added)
SEQ ID NO: 6
Base sequence coding for amino acid sequence of SEQ ID NO: 4
SEQ ID NO: 7
Base sequence coding for amino acid sequence of SEQ ID NO: 5
SEQ ID NO: 8
Amino acid sequence of wild-type CueO (mature type, a histidine tag is added) derived from *Escherichia coli*
SEQ ID NOS: 9 and 10
Primers used in Reference Production Example 1

SEQ ID NOS: 11 and 12
Primers used in Example 1
SEQ ID NO: 13
Amino acid sequence removed from wild-type CueO derived from *Escherichia coli* to prepare mCueO (1)
SEQ ID NO: 14
Base sequence coding for mCueO (2):CueO(Δα5-7)' (immature type, a histidine tag is added) which is another embodiment of the invention
SEQ ID NO 15:
Amino acid sequence encoded by the base sequence of SEQ ID NO: 14
SEQ ID NOS: 16 and 17
Primers used in Example 6
SEQ ID NO: 18
Base sequence inserted for preparing mCueO (3):CueO (Δα6-7) which is another embodiment of the invention
SEQ ID NO: 19
Amino acid sequence encoded by the base sequence of SEQ ID NO: 18
SEQ ID NO: 20
Base sequence coding for mCueO (3) (immature type, a histidine tag is added)
SEQ ID NO: 21
Amino acid sequence encoded by the base sequence of SEQ ID NO: 20
SEQ ID NOS: 22 and 23
Primers used in Example 7
SEQ ID NO: 24
Base sequence inserted for preparing mCueO (4):CueO (Δα5) which is another embodiment of the invention
SEQ ID NO: 25
Amino acid sequence encoded by the base sequence of SEQ ID NO: 24
SEQ ID NO: 26
Base sequence coding for mCueO (4) (immature type, a histidine tag is added)
SEQ ID NO: 27
Amino acid sequence encoded by the base sequence of SEQ ID NO: 26
SEQ ID NOS: 28 and 29
Primers used in Example 8
SEQ ID NO: 30
Base sequence inserted for preparing mCueO (5):CueO (Δα5-7)'+½α5 which is another embodiment of the invention
SEQ ID NO: 31
Amino acid sequence encoded by the base sequence of SEQ ID NO: 30
SEQ ID NO: 32
Base sequence coding for mCueO (5) (immature type, a histidine tag is added)
SEQ ID NO: 33
Amino acid sequence encoded by the base sequence of SEQ ID NO: 32
SEQ ID NOS: 34 and 35
Primers used in Example 9
SEQ ID NO: 36
Amino acid sequence of mCueO (2) (mature type)
SEQ ID NO: 37
Amino acid sequence of mCueO (3) (mature type)
SEQ ID NO: 38
Amino acid sequence of mCueO (4) (mature type)
SEQ ID NO: 39
Amino acid sequence of mCueO (5) (mature type)
SEQ ID NO: 40
Base sequence coding for mCueO (1) (immature type, a histidine tag is added)
SEQ ID NO: 41
Amino acid sequence encoded by the base sequence of SEQ ID NO: 40

The invention claimed is:

1. An isolated recombinant protein having an enzymatic activity for oxidizing p-phenylenediamine, the protein is obtained by removing from *Escherichia coli* multi-copper oxidase (CueO) of SEQ ID NO: 2 at least one member selected from the group consisting of helix 5, helix 6, and helix 7,
- wherein helix 5 is formed from amino acid residues 329-344 of SEQ ID NO: 2,
- wherein helix 6 is formed from amino acid residues 345-349 of SEQ ID NO: 2, and
- wherein helix 7 is formed from amino acid residues 375-378 of SEQ ID NO: 2.

2. The recombinant protein according to claim 1, which is obtained by removing at the least helix 5 from CueO.

3. The recombinant protein according to claim 1, which is obtained by removing helix 5, helix 6, and helix 7, from CueO, and instead inserting a spacer thereinto.

4. The recombinant protein according to claim 3, which comprises an amino acid sequence of SEQ ID NO: 4.

5. An isolated gene encoding the recombinant protein of claim 1.

6. A recombinant vector comprising the gene of claim 5.

7. A transformant comprising the recombinant vector of claim 6.

8. The transformant according to claim 7, wherein Deposit Number is PERM BP-10431.

9. A process for producing a recombinant Cueo protein comprising culturing the transformant of claim 7, and collecting the produced recombinant Cueo protein.

10. A composition for dyeing keratin fiber, comprising the recombinant protein of claim 1 and an oxidizible dye.

11. The composition for dyeing keratin fiber according to claim 10, further comprising an alkaline compound.

12. The composition for dyeing keratin fiber according to claim 10, wherein the keratin fiber is hair.

13. A method of dyeing keratin fiber, comprising
- bringing keratin fiber into contact with an oxidizable dye in the presence of the recombinant protein of claim 1 under an oxygen-containing atmosphere.

14. The dyeing method according to claim 13, wherein the contacting process is carried out under an alkaline condition.

* * * * *

SEQUENCE LISTING

```
<160> NUMBER OF SEQ ID NOS: 43

<210> SEQ ID NO 1
<211> LENGTH: 516
<212> TYPE: PRT
<213> ORGANISM: Escherichia coli

<400> SEQUENCE: 1

Met Gln Arg Arg Asp Phe Leu Lys Tyr Ser Val Ala Leu Gly Val Ala
1               5                   10                  15

Ser Ala Leu Pro Leu Trp Ser Arg Ala Val Phe Ala Ala Glu Arg Pro
            20                  25                  30

Thr Leu Pro Ile Pro Asp Leu Leu Thr Thr Asp Ala Arg Asn Arg Ile
        35                  40                  45

Gln Leu Thr Ile Gly Ala Gly Gln Ser Thr Phe Gly Gly Lys Thr Ala
    50                  55                  60

Thr Thr Trp Gly Tyr Asn Gly Asn Leu Leu Gly Pro Ala Val Lys Leu
65                  70                  75                  80

Gln Arg Gly Lys Ala Val Thr Val Asp Ile Tyr Asn Gln Leu Thr Glu
            85                  90                  95

Glu Thr Thr Leu His Trp His Gly Leu Glu Val Pro Gly Glu Val Asp
            100                 105                 110

Gly Gly Pro Gln Gly Ile Ile Pro Pro Gly Gly Lys Arg Ser Val Thr
        115                 120                 125
```

Leu Asn Val Asp Gln Pro Ala Ala Thr Cys Trp Phe His Pro His Gln
130                 135                 140

His Gly Lys Thr Gly Arg Gln Val Ala Met Gly Leu Ala Gly Leu Val
145                 150                 155                 160

Val Ile Glu Asp Asp Glu Ile Leu Lys Leu Met Leu Pro Lys Gln Trp
                165                 170                 175

Gly Ile Asp Asp Val Pro Val Ile Val Gln Asp Lys Lys Phe Ser Ala
                180                 185                 190

Asp Gly Gln Ile Asp Tyr Gln Leu Asp Val Met Thr Ala Ala Val Gly
                195                 200                 205

Trp Phe Gly Asp Thr Leu Leu Thr Asn Gly Ala Ile Tyr Pro Gln His
210                 215                 220

Ala Ala Pro Arg Gly Trp Leu Arg Leu Arg Leu Leu Asn Gly Cys Asn
225                 230                 235                 240

Ala Arg Ser Leu Asn Phe Ala Thr Ser Asp Asn Arg Pro Leu Tyr Val
                245                 250                 255

Ile Ala Ser Asp Gly Gly Leu Leu Pro Glu Pro Val Lys Val Ser Glu
                260                 265                 270

Leu Pro Val Leu Met Gly Glu Arg Phe Glu Val Leu Glu Val Asn
                275                 280                 285

Asp Asn Lys Pro Phe Asp Leu Val Thr Leu Pro Val Ser Gln Met Gly
290                 295                 300

Met Ala Ile Ala Pro Phe Asp Lys Pro His Pro Val Met Arg Ile Gln
305                 310                 315                 320

Pro Ile Ala Ile Ser Ala Ser Gly Ala Leu Pro Asp Thr Leu Ser Ser
                325                 330                 335

Leu Pro Ala Leu Pro Ser Leu Glu Gly Leu Thr Val Arg Lys Leu Gln
                340                 345                 350

Leu Ser Met Asp Pro Met Leu Asp Met Met Gly Met Gln Met Leu Met
                355                 360                 365

Glu Lys Tyr Gly Asp Gln Ala Met Ala Gly Met Asp His Ser Gln Met
                370                 375                 380

Met Gly His Met Gly His Gly Asn Met Asn His Met Asn His Gly Gly
385                 390                 395                 400

Lys Phe Asp Phe His His Ala Asn Lys Ile Asn Gly Gln Ala Phe Asp
                405                 410                 415

Met Asn Lys Pro Met Phe Ala Ala Lys Gly Gln Tyr Glu Arg Trp
                420                 425                 430

Val Ile Ser Gly Val Gly Asp Met Met Leu His Pro Phe His Ile His
                435                 440                 445

Gly Thr Gln Phe Arg Ile Leu Ser Glu Asn Gly Lys Pro Pro Ala Ala
                450                 455                 460

His Arg Ala Gly Trp Lys Asp Thr Val Lys Val Glu Gly Asn Val Ser
465                 470                 475                 480

Glu Val Leu Val Lys Phe Asn His Asp Ala Pro Lys Glu His Ala Tyr
                485                 490                 495

Met Ala His Cys His Leu Leu Glu His Glu Asp Thr Gly Met Met Leu
                500                 505                 510

Gly Phe Thr Val
                515

<210> SEQ ID NO 2
<211> LENGTH: 488
<212> TYPE: PRT

<213> ORGANISM: Escherichia coli

<400> SEQUENCE: 2

```
Ala Glu Arg Pro Thr Leu Pro Ile Pro Asp Leu Leu Thr Thr Asp Ala
1               5                   10                  15

Arg Asn Arg Ile Gln Leu Thr Ile Gly Ala Gly Gln Ser Thr Phe Gly
            20                  25                  30

Gly Lys Thr Ala Thr Thr Trp Gly Tyr Asn Gly Asn Leu Leu Gly Pro
        35                  40                  45

Ala Val Lys Leu Gln Arg Gly Lys Ala Val Thr Val Asp Ile Tyr Asn
50                  55                  60

Gln Leu Thr Glu Glu Thr Thr Leu His Trp His Gly Leu Glu Val Pro
65                  70                  75                  80

Gly Glu Val Asp Gly Gly Pro Gln Gly Ile Ile Pro Pro Gly Gly Lys
                85                  90                  95

Arg Ser Val Thr Leu Asn Val Asp Gln Pro Ala Ala Thr Cys Trp Phe
            100                 105                 110

His Pro His Gln His Gly Lys Thr Gly Arg Gln Val Ala Met Gly Leu
        115                 120                 125

Ala Gly Leu Val Val Ile Glu Asp Asp Glu Ile Leu Lys Leu Met Leu
130                 135                 140

Pro Lys Gln Trp Gly Ile Asp Asp Val Pro Val Ile Val Gln Asp Lys
145                 150                 155                 160

Lys Phe Ser Ala Asp Gly Gln Ile Asp Tyr Gln Leu Asp Val Met Thr
                165                 170                 175

Ala Ala Val Gly Trp Phe Gly Asp Thr Leu Leu Thr Asn Gly Ala Ile
            180                 185                 190

Tyr Pro Gln His Ala Ala Pro Arg Gly Trp Leu Arg Leu Arg Leu Leu
        195                 200                 205

Asn Gly Cys Asn Ala Arg Ser Leu Asn Phe Ala Thr Ser Asp Asn Arg
210                 215                 220

Pro Leu Tyr Val Ile Ala Ser Asp Gly Gly Leu Leu Pro Glu Pro Val
225                 230                 235                 240

Lys Val Ser Glu Leu Pro Val Leu Met Gly Glu Arg Phe Glu Val Leu
                245                 250                 255

Val Glu Val Asn Asp Asn Lys Pro Phe Asp Leu Val Thr Leu Pro Val
            260                 265                 270

Ser Gln Met Gly Met Ala Ile Ala Pro Phe Asp Lys Pro His Pro Val
        275                 280                 285

Met Arg Ile Gln Pro Ile Ala Ile Ser Ala Ser Gly Ala Leu Pro Asp
290                 295                 300

Thr Leu Ser Ser Leu Pro Ala Leu Pro Ser Leu Glu Gly Leu Thr Val
305                 310                 315                 320

Arg Lys Leu Gln Leu Ser Met Asp Pro Met Leu Asp Met Met Gly Met
                325                 330                 335

Gln Met Leu Met Glu Lys Tyr Gly Asp Gln Ala Met Ala Gly Met Asp
            340                 345                 350

His Ser Gln Met Met Gly His Met Gly His Gly Asn Met Asn His Met
        355                 360                 365

Asn His Gly Gly Lys Phe Asp Phe His His Ala Asn Lys Ile Asn Gly
370                 375                 380

Gln Ala Phe Asp Met Asn Lys Pro Met Phe Ala Ala Lys Gly Gln
385                 390                 395                 400

Tyr Glu Arg Trp Val Ile Ser Gly Val Gly Asp Met Met Leu His Pro
```

```
                    405                 410                 415
Phe His Ile His Gly Thr Gln Phe Arg Ile Leu Ser Glu Asn Gly Lys
            420                 425                 430

Pro Pro Ala Ala His Arg Ala Gly Trp Lys Asp Thr Val Lys Val Glu
            435                 440                 445

Gly Asn Val Ser Glu Val Leu Val Lys Phe Asn His Asp Ala Pro Lys
            450                 455                 460

Glu His Ala Tyr Met Ala His Cys His Leu Leu Glu His Glu Asp Thr
465                 470                 475                 480

Gly Met Met Leu Gly Phe Thr Val
                485

<210> SEQ ID NO 3
<211> LENGTH: 468
<212> TYPE: PRT
<213> ORGANISM: Artificial Sequence
<220> FEATURE:
<223> OTHER INFORMATION: Synthetic amino acid: premature mCueO (1)

<400> SEQUENCE: 3

Met Gln Arg Arg Asp Phe Leu Lys Tyr Ser Val Ala Leu Gly Val Ala
1               5                   10                  15

Ser Ala Leu Pro Leu Trp Ser Arg Ala Val Phe Ala Ala Glu Arg Pro
            20                  25                  30

Thr Leu Pro Ile Pro Asp Leu Leu Thr Thr Asp Ala Arg Asn Arg Ile
        35                  40                  45

Gln Leu Thr Ile Gly Ala Gly Gln Ser Thr Phe Gly Gly Lys Thr Ala
    50                  55                  60

Thr Thr Trp Gly Tyr Asn Gly Asn Leu Leu Gly Pro Ala Val Lys Leu
65                  70                  75                  80

Gln Arg Gly Lys Ala Val Thr Val Asp Ile Tyr Asn Gln Leu Thr Glu
            85                  90                  95

Glu Thr Thr Leu His Trp His Gly Leu Glu Val Pro Gly Glu Val Asp
            100                 105                 110

Gly Gly Pro Gln Gly Ile Ile Pro Pro Gly Gly Lys Arg Ser Val Thr
        115                 120                 125

Leu Asn Val Asp Gln Pro Ala Ala Thr Cys Trp Phe His Pro His Gln
    130                 135                 140

His Gly Lys Thr Gly Arg Gln Val Ala Met Gly Leu Ala Gly Leu Val
145                 150                 155                 160

Val Ile Glu Asp Asp Glu Ile Leu Lys Leu Met Leu Pro Lys Gln Trp
            165                 170                 175

Gly Ile Asp Asp Val Pro Val Ile Val Gln Asp Lys Lys Phe Ser Ala
            180                 185                 190

Asp Gly Gln Ile Asp Tyr Gln Leu Asp Val Met Thr Ala Ala Val Gly
        195                 200                 205

Trp Phe Gly Asp Thr Leu Leu Thr Asn Gly Ala Ile Tyr Pro Gln His
    210                 215                 220

Ala Ala Pro Arg Gly Trp Leu Arg Leu Arg Leu Leu Asn Gly Cys Asn
225                 230                 235                 240

Ala Arg Ser Leu Asn Phe Ala Thr Ser Asp Asn Arg Pro Leu Tyr Val
            245                 250                 255

Ile Ala Ser Asp Gly Gly Leu Leu Pro Glu Pro Val Lys Val Ser Glu
            260                 265                 270

Leu Pro Val Leu Met Gly Glu Arg Phe Glu Val Leu Val Glu Val Asn
        275                 280                 285
```

```
Asp Asn Lys Pro Phe Asp Leu Val Thr Leu Pro Val Ser Gln Met Gly
        290                 295                 300
Met Ala Ile Ala Pro Phe Asp Lys Pro His Pro Val Met Arg Ile Gln
305                 310                 315                 320
Pro Ile Ala Ile Ser Ala Ser Gly Ala Leu Pro Asp Thr Leu Ser Ser
                325                 330                 335
Leu Pro Ala Leu Pro Ser Leu Glu Gly Leu Thr Val Arg Lys Leu Gln
            340                 345                 350
Leu Ser Met Asp Gly Gly Ala Asn Lys Ile Asn Gly Gln Ala Phe Asp
        355                 360                 365
Met Asn Lys Pro Met Phe Ala Ala Lys Gly Gln Tyr Glu Arg Trp
370                 375                 380
Val Ile Ser Gly Val Gly Asp Met Met Leu His Pro Phe His Ile His
385                 390                 395                 400
Gly Thr Gln Phe Arg Ile Leu Ser Glu Asn Gly Lys Pro Pro Ala Ala
                405                 410                 415
His Arg Ala Gly Trp Lys Asp Thr Val Lys Val Glu Gly Asn Val Ser
            420                 425                 430
Glu Val Leu Val Lys Phe Asn His Asp Ala Pro Lys Glu His Ala Tyr
        435                 440                 445
Met Ala His Cys His Leu Leu Glu His Glu Asp Thr Gly Met Met Leu
450                 455                 460
Gly Phe Thr Val
465

<210> SEQ ID NO 4
<211> LENGTH: 440
<212> TYPE: PRT
<213> ORGANISM: Artificial Sequence
<220> FEATURE:
<223> OTHER INFORMATION: Synthetic amino acid: mature mCueO (1)

<400> SEQUENCE: 4

Ala Glu Arg Pro Thr Leu Pro Ile Pro Asp Leu Leu Thr Thr Asp Ala
1               5                   10                  15
Arg Asn Arg Ile Gln Leu Thr Ile Gly Ala Gly Gln Ser Thr Phe Gly
            20                  25                  30
Gly Lys Thr Ala Thr Thr Trp Gly Tyr Asn Gly Asn Leu Leu Gly Pro
        35                  40                  45
Ala Val Lys Leu Gln Arg Gly Lys Ala Val Thr Val Asp Ile Tyr Asn
    50                  55                  60
Gln Leu Thr Glu Glu Thr Thr Leu His Trp His Gly Leu Glu Val Pro
65                  70                  75                  80
Gly Glu Val Asp Gly Gly Pro Gln Gly Ile Ile Pro Pro Gly Gly Lys
                85                  90                  95
Arg Ser Val Thr Leu Asn Val Asp Gln Pro Ala Ala Thr Cys Trp Phe
            100                 105                 110
His Pro His Gln His Gly Lys Thr Gly Arg Gln Val Ala Met Gly Leu
        115                 120                 125
Ala Gly Leu Val Val Ile Glu Asp Asp Glu Ile Leu Lys Leu Met Leu
    130                 135                 140
Pro Lys Gln Trp Gly Ile Asp Asp Val Pro Val Ile Val Gln Asp Lys
145                 150                 155                 160
Lys Phe Ser Ala Asp Gly Gln Ile Asp Tyr Gln Leu Asp Val Met Thr
                165                 170                 175
```

-continued

```
Ala Ala Val Gly Trp Phe Gly Asp Thr Leu Leu Thr Asn Gly Ala Ile
            180                 185                 190

Tyr Pro Gln His Ala Ala Pro Arg Gly Trp Leu Arg Leu Arg Leu Leu
        195                 200                 205

Asn Gly Cys Asn Ala Arg Ser Leu Asn Phe Ala Thr Ser Asp Asn Arg
    210                 215                 220

Pro Leu Tyr Val Ile Ala Ser Asp Gly Leu Leu Pro Glu Pro Val
225                 230                 235                 240

Lys Val Ser Glu Leu Pro Val Leu Met Gly Glu Arg Phe Glu Val Leu
                245                 250                 255

Val Glu Val Asn Asp Asn Lys Pro Phe Asp Leu Val Thr Leu Pro Val
            260                 265                 270

Ser Gln Met Gly Met Ala Ile Ala Pro Phe Asp Lys Pro His Pro Val
        275                 280                 285

Met Arg Ile Gln Pro Ile Ala Ile Ser Ala Ser Gly Ala Leu Pro Asp
    290                 295                 300

Thr Leu Ser Ser Leu Pro Ala Leu Pro Ser Leu Glu Gly Leu Thr Val
305                 310                 315                 320

Arg Lys Leu Gln Leu Ser Met Asp Gly Gly Ala Asn Lys Ile Asn Gly
                325                 330                 335

Gln Ala Phe Asp Met Asn Lys Pro Met Phe Ala Ala Lys Gly Gln
            340                 345                 350

Tyr Glu Arg Trp Val Ile Ser Gly Val Gly Asp Met Met Leu His Pro
        355                 360                 365

Phe His Ile His Gly Thr Gln Phe Arg Ile Leu Ser Glu Asn Gly Lys
    370                 375                 380

Pro Pro Ala Ala His Arg Ala Gly Trp Lys Asp Thr Val Lys Val Glu
385                 390                 395                 400

Gly Asn Val Ser Glu Val Leu Val Lys Phe Asn His Asp Ala Pro Lys
                405                 410                 415

Glu His Ala Tyr Met Ala His Cys His Leu Leu Glu His Glu Asp Thr
            420                 425                 430

Gly Met Met Leu Gly Phe Thr Val
        435                 440
```

<210> SEQ ID NO 5
<211> LENGTH: 447
<212> TYPE: PRT
<213> ORGANISM: Artificial Sequence
<220> FEATURE:
<223> OTHER INFORMATION: Synthetic amino acid: mature mCueO (1), His-Tag
    added

<400> SEQUENCE: 5

```
Ala Glu Arg Pro Thr Leu Pro Ile Pro Asp Leu Leu Thr Thr Asp Ala
1               5                   10                  15

Arg Asn Arg Ile Gln Leu Thr Ile Gly Ala Gly Gln Ser Thr Phe Gly
                20                  25                  30

Gly Lys Thr Ala Thr Thr Trp Gly Tyr Asn Gly Asn Leu Leu Gly Pro
            35                  40                  45

Ala Val Lys Leu Gln Arg Gly Lys Ala Val Thr Val Asp Ile Tyr Asn
        50                  55                  60

Gln Leu Thr Glu Glu Thr Thr Leu His Trp His Gly Leu Glu Val Pro
65                  70                  75                  80

Gly Glu Val Asp Gly Gly Pro Gln Gly Ile Ile Pro Pro Gly Gly Lys
                85                  90                  95
```

-continued

Arg Ser Val Thr Leu Asn Val Asp Gln Pro Ala Ala Thr Cys Trp Phe
            100                 105                 110
His Pro His Gln His Gly Lys Thr Gly Arg Gln Val Ala Met Gly Leu
        115                 120                 125
Ala Gly Leu Val Val Ile Glu Asp Asp Glu Ile Leu Lys Leu Met Leu
    130                 135                 140
Pro Lys Gln Trp Gly Ile Asp Asp Val Pro Val Ile Val Gln Asp Lys
145                 150                 155                 160
Lys Phe Ser Ala Asp Gly Gln Ile Asp Tyr Gln Leu Asp Val Met Thr
                165                 170                 175
Ala Ala Val Gly Trp Phe Gly Asp Thr Leu Leu Thr Asn Gly Ala Ile
            180                 185                 190
Tyr Pro Gln His Ala Ala Pro Arg Gly Trp Leu Arg Leu Arg Leu Leu
        195                 200                 205
Asn Gly Cys Asn Ala Arg Ser Leu Asn Phe Ala Thr Ser Asp Asn Arg
    210                 215                 220
Pro Leu Tyr Val Ile Ala Ser Asp Gly Gly Leu Leu Pro Glu Pro Val
225                 230                 235                 240
Lys Val Ser Glu Leu Pro Val Leu Met Gly Glu Arg Phe Glu Val Leu
                245                 250                 255
Val Glu Val Asn Asp Asn Lys Pro Phe Asp Leu Val Thr Leu Pro Val
            260                 265                 270
Ser Gln Met Gly Met Ala Ile Ala Pro Phe Asp Lys Pro His Pro Val
        275                 280                 285
Met Arg Ile Gln Pro Ile Ala Ile Ser Ala Ser Gly Ala Leu Pro Asp
    290                 295                 300
Thr Leu Ser Ser Leu Pro Ala Leu Pro Ser Leu Glu Gly Leu Thr Val
305                 310                 315                 320
Arg Lys Leu Gln Leu Ser Met Asp Gly Gly Ala Asn Lys Ile Asn Gly
                325                 330                 335
Gln Ala Phe Asp Met Asn Lys Pro Met Phe Ala Ala Ala Lys Gly Gln
            340                 345                 350
Tyr Glu Arg Trp Val Ile Ser Gly Val Gly Asp Met Met Leu His Pro
        355                 360                 365
Phe His Ile His Gly Thr Gln Phe Arg Ile Leu Ser Glu Asn Gly Lys
    370                 375                 380
Pro Pro Ala Ala His Arg Ala Gly Trp Lys Asp Thr Val Lys Val Glu
385                 390                 395                 400
Gly Asn Val Ser Glu Val Leu Val Lys Phe Asn His Asp Ala Pro Lys
                405                 410                 415
Glu His Ala Tyr Met Ala His Cys His Leu Leu Glu His Glu Asp Thr
            420                 425                 430
Gly Met Met Leu Gly Phe Thr Val Gly His His His His His His
        435                 440                 445

<210> SEQ ID NO 6
<211> LENGTH: 1323
<212> TYPE: DNA
<213> ORGANISM: Artificial Sequence
<220> FEATURE:
<223> OTHER INFORMATION: Synthetic DNA: mature mCueO (1)

<400> SEQUENCE: 6
gcagaacgcc caacgttacc gatccctgat tgctcacga ccgatgcccg taatcgcatt      60
cagttaacta ttggcgcagg ccagtccacc tttggcggga aaactgcaac tacctggggc     120

| | |
|---|---|
| tataacggca atctgctggg gccggcggtg aaattacagc gcggcaaagc ggtaacggtt | 180 |
| gatatctaca accaactgac ggaagagaca acgttgcact ggcacgggct ggaagtaccg | 240 |
| ggtgaagtcg acggcggccc gcagggaatt attccgccag gtggcaagcg ctcggtgacg | 300 |
| ttgaacgttg atcaacctgc cgctacctgc tggttccatc cgcatcagca cggcaaaacc | 360 |
| gggcgacagg tggcgatggg gctggctggg ctggtggtga ttgaagatga cgagatcctg | 420 |
| aaattaatgc tgccaaaaca gtggggtatc gatgatgttc cggtgatcgt tcaggataag | 480 |
| aaatttagcg ccgacgggca gattgattat caactggatg tgatgaccgc cgccgtgggc | 540 |
| tggtttggcg atacgttgct gaccaacggt gcaatctacc cgcaacacgc tgccccgcgt | 600 |
| ggttggctgc gcctgcgttt gctcaatggc tgtaatgccc gttcgctcaa tttcgccacc | 660 |
| agcgacaatc gcccgctgta tgtgattgcc agcgacggtg gtctgctacc tgaaccagtg | 720 |
| aaggtgagcg aactgccggt gctgatgggc gagcgttttg aagtgctggt ggaggttaac | 780 |
| gataacaaac cctttgacct ggtgacgctg ccggtcagcc agatggggat ggcgattgcg | 840 |
| ccgtttgata agcctcatcc ggtaatgcgg attcagccga ttgctattag tgcctccggt | 900 |
| gctttgccag acacattaag tagcctgcct gcgttacctt cgctggaagg gctgacggta | 960 |
| cgcaagctgc aactctctat ggacggtggt gccaacaaaa tcaacggtca ggcgtttgat | 1020 |
| atgaacaagc cgatgtttgc ggcggcgaaa gggcaatacg aacgttgggt tatctctggc | 1080 |
| gtgggcgaca tgatgctgca tccgttccat atccacggca cgcagttccg tatcttgtca | 1140 |
| gaaaatggca aaccgccagc ggctcatcgc gcgggctgga agataccgt taaggtagaa | 1200 |
| ggtaatgtca gcgaagtgct ggtgaagttt aatcacgatg caccgaaaga acatgcttat | 1260 |
| atggcgcact gccatctgct ggagcatgaa gatacgggga tgatgttagg gtttacggta | 1320 |
| taa | 1323 |

<210> SEQ ID NO 7
<211> LENGTH: 1344
<212> TYPE: DNA
<213> ORGANISM: Artificial Sequence
<220> FEATURE:
<223> OTHER INFORMATION: Synthetic DNA: mature mCueO (1), His-Tag added

<400> SEQUENCE: 7

| | |
|---|---|
| gcagaacgcc caacgttacc gatccctgat ttgctcacga ccgatgcccg taatcgcatt | 60 |
| cagttaacta ttggcgcagg ccagtccacc tttggcggga aaactgcaac tacctggggc | 120 |
| tataacggca atctgctggg gccggcggtg aaattacagc gcggcaaagc ggtaacggtt | 180 |
| gatatctaca accaactgac ggaagagaca acgttgcact ggcacgggct ggaagtaccg | 240 |
| ggtgaagtcg acggcggccc gcagggaatt attccgccag gtggcaagcg ctcggtgacg | 300 |
| ttgaacgttg atcaacctgc cgctacctgc tggttccatc cgcatcagca cggcaaaacc | 360 |
| gggcgacagg tggcgatggg gctggctggg ctggtggtga ttgaagatga cgagatcctg | 420 |
| aaattaatgc tgccaaaaca gtggggtatc gatgatgttc cggtgatcgt tcaggataag | 480 |
| aaatttagcg ccgacgggca gattgattat caactggatg tgatgaccgc cgccgtgggc | 540 |
| tggtttggcg atacgttgct gaccaacggt gcaatctacc cgcaacacgc tgccccgcgt | 600 |
| ggttggctgc gcctgcgttt gctcaatggc tgtaatgccc gttcgctcaa tttcgccacc | 660 |
| agcgacaatc gcccgctgta tgtgattgcc agcgacggtg gtctgctacc tgaaccagtg | 720 |
| aaggtgagcg aactgccggt gctgatgggc gagcgttttg aagtgctggt ggaggttaac | 780 |
| gataacaaac cctttgacct ggtgacgctg ccggtcagcc agatggggat ggcgattgcg | 840 |

```
ccgtttgata agcctcatcc ggtaatgcgg attcagccga ttgctattag tgcctccggt    900
gctttgccag acacattaag tagcctgcct gcgttacctt cgctggaagg gctgacggta    960
cgcaagctgc aactctctat ggacggtggt gccaacaaaa tcaacggtca ggcgtttgat   1020
atgaacaagc cgatgtttgc ggcggcgaaa gggcaatacg aacgttgggt tatctctggc   1080
gtgggcgaca tgatgctgca tccgttccat atccacggca cgcagttccg tatcttgtca   1140
gaaaatggca accgccagc ggctcatcgc gcgggctgga agataccgt taaggtagaa    1200 ggtaatgtca gcgaagtgct ggtgaagttt aatcacgatg caccgaaaga acatgcttat   1260
atggcgcact gccatctgct ggagcatgaa gatacgggga tgatgttagg gtttacggta   1320
ggccatcatc atcatcatca ttaa                                          1344
```

<210> SEQ ID NO 8
<211> LENGTH: 495
<212> TYPE: PRT
<213> ORGANISM: Artificial Sequence
<220> FEATURE:
<223> OTHER INFORMATION: Synthetic amino acid: mature CueO, His-Tag added

<400> SEQUENCE: 8

```
Ala Glu Arg Pro Thr Leu Pro Ile Pro Asp Leu Leu Thr Thr Asp Ala
1               5                   10                  15

Arg Asn Arg Ile Gln Leu Thr Ile Gly Ala Gly Gln Ser Thr Phe Gly
            20                  25                  30

Gly Lys Thr Ala Thr Thr Trp Gly Tyr Asn Gly Asn Leu Leu Gly Pro
        35                  40                  45

Ala Val Lys Leu Gln Arg Gly Lys Ala Val Thr Val Asp Ile Tyr Asn
    50                  55                  60

Gln Leu Thr Glu Glu Thr Thr Leu His Trp His Gly Leu Glu Val Pro
65                  70                  75                  80

Gly Glu Val Asp Gly Gly Pro Gln Gly Ile Ile Pro Pro Gly Gly Lys
                85                  90                  95

Arg Ser Val Thr Leu Asn Val Asp Gln Pro Ala Ala Thr Cys Trp Phe
            100                 105                 110

His Pro His Gln His Gly Lys Thr Gly Arg Gln Val Ala Met Gly Leu
        115                 120                 125

Ala Gly Leu Val Val Ile Glu Asp Asp Glu Ile Leu Lys Leu Met Leu
    130                 135                 140

Pro Lys Gln Trp Gly Ile Asp Asp Val Pro Val Ile Val Gln Asp Lys
145                 150                 155                 160

Lys Phe Ser Ala Asp Gly Gln Ile Asp Tyr Gln Leu Asp Val Met Thr
                165                 170                 175

Ala Ala Val Gly Trp Phe Gly Asp Thr Leu Leu Thr Asn Gly Ala Ile
            180                 185                 190

Tyr Pro Gln His Ala Ala Pro Arg Gly Trp Leu Arg Leu Arg Leu Leu
        195                 200                 205

Asn Gly Cys Asn Ala Arg Ser Leu Asn Phe Ala Thr Ser Asp Asn Arg
    210                 215                 220

Pro Leu Tyr Val Ile Ala Ser Asp Gly Gly Leu Leu Pro Glu Pro Val
225                 230                 235                 240

Lys Val Ser Glu Leu Pro Val Leu Met Gly Glu Arg Phe Glu Val Leu
                245                 250                 255

Val Glu Val Asn Asp Asn Lys Pro Phe Asp Leu Val Thr Leu Pro Val
            260                 265                 270
```

Ser Gln Met Gly Met Ala Ile Ala Pro Phe Asp Lys Pro His Pro Val
    275                 280                 285

Met Arg Ile Gln Pro Ile Ala Ile Ser Ala Ser Gly Ala Leu Pro Asp
290                 295                 300

Thr Leu Ser Ser Leu Pro Ala Leu Pro Ser Leu Glu Gly Leu Thr Val
305                 310                 315                 320

Arg Lys Leu Gln Leu Ser Met Asp Pro Met Leu Asp Met Met Gly Met
                325                 330                 335

Gln Met Leu Met Glu Lys Tyr Gly Asp Gln Ala Met Ala Gly Met Asp
            340                 345                 350

His Ser Gln Met Met Gly His Met Gly His Gly Asn Met Asn His Met
        355                 360                 365

Asn His Gly Gly Lys Phe Asp Phe His His Ala Asn Lys Ile Asn Gly
    370                 375                 380

Gln Ala Phe Asp Met Asn Lys Pro Met Phe Ala Ala Lys Gly Gln
385                 390                 395                 400

Tyr Glu Arg Trp Val Ile Ser Gly Val Gly Asp Met Met Leu His Pro
                405                 410                 415

Phe His Ile His Gly Thr Gln Phe Arg Ile Leu Ser Glu Asn Gly Lys
            420                 425                 430

Pro Pro Ala Ala His Arg Ala Gly Trp Lys Asp Thr Val Lys Val Glu
        435                 440                 445

Gly Asn Val Ser Glu Val Leu Val Lys Phe Asn His Asp Ala Pro Lys
    450                 455                 460

Glu His Ala Tyr Met Ala His Cys His Leu Leu Glu His Glu Asp Thr
465                 470                 475                 480

Gly Met Met Leu Gly Phe Thr Val Gly His His His His
                485                 490                 495

<210> SEQ ID NO 9
<211> LENGTH: 34
<212> TYPE: DNA
<213> ORGANISM: Artificial Sequence
<220> FEATURE:
<223> OTHER INFORMATION: Synthetic primer

<400> SEQUENCE: 9
gaagaattca tgcaacgtcg tgatttctta aaat                          34

<210> SEQ ID NO 10
<211> LENGTH: 48
<212> TYPE: DNA
<213> ORGANISM: Artificial Sequence
<220> FEATURE:
<223> OTHER INFORMATION: Synthetic primer

<400> SEQUENCE: 10
ttggatcctt aatgatgatg atgatgatgg cctaccgtaa accctaac           48

<210> SEQ ID NO 11
<211> LENGTH: 39
<212> TYPE: DNA
<213> ORGANISM: Artificial Sequence
<220> FEATURE:
<223> OTHER INFORMATION: Synthetic primer

<400> SEQUENCE: 11
gttggcacca ccgtccatgg aagattgcag cttgcgtac                     39

<210> SEQ ID NO 12

-continued

```
<211> LENGTH: 37
<212> TYPE: DNA
<213> ORGANISM: Artificial Sequence
<220> FEATURE:
<223> OTHER INFORMATION: Synthetic primer

<400> SEQUENCE: 12
ctctccatgg acggtggtgc aacaaaatc aacggtc                              37

<210> SEQ ID NO 13
<211> LENGTH: 50
<212> TYPE: PRT
<213> ORGANISM: Escherichia coli

<400> SEQUENCE: 13

Pro Met Leu Asp Met Met Gly Met Gln Met Leu Met Glu Lys Tyr Gly
 1               5                  10                  15

Asp Gln Ala Met Ala Gly Met Asp His Ser Gln Met Met Gly His Met
             20                  25                  30

Gly His Gly Asn Met Asn His Met Asn His Gly Gly Lys Phe Asp Phe
         35                  40                  45

His His
     50

<210> SEQ ID NO 14
<211> LENGTH: 1428
<212> TYPE: DNA
<213> ORGANISM: Artificial Sequence
<220> FEATURE:
<223> OTHER INFORMATION: Synthetic DNA: premature mCueO (2), His-Tag
      added

<400> SEQUENCE: 14
atgcaacgtc gtgatttctt aaaatattcc gtcgcgctgg gtgtggcttc ggctttgccg       60
ctgtggagcc gcgcagtatt tgcggcagaa cgcccaacgt taccgatccc tgatttgctc      120
acgaccgatg cccgtaatcg cattcagtta actattggcg caggccagtc caccttttgg      180
gggaaaactg caactacctg gggctataac ggcaatctgc tggggccggc ggtgaaatta      240
cagcgcggca aagcggtaac ggttgatatc tacaaccaac tgacggaaga caacgttg       300 cactggcacg gctggaagt accgggtgaa gtcgacggcg gcccgcaggg aattattccg      360
ccaggtggca gcgctcggt gacgttgaac gttgatcaac tgccgctac ctgctggttc      420 catccgcatc agcacggcaa accgggcga caggtggcga tggggctggc tgggctggtg      480
gtgattgaag atgacgagat cctgaaatta atgctgccaa acagtgggg tatcgatgat      540 gttccggtga tcgttcagga taagaaattt agcgccgatg gcagattga ttatcaactg      600 gatgtgatga ccgccgccgt gggctggttt ggcgatacgt tgctgaccaa cggtgcaatc      660
tacccgcaac acgctgcccc gcgtggtgg ctgcgcctgc gttgctcaa tggctgtaat      720 gcccgttcgc tcaatttcgc caccagcgac aatcgcccgc tgtatgtgat tgccagcgac      780
ggtggtctgc tacctgaacc agtgaaggtg agcgaactgc cggtgctgat gggcgagcgt      840
tttgaagtgc tggtggaggt taatgataac aaaccctttg acctggtgac gctgccggtc      900
agccagatgg ggatggcgat tgcgccgttt gataagcctc atccggtaat gcggattcag      960
ccgattgcta ttagtgcctc cggtgctttg ccagacacat taagtagcct gcctgcgtta     1020
ccttcgctgg aagggctgac ggtacgcaag ctgcaactct ccatggacgc ggccgccaac     1080
aaaatcaacg gtcaggcgtt tgatatgaac aagccgatgt ttgcggcggc gaagggcaa      1140 tacgaacgtt gggttatctc tggcgtgggc gacatgatgc tgcatccgtt ccatatccac     1200
```

```
ggcacgcagt tccgtatctt gtcagaaaat ggcaaaccgc cagcggctca tcgcgcgggc   1260
tggaaagata ccgttaaggt agaaggtaat gtcagcgaag tgctggtgaa gtttaatcac   1320
gatgcaccga agaacatgc ttatatggcg cactgccatc tgctggagca tgaagatacg   1380
gggatgatgt tagggtttac ggtaggccat catcatcatc atcattaa                1428
```

<210> SEQ ID NO 15
<211> LENGTH: 475
<212> TYPE: PRT
<213> ORGANISM: Artificial Sequence
<220> FEATURE:
<223> OTHER INFORMATION: Synthetic amino acid: premature mCueO (2),
      His-Tag added

<400> SEQUENCE: 15

```
Met Gln Arg Arg Asp Phe Leu Lys Tyr Ser Val Ala Leu Gly Val Ala
1               5                   10                  15

Ser Ala Leu Pro Leu Trp Ser Arg Ala Val Phe Ala Ala Glu Arg Pro
            20                  25                  30

Thr Leu Pro Ile Pro Asp Leu Leu Thr Thr Asp Ala Arg Asn Arg Ile
        35                  40                  45

Gln Leu Thr Ile Gly Ala Gly Gln Ser Thr Phe Gly Gly Lys Thr Ala
    50                  55                  60

Thr Thr Trp Gly Tyr Asn Gly Asn Leu Leu Gly Pro Ala Val Lys Leu
65                  70                  75                  80

Gln Arg Gly Lys Ala Val Thr Val Asp Ile Tyr Asn Gln Leu Thr Glu
                85                  90                  95

Glu Thr Thr Leu His Trp His Gly Leu Glu Val Pro Gly Glu Val Asp
            100                 105                 110

Gly Gly Pro Gln Gly Ile Ile Pro Pro Gly Gly Lys Arg Ser Val Thr
        115                 120                 125

Leu Asn Val Asp Gln Pro Ala Ala Thr Cys Trp Phe His Pro His Gln
    130                 135                 140

His Gly Lys Thr Gly Arg Gln Val Ala Met Gly Leu Ala Gly Leu Val
145                 150                 155                 160

Val Ile Glu Asp Asp Glu Ile Leu Lys Leu Met Leu Pro Lys Gln Trp
                165                 170                 175

Gly Ile Asp Asp Val Pro Val Ile Val Gln Asp Lys Lys Phe Ser Ala
            180                 185                 190

Asp Gly Gln Ile Asp Tyr Gln Leu Asp Val Met Thr Ala Ala Val Gly
        195                 200                 205

Trp Phe Gly Asp Thr Leu Leu Thr Asn Gly Ala Ile Tyr Pro Gln His
    210                 215                 220

Ala Ala Pro Arg Gly Trp Leu Arg Leu Arg Leu Leu Asn Gly Cys Asn
225                 230                 235                 240

Ala Arg Ser Leu Asn Phe Ala Thr Ser Asp Asn Arg Pro Leu Tyr Val
                245                 250                 255

Ile Ala Ser Asp Gly Gly Leu Leu Pro Glu Pro Val Lys Val Ser Glu
            260                 265                 270

Leu Pro Val Leu Met Gly Glu Arg Phe Glu Val Leu Val Glu Val Asn
        275                 280                 285

Asp Asn Lys Pro Phe Asp Leu Val Thr Leu Pro Val Ser Gln Met Gly
    290                 295                 300

Met Ala Ile Ala Pro Phe Asp Lys Pro His Pro Val Met Arg Ile Gln
305                 310                 315                 320
```

```
Pro Ile Ala Ile Ser Ala Ser Gly Ala Leu Pro Asp Thr Leu Ser Ser
            325                 330                 335

Leu Pro Ala Leu Pro Ser Leu Glu Gly Leu Thr Val Arg Lys Leu Gln
        340                 345                 350

Leu Ser Met Asp Ala Ala Asn Lys Ile Asn Gly Gln Ala Phe Asp
    355                 360                 365

Met Asn Lys Pro Met Phe Ala Ala Lys Gly Gln Tyr Glu Arg Trp
370                 375                 380

Val Ile Ser Gly Val Gly Asp Met Met Leu His Pro Phe His Ile His
385                 390                 395                 400

Gly Thr Gln Phe Arg Ile Leu Ser Glu Asn Gly Lys Pro Pro Ala Ala
                405                 410                 415

His Arg Ala Gly Trp Lys Asp Thr Val Lys Val Glu Gly Asn Val Ser
            420                 425                 430

Glu Val Leu Val Lys Phe Asn His Asp Ala Pro Lys Glu His Ala Tyr
        435                 440                 445

Met Ala His Cys His Leu Leu Glu His Glu Asp Thr Gly Met Met Leu
    450                 455                 460

Gly Phe Thr Val Gly His His His His His His
465                 470                 475

<210> SEQ ID NO 16
<211> LENGTH: 30
<212> TYPE: DNA
<213> ORGANISM: Artificial Sequence
<220> FEATURE:
<223> OTHER INFORMATION: Synthetic primer

<400> SEQUENCE: 16
ctctccatgg acgcggccgc caacaaaatc                                    30

<210> SEQ ID NO 17
<211> LENGTH: 17
<212> TYPE: DNA
<213> ORGANISM: Artificial Sequence
<220> FEATURE:
<223> OTHER INFORMATION: Synthetic primer

<400> SEQUENCE: 17
gttttcccag tcacgac                                                  17

<210> SEQ ID NO 18
<211> LENGTH: 75
<212> TYPE: DNA
<213> ORGANISM: Artificial Sequence
<220> FEATURE:
<223> OTHER INFORMATION: Synthetic DNA: added sequence

<400> SEQUENCE: 18
ccgatgctcg atatgatggg gatgcagatg ctaatggaga aatatggcgc agctggtgct    60
gcaggagctg cggcc                                                    75

<210> SEQ ID NO 19
<211> LENGTH: 25
<212> TYPE: PRT
<213> ORGANISM: Artificial Sequence
<220> FEATURE:
<223> OTHER INFORMATION: Synthetic amino acid: added sequence

<400> SEQUENCE: 19

Pro Met Leu Asp Met Met Gly Met Gln Met Leu Met Glu Lys Tyr Gly
1               5                   10                  15
```

Ala Ala Gly Ala Ala Gly Ala Ala Ala
              20                  25

<210> SEQ ID NO 20
<211> LENGTH: 1497
<212> TYPE: DNA
<213> ORGANISM: Artificial Sequence
<220> FEATURE:
<223> OTHER INFORMATION: Synthetic DNA: premature mCueO (3), His-Tag
      added

<400> SEQUENCE: 20

| | | |
|---|---|---|
| atgcaacgtc gtgatttctt aaaatattcc gtcgcgctgg gtgtggcttc ggctttgccg | 60 |
| ctgtggagcc gcgcagtatt tgcggcagaa cgcccaacgt taccgatccc tgatttgctc | 120 |
| acgaccgatg cccgtaatcg cattcagtta actattggcg caggccagtc cacctttggc | 180 |
| gggaaaactg caactacctg gggctataac ggcaatctgc tggggccggc ggtgaaatta | 240 |
| cagcgcggca aagcggtaac ggttgatatc tacaaccaac tgacggaaga dacaacgttg | 300 |
| cactggcacg gctggaagt accgggtgaa gtcgacggcg gcccgcaggg aattattccg | 360 |
| ccaggtggca agcgctcggt gacgttgaac gttgatcaac tgccgctac ctgctggttc | 420 |
| catccgcatc agcacggcaa aaccgggcga caggtggcga tggggctggc tgggctggtg | 480 |
| gtgattgaag atgacgagat cctgaaatta atgctgccaa acagtggggg tatcgatgat | 540 |
| gttccggtga tcgttcagga taagaaattt agcgccgatg gcagattga ttatcaactg | 600 |
| gatgtgatga ccgccgccgt gggctggttt ggcgatacgt tgctgaccaa cggtgcaatc | 660 |
| tacccgcaac acgctgcccc gcgtggttgg ctgcgcctgc gtttgctcaa tggctgtaat | 720 |
| gcccgttcgc tcaatttcgc caccagcgac aatcgcccgc tgtatgtgat tgccagcgac | 780 |
| ggtggtctgc tacctgaacc agtgaaggtg agcgaactgc cggtgctgat gggcgagcgt | 840 |
| tttgaagtgc tggtggaggt taatgataac aaacccttg acctggtgac gctgccggtc | 900 |
| agccagatgg ggatggcgat tgcgccgttt gataagcctc atccggtaat gcggattcag | 960 |
| ccgattgcta ttagtgcctc cggtgctttg ccagacacat taagtagcct gcctgcgtta | 1020 |
| ccttcgctgg aagggctgac ggtacgcaag ctgcaactct ccatggaccc gatgctcgat | 1080 |
| atgatgggga tgcagatgct aatggagaaa tatggcgcag ctggtgctgc aggagctgcg | 1140 |
| gccgccaaca aaatcaacgg tcaggcgttt gatatgaaca agccgatgtt tgcggcggcg | 1200 |
| aaagggcaat acgaacgttg ggttatctct ggcgtgggcg acatgatgct gcatccgttc | 1260 |
| catatccacg gcacgcagtt ccgtatcttg tcagaaaatg gcaaaccgcc agcggctcat | 1320 |
| cgcgcgggct ggaaagatac cgttaaggta gaaggtaatg tcagcgaagt gctggtgaag | 1380 |
| tttaatcacg atgcaccgaa agaacatgct tatatggcgc actgccatct gctggagcat | 1440 |
| gaagatacgg ggatgatgtt agggtttacg gtaggccatc atcatcatca tcattaa | 1497 |

<210> SEQ ID NO 21
<211> LENGTH: 498
<212> TYPE: PRT
<213> ORGANISM: Artificial Sequence
<220> FEATURE:
<223> OTHER INFORMATION: Synthetic amino acid: premature mCueO (3),
      His-Tag added

<400> SEQUENCE: 21

Met Gln Arg Arg Asp Phe Leu Lys Tyr Ser Val Ala Leu Gly Val Ala
1               5                   10                  15

Ser Ala Leu Pro Leu Trp Ser Arg Ala Val Phe Ala Ala Glu Arg Pro

```
                        20                  25                  30
Thr Leu Pro Ile Pro Asp Leu Leu Thr Thr Asp Ala Arg Asn Arg Ile
             35                  40                  45
Gln Leu Thr Ile Gly Ala Gly Gln Ser Thr Phe Gly Gly Lys Thr Ala
         50                  55                  60
Thr Thr Trp Gly Tyr Asn Gly Asn Leu Leu Gly Pro Ala Val Lys Leu
 65                  70                  75                  80
Gln Arg Gly Lys Ala Val Thr Val Asp Ile Tyr Asn Gln Leu Thr Glu
                 85                  90                  95
Glu Thr Thr Leu His Trp His Gly Leu Glu Val Pro Gly Glu Val Asp
                100                 105                 110
Gly Gly Pro Gln Gly Ile Ile Pro Pro Gly Gly Lys Arg Ser Val Thr
            115                 120                 125
Leu Asn Val Asp Gln Pro Ala Ala Thr Cys Trp Phe His Pro His Gln
        130                 135                 140
His Gly Lys Thr Gly Arg Gln Val Ala Met Gly Leu Ala Gly Leu Val
145                 150                 155                 160
Val Ile Glu Asp Asp Glu Ile Leu Lys Leu Met Leu Pro Lys Gln Trp
                165                 170                 175
Gly Ile Asp Asp Val Pro Val Ile Val Gln Asp Lys Lys Phe Ser Ala
                180                 185                 190
Asp Gly Gln Ile Asp Tyr Gln Leu Asp Val Met Thr Ala Ala Val Gly
            195                 200                 205
Trp Phe Gly Asp Thr Leu Leu Thr Asn Gly Ala Ile Tyr Pro Gln His
        210                 215                 220
Ala Ala Pro Arg Gly Trp Leu Arg Leu Arg Leu Leu Asn Gly Cys Asn
225                 230                 235                 240
Ala Arg Ser Leu Asn Phe Ala Thr Ser Asp Asn Arg Pro Leu Tyr Val
                245                 250                 255
Ile Ala Ser Asp Gly Gly Leu Leu Pro Glu Pro Val Lys Val Ser Glu
            260                 265                 270
Leu Pro Val Leu Met Gly Glu Arg Phe Glu Val Leu Val Glu Val Asn
        275                 280                 285
Asp Asn Lys Pro Phe Asp Leu Val Thr Leu Pro Val Ser Gln Met Gly
    290                 295                 300
Met Ala Ile Ala Pro Phe Asp Lys Pro His Pro Val Met Arg Ile Gln
305                 310                 315                 320
Pro Ile Ala Ile Ser Ala Ser Gly Ala Leu Pro Asp Thr Leu Ser Ser
                325                 330                 335
Leu Pro Ala Leu Pro Ser Leu Glu Gly Leu Thr Val Arg Lys Leu Gln
            340                 345                 350
Leu Ser Met Asp Pro Met Leu Asp Met Met Gly Met Gln Met Leu Met
        355                 360                 365
Glu Lys Tyr Gly Ala Ala Gly Ala Ala Gly Ala Ala Ala Ala Asn Lys
    370                 375                 380
Ile Asn Gly Gln Ala Phe Asp Met Asn Lys Pro Met Phe Ala Ala Ala
385                 390                 395                 400
Lys Gly Gln Tyr Glu Arg Trp Val Ile Ser Gly Val Gly Asp Met Met
                405                 410                 415
Leu His Pro Phe His Ile His Gly Thr Gln Phe Arg Ile Leu Ser Glu
            420                 425                 430
Asn Gly Lys Pro Pro Ala Ala His Arg Ala Gly Trp Lys Asp Thr Val
        435                 440                 445
```

```
Lys Val Glu Gly Asn Val Ser Glu Val Leu Val Lys Phe Asn His Asp
        450                 455                 460

Ala Pro Lys Glu His Ala Tyr Met Ala His Cys His Leu Leu Glu His
465                 470                 475                 480

Glu Asp Thr Gly Met Met Leu Gly Phe Thr Val Gly His His His His
                485                 490                 495

His His

<210> SEQ ID NO 22
<211> LENGTH: 62
<212> TYPE: DNA
<213> ORGANISM: Artificial Sequence
<220> FEATURE:
<223> OTHER INFORMATION: Synthetic primer

<400> SEQUENCE: 22
ctctccatgg acccgatgct cgatatgatg gggatgcaga tgctaatgga gaaatatggc    60
gc                                                                  62

<210> SEQ ID NO 23
<211> LENGTH: 61
<212> TYPE: DNA
<213> ORGANISM: Artificial Sequence
<220> FEATURE:
<223> OTHER INFORMATION: Synthetic primer

<400> SEQUENCE: 23
taaattagcg gccgcagcac ctgcagcacc agctgcgcca tatttctcca ttagcatctg    60
c                                                                   61

<210> SEQ ID NO 24
<211> LENGTH: 132
<212> TYPE: DNA
<213> ORGANISM: Artificial Sequence
<220> FEATURE:
<223> OTHER INFORMATION: Synthetic DNA: added sequence

<400> SEQUENCE: 24
gcggccgcag gagcagcagg agcagcagga gatcaggcga tggccgggat ggatcacagc    60
cagatgatgg gccatatggg gcacggcaat atgaatcata tgaaccacgg cgggaagttc   120
gatttccacc at                                                      132

<210> SEQ ID NO 25
<211> LENGTH: 44
<212> TYPE: PRT
<213> ORGANISM: Artificial Sequence
<220> FEATURE:
<223> OTHER INFORMATION: Synthetic amino acid: added sequence

<400> SEQUENCE: 25

Ala Ala Ala Gly Ala Ala Gly Ala Ala Gly Asp Gln Ala Met Ala Gly
1               5                   10                  15

Met Asp His Ser Gln Met Met Gly His Met Gly His Gly Asn Met Asn
            20                  25                  30

His Met Asn His Gly Gly Lys Phe Asp Phe His His
        35                  40

<210> SEQ ID NO 26
<211> LENGTH: 1554
<212> TYPE: DNA
<213> ORGANISM: Artificial Sequence
<220> FEATURE:
```

<223> OTHER INFORMATION: Synthetic DNA: premature mCueO (4), His-Tag added

<400> SEQUENCE: 26

```
atgcaacgtc gtgatttctt aaaatattcc gtcgcgctgg gtgtggcttc ggctttgccg      60
ctgtggagcc gcgcagtatt tgcggcagaa cgcccaacgt taccgatccc tgatttgctc     120
acgaccgatg cccgtaatcg cattcagtta actattggcg caggccagtc cacctttggc     180
gggaaaactg caactacctg ggctataac ggcaatctgc tggggccggc ggtgaaatta      240
cagcgcggca agcggtaacg gttgatatc tacaaccaac tgacggaaga dacaacgttg      300
cactggcacg ggctggaagt accgggtgaa gtcgacggcg gcccgcaggg aattattccg     360
ccaggtggca agcgctcggt gacgttgaac gttgatcaac tgccgctac ctgctggttc      420
catccgcatc agcacggcaa accgggcga caggtgcga tggggctggc tgggctggtg       480
gtgattgaag atgacgagat cctgaaatta atgctgccaa aacagtgggg tatcgatgat     540
gttccggtga tcgttcagga taagaaattt agcgccgatg gcagattga ttatcaactg      600
gatgtgatga ccgccgccgt gggctggttt ggcgatacgt tgctgaccaa cggtgcaatc    660
tacccgcaac acgctgcccc cgtggttgg ctgcgcctgc gtttgctcaa tggctgtaat      720
gcccgttcgc tcaatttcgc caccagcgac aatcgcccgc tgtatgtgat tgccagcgac    780
ggtgtctctgc tacctgaacc agtgaaggtg agcgaactgc cggtgctgat gggcgagcgt    840
tttgaagtgc tggtggaggt taatgataac aaacccttg acctggtgac gctgccggtc     900
agccagatgg ggatggcgat tgcgccgttt gataagcctc atccggtaat gcggattcag     960
ccgattgcta ttagtgcctc cggtgctttg ccagacacat taagtagcct gcctgcgtta    1020
ccttcgctgg aagggctgac ggtacgcaag ctgcaactct ccatgacgc ggccgcagga    1080
gcagcaggag cagcaggaga tcaggcgatg gccgggatgg atcacagcca gatgatgggc   1140
catatggggc acggcaatat gaatcatatg aaccacggcg gaagttcga tttccaccat    1200
gccaacaaaa tcaacggtca ggcgtttgat atgaacaagc cgatgtttgc ggcggcgaaa   1260
gggcaatacg aacgttgggt tatctctggc gtgggcgaca tgatgctgca tccgttccat   1320
atccacggca cgcagttccg tatcttgtca gaaaatggca aaccgccagc ggctcatcgc   1380
gcgggctgga agataccgt taaggtagaa ggtaatgtca cgaagtgct ggtgaagttt      1440
aatcacgatg caccgaaaga acatgcttat atggcgcact gccatctgct ggagcatgaa   1500
gatacgggga tgatgttagg gtttacggta ggccatcatc atcatcatca ttaa           1554
```

<210> SEQ ID NO 27
<211> LENGTH: 517
<212> TYPE: PRT
<213> ORGANISM: Artificial Sequence
<220> FEATURE:
<223> OTHER INFORMATION: Synthetic amino acid: premature mCueO (4), His-Tag added

<400> SEQUENCE: 27

```
Met Gln Arg Arg Asp Phe Leu Lys Tyr Ser Val Ala Leu Gly Val Ala
1               5                   10                  15

Ser Ala Leu Pro Leu Trp Ser Arg Ala Val Phe Ala Ala Glu Arg Pro
            20                  25                  30

Thr Leu Pro Ile Pro Asp Leu Leu Thr Thr Asp Ala Arg Asn Arg Ile
        35                  40                  45

Gln Leu Thr Ile Gly Ala Gly Gln Ser Thr Phe Gly Gly Lys Thr Ala
    50                  55                  60
```

-continued

```
Thr Thr Trp Gly Tyr Asn Gly Asn Leu Leu Gly Pro Ala Val Lys Leu
 65                  70                  75                  80

Gln Arg Gly Lys Ala Val Thr Val Asp Ile Tyr Asn Gln Leu Thr Glu
                 85                  90                  95

Glu Thr Thr Leu His Trp His Gly Leu Glu Val Pro Gly Glu Val Asp
            100                 105                 110

Gly Gly Pro Gln Gly Ile Ile Pro Pro Gly Gly Lys Arg Ser Val Thr
        115                 120                 125

Leu Asn Val Asp Gln Pro Ala Ala Thr Cys Trp Phe His Pro His Gln
130                 135                 140

His Gly Lys Thr Gly Arg Gln Val Ala Met Gly Leu Ala Gly Leu Val
145                 150                 155                 160

Val Ile Glu Asp Asp Glu Ile Leu Lys Leu Met Leu Pro Lys Gln Trp
                165                 170                 175

Gly Ile Asp Asp Val Pro Val Ile Val Gln Asp Lys Lys Phe Ser Ala
            180                 185                 190

Asp Gly Gln Ile Asp Tyr Gln Leu Asp Val Met Thr Ala Ala Val Gly
        195                 200                 205

Trp Phe Gly Asp Thr Leu Leu Thr Asn Gly Ala Ile Tyr Pro Gln His
210                 215                 220

Ala Ala Pro Arg Gly Trp Leu Arg Leu Arg Leu Leu Asn Gly Cys Asn
225                 230                 235                 240

Ala Arg Ser Leu Asn Phe Ala Thr Ser Asp Asn Arg Pro Leu Tyr Val
                245                 250                 255

Ile Ala Ser Asp Gly Gly Leu Leu Pro Glu Pro Val Lys Val Ser Glu
            260                 265                 270

Leu Pro Val Leu Met Gly Glu Arg Phe Glu Val Leu Val Glu Val Asn
        275                 280                 285

Asp Asn Lys Pro Phe Asp Leu Val Thr Leu Pro Val Ser Gln Met Gly
290                 295                 300

Met Ala Ile Ala Pro Phe Asp Lys Pro His Pro Val Met Arg Ile Gln
305                 310                 315                 320

Pro Ile Ala Ile Ser Ala Ser Gly Ala Leu Pro Asp Thr Leu Ser Ser
                325                 330                 335

Leu Pro Ala Leu Pro Ser Leu Glu Gly Leu Thr Val Arg Lys Leu Gln
            340                 345                 350

Leu Ser Met Asp Ala Ala Ala Gly Ala Ala Gly Ala Ala Gly Asp Gln
        355                 360                 365

Ala Met Ala Gly Met Asp His Ser Gln Met Met Gly His Met Gly His
370                 375                 380

Gly Asn Met Asn His Met Asn His Gly Gly Lys Phe Asp Phe His His
385                 390                 395                 400

Ala Asn Lys Ile Asn Gly Gln Ala Phe Asp Met Asn Lys Pro Met Phe
                405                 410                 415

Ala Ala Ala Lys Gly Gln Tyr Glu Arg Trp Val Ile Ser Gly Val Gly
            420                 425                 430

Asp Met Met Leu His Pro Phe His Ile His Gly Thr Gln Phe Arg Ile
        435                 440                 445

Leu Ser Glu Asn Gly Lys Pro Pro Ala His Arg Ala Gly Trp Lys
450                 455                 460

Asp Thr Val Lys Val Glu Gly Asn Val Ser Glu Val Leu Val Lys Phe
465                 470                 475                 480

Asn His Asp Ala Pro Lys Glu His Ala Tyr Met Ala His Cys His Leu
                485                 490                 495
```

Leu Glu His Glu Asp Thr Gly Met Met Leu Gly Phe Thr Val Gly His
            500                 505                 510

His His His His His
        515

<210> SEQ ID NO 28
<211> LENGTH: 57
<212> TYPE: DNA
<213> ORGANISM: Artificial Sequence
<220> FEATURE:
<223> OTHER INFORMATION: Synthetic primer

<400> SEQUENCE: 28
tatttagcgg ccgcaggagc agcaggagca gcaggagatc aggcgatggc cgggatg        57

<210> SEQ ID NO 29
<211> LENGTH: 17
<212> TYPE: DNA
<213> ORGANISM: Artificial Sequence
<220> FEATURE:
<223> OTHER INFORMATION: Synthetic primer

<400> SEQUENCE: 29
gttttcccag tcacgac                                                    17

<210> SEQ ID NO 30
<211> LENGTH: 39
<212> TYPE: DNA
<213> ORGANISM: Artificial Sequence
<220> FEATURE:
<223> OTHER INFORMATION: Synthetic DNA: added sequence

<400> SEQUENCE: 30
ccgatgctcg atatgatggg gatgggagca ggtgcggcc                            39

<210> SEQ ID NO 31
<211> LENGTH: 13
<212> TYPE: PRT
<213> ORGANISM: Artificial Sequence
<220> FEATURE:
<223> OTHER INFORMATION: Synthetic amino acid: added sequence

<400> SEQUENCE: 31

Pro Met Leu Asp Met Met Gly Met Gly Ala Gly Ala Ala
1               5                   10

<210> SEQ ID NO 32
<211> LENGTH: 1461
<212> TYPE: DNA
<213> ORGANISM: Artificial Sequence
<220> FEATURE:
<223> OTHER INFORMATION: Synthetic DNA: premature mCueO (5), His-Tag
      added

<400> SEQUENCE: 32
atgcaacgtc gtgatttctt aaaatattcc gtcgcgctgg gtgtggcttc ggctttgccg     60
ctgtggagcc gcgcagtatt tgcggcagaa cgcccaacgt taccgatccc tgatttgctc    120
acgaccgatg cccgtaatcg cattcagtta actattggcg caggccagtc cacctttggc    180
gggaaaactg caactacctg gggctataac ggcaatctgc tggggccggc ggtgaaatta    240
cagcgcggca aagcggtaac ggttgatatc tacaaccaac tgacggaaga gacaacgttg    300
cactggcacg gctggaagt accgggtgaa gtcgacggcg cccgcaggg aattattccg    360 ccaggtggca agcgctcggt gacgttgaac gttgatcaac tgccgctac ctgctggttc    420

```
catccgcatc agcacggcaa accgggcga caggtggcga tggggctggc tgggctggtg      480
gtgattgaag atgacgagat cctgaaatta atgctgccaa acagtgggg tatcgatgat     540
gttccggtga tcgttcagga taagaaattt agcgccgatg gcagattga ttatcaactg     600
gatgtgatga ccgccgccgt gggctggttt ggcgatacgt tgctgaccaa cggtgcaatc    660
tacccgcaac acgctgcccc gcgtggttgg ctgcgcctgc gtttgctcaa tggctgtaat    720
gcccgttcgc tcaatttcgc caccagcgac aatcgcccgc tgtatgtgat tgccagcgac    780
ggtggtctgc tacctgaacc agtgaaggtg agcgaactgc cggtgctgat gggcgagcgt    840
tttgaagtgc tggtggaggt taatgataac aaaccctttg acctggtgac gctgccggtc    900
agccagatgg ggatggcgat tgcgccgttt gataagcctc atccggtaat gcggattcag    960
ccgattgcta ttagtgcctc cggtgctttg ccagacacat taagtagcct gcctgcgtta   1020
ccttcgctgg aagggctgac ggtacgcaag ctgcaactct ccatggaccc gatgctcgat   1080
atgatgggga tgggagcagg tgcggccgcc aacaaaatca acggtcaggc gtttgatatg   1140
aacaagccga tgtttgcggc ggcgaaaggg caatacgaac gttgggttat ctctggcgtg   1200
ggcgacatga tgctgcatcc gttccatatc cacggcacgg agttccgtat cttgtcagaa   1260
aatggcaaac cgccagcggc tcatcgcgcg ggctggaaag ataccgttaa ggtagaaggt   1320
aatgtcagcg aagtgctggt gaagtttaat cacgatgcac cgaaagaaca tgcttatatg   1380
gcgcactgcc atctgctgga gcatgaagat acggggatga tgttagggtt tacggtaggc   1440
catcatcatc atcatcatta a                                              1461
```

<210> SEQ ID NO 33
<211> LENGTH: 486
<212> TYPE: PRT
<213> ORGANISM: Artificial Sequence
<220> FEATURE:
<223> OTHER INFORMATION: Synthetic amino acid: premature mCueO (5), His-Tag added

<400> SEQUENCE: 33

```
Met Gln Arg Arg Asp Phe Leu Lys Tyr Ser Val Ala Leu Gly Val Ala
1               5                   10                  15

Ser Ala Leu Pro Leu Trp Ser Arg Ala Val Phe Ala Ala Glu Arg Pro
            20                  25                  30

Thr Leu Pro Ile Pro Asp Leu Leu Thr Thr Asp Ala Arg Asn Arg Ile
        35                  40                  45

Gln Leu Thr Ile Gly Ala Gly Gln Ser Thr Phe Gly Gly Lys Thr Ala
    50                  55                  60

Thr Thr Trp Gly Tyr Asn Gly Asn Leu Gly Pro Ala Val Lys Leu
65                  70                  75                  80

Gln Arg Gly Lys Ala Val Thr Val Asp Ile Tyr Asn Gln Leu Thr Glu
                85                  90                  95

Glu Thr Thr Leu His Trp His Gly Leu Glu Val Pro Gly Glu Val Asp
            100                 105                 110

Gly Gly Pro Gln Gly Ile Ile Pro Pro Gly Gly Lys Arg Ser Val Thr
        115                 120                 125

Leu Asn Val Asp Gln Pro Ala Ala Thr Cys Trp Phe His Pro His Gln
    130                 135                 140

His Gly Lys Thr Gly Arg Gln Val Ala Met Gly Leu Ala Gly Leu Val
145                 150                 155                 160

Val Ile Glu Asp Asp Glu Ile Leu Lys Leu Met Leu Pro Lys Gln Trp
                165                 170                 175
```

```
Gly Ile Asp Asp Val Pro Val Ile Val Gln Asp Lys Lys Phe Ser Ala
                180                 185                 190
Asp Gly Gln Ile Asp Tyr Gln Leu Asp Val Met Thr Ala Ala Val Gly
            195                 200                 205
Trp Phe Gly Asp Thr Leu Leu Thr Asn Gly Ala Ile Tyr Pro Gln His
210                 215                 220
Ala Ala Pro Arg Gly Trp Leu Arg Leu Arg Leu Asn Gly Cys Asn
225                 230                 235                 240
Ala Arg Ser Leu Asn Phe Ala Thr Ser Asp Asn Arg Pro Leu Tyr Val
                245                 250                 255
Ile Ala Ser Asp Gly Leu Leu Pro Glu Pro Val Lys Val Ser Glu
                260                 265                 270
Leu Pro Val Leu Met Gly Glu Arg Phe Glu Val Leu Val Glu Val Asn
            275                 280                 285
Asp Asn Lys Pro Phe Asp Leu Val Thr Leu Pro Val Ser Gln Met Gly
290                 295                 300
Met Ala Ile Ala Pro Phe Asp Lys Pro His Pro Val Met Arg Ile Gln
305                 310                 315                 320
Pro Ile Ala Ile Ser Ala Ser Gly Ala Leu Pro Asp Thr Leu Ser Ser
                325                 330                 335
Leu Pro Ala Leu Pro Ser Leu Glu Gly Leu Thr Val Arg Lys Leu Gln
                340                 345                 350
Leu Ser Met Asp Pro Met Leu Asp Met Met Gly Met Gly Ala Gly Ala
            355                 360                 365
Ala Ala Asn Lys Ile Asn Gly Gln Ala Phe Asp Met Asn Lys Pro Met
370                 375                 380
Phe Ala Ala Ala Lys Gly Gln Tyr Glu Arg Trp Val Ile Ser Gly Val
385                 390                 395                 400
Gly Asp Met Met Leu His Pro Phe His Ile His Gly Thr Gln Phe Arg
                405                 410                 415
Ile Leu Ser Glu Asn Gly Lys Pro Pro Ala Ala His Arg Ala Gly Trp
                420                 425                 430
Lys Asp Thr Val Lys Val Glu Gly Asn Val Ser Glu Val Leu Val Lys
            435                 440                 445
Phe Asn His Asp Ala Pro Lys Glu His Ala Tyr Met Ala His Cys His
        450                 455                 460
Leu Leu Glu His Glu Asp Thr Gly Met Met Leu Gly Phe Thr Val Gly
465                 470                 475                 480
His His His His His His
            485

<210> SEQ ID NO 34
<211> LENGTH: 39
<212> TYPE: DNA
<213> ORGANISM: Artificial Sequence
<220> FEATURE:
<223> OTHER INFORMATION: Synthetic primer

<400> SEQUENCE: 34
ctctccatgg acccgatgct cgatatgatg gggatggga                              39

<210> SEQ ID NO 35
<211> LENGTH: 39
<212> TYPE: DNA
<213> ORGANISM: Artificial Sequence
<220> FEATURE:
<223> OTHER INFORMATION: Synthetic primer
```

<400> SEQUENCE: 35
aataatagcg gccgcacctg ctcccatccc catcatatc            39

<210> SEQ ID NO 36
<211> LENGTH: 440
<212> TYPE: PRT
<213> ORGANISM: Artificial Sequence
<220> FEATURE:
<223> OTHER INFORMATION: Synthetic amino acid: mature mCueO (2)

<400> SEQUENCE: 36

```
Ala Glu Arg Pro Thr Leu Pro Ile Pro Asp Leu Leu Thr Thr Asp Ala
1               5                   10                  15

Arg Asn Arg Ile Gln Leu Thr Ile Gly Ala Gly Gln Ser Thr Phe Gly
            20                  25                  30

Gly Lys Thr Ala Thr Thr Trp Gly Tyr Asn Gly Asn Leu Leu Gly Pro
        35                  40                  45

Ala Val Lys Leu Gln Arg Gly Lys Ala Val Thr Val Asp Ile Tyr Asn
    50                  55                  60

Gln Leu Thr Glu Glu Thr Thr Leu His Trp His Gly Leu Glu Val Pro
65                  70                  75                  80

Gly Glu Val Asp Gly Pro Gln Gly Ile Ile Pro Pro Gly Gly Lys
                85                  90                  95

Arg Ser Val Thr Leu Asn Val Asp Gln Pro Ala Ala Thr Cys Trp Phe
            100                 105                 110

His Pro His Gln His Gly Lys Thr Gly Arg Gln Val Ala Met Gly Leu
        115                 120                 125

Ala Gly Leu Val Val Ile Glu Asp Asp Glu Ile Leu Lys Leu Met Leu
    130                 135                 140

Pro Lys Gln Trp Gly Ile Asp Asp Val Pro Val Ile Val Gln Asp Lys
145                 150                 155                 160

Lys Phe Ser Ala Asp Gly Gln Ile Asp Tyr Gln Leu Asp Val Met Thr
                165                 170                 175

Ala Ala Val Gly Trp Phe Gly Asp Thr Leu Leu Thr Asn Gly Ala Ile
            180                 185                 190

Tyr Pro Gln His Ala Ala Pro Arg Gly Trp Leu Arg Leu Arg Leu Leu
        195                 200                 205

Asn Gly Cys Asn Ala Arg Ser Leu Asn Phe Ala Thr Ser Asp Asn Arg
    210                 215                 220

Pro Leu Tyr Val Ile Ala Ser Asp Gly Gly Leu Leu Pro Glu Pro Val
225                 230                 235                 240

Lys Val Ser Glu Leu Pro Val Leu Met Gly Glu Arg Phe Glu Val Leu
                245                 250                 255

Val Glu Val Asn Asp Asn Lys Pro Phe Asp Leu Val Thr Leu Pro Val
            260                 265                 270

Ser Gln Met Gly Met Ala Ile Ala Pro Phe Asp Lys Pro His Pro Val
        275                 280                 285

Met Arg Ile Gln Pro Ile Ala Ile Ser Ala Ser Gly Ala Leu Pro Asp
    290                 295                 300

Thr Leu Ser Ser Leu Pro Ala Leu Pro Ser Leu Glu Gly Leu Thr Val
305                 310                 315                 320

Arg Lys Leu Gln Leu Ser Met Asp Ala Ala Ala Asn Lys Ile Asn Gly
                325                 330                 335

Gln Ala Phe Asp Met Asn Lys Pro Met Phe Ala Ala Ala Lys Gly Gln
            340                 345                 350
```

```
Tyr Glu Arg Trp Val Ile Ser Gly Val Gly Asp Met Met Leu His Pro
                355                 360                 365

Phe His Ile His Gly Thr Gln Phe Arg Ile Leu Ser Glu Asn Gly Lys
            370                 375                 380

Pro Pro Ala Ala His Arg Ala Gly Trp Lys Asp Thr Val Lys Val Glu
385                 390                 395                 400

Gly Asn Val Ser Glu Val Leu Val Lys Phe Asn His Asp Ala Pro Lys
                405                 410                 415

Glu His Ala Tyr Met Ala His Cys His Leu Leu Glu His Glu Asp Thr
            420                 425                 430

Gly Met Met Leu Gly Phe Thr Val
                435                 440

<210> SEQ ID NO 37
<211> LENGTH: 463
<212> TYPE: PRT
<213> ORGANISM: Artificial Sequence
<220> FEATURE:
<223> OTHER INFORMATION: Synthetic amino acid: mature mCueO (3)

<400> SEQUENCE: 37

Ala Glu Arg Pro Thr Leu Pro Ile Pro Asp Leu Leu Thr Thr Asp Ala
1               5                   10                  15

Arg Asn Arg Ile Gln Leu Thr Ile Gly Ala Gly Gln Ser Thr Phe Gly
                20                  25                  30

Gly Lys Thr Ala Thr Thr Trp Gly Tyr Asn Gly Asn Leu Leu Gly Pro
            35                  40                  45

Ala Val Lys Leu Gln Arg Gly Lys Ala Val Thr Val Asp Ile Tyr Asn
        50                  55                  60

Gln Leu Thr Glu Glu Thr Thr Leu His Trp His Gly Leu Glu Val Pro
65                  70                  75                  80

Gly Glu Val Asp Gly Gly Pro Gln Gly Ile Ile Pro Pro Gly Gly Lys
                85                  90                  95

Arg Ser Val Thr Leu Asn Val Asp Gln Pro Ala Ala Thr Cys Trp Phe
                100                 105                 110

His Pro His Gln His Gly Lys Thr Gly Arg Gln Val Ala Met Gly Leu
            115                 120                 125

Ala Gly Leu Val Val Ile Glu Asp Asp Glu Ile Leu Lys Leu Met Leu
        130                 135                 140

Pro Lys Gln Trp Gly Ile Asp Asp Val Pro Val Ile Val Gln Asp Lys
145                 150                 155                 160

Lys Phe Ser Ala Asp Gly Gln Ile Asp Tyr Gln Leu Asp Val Met Thr
                165                 170                 175

Ala Ala Val Gly Trp Phe Gly Asp Thr Leu Leu Thr Asn Gly Ala Ile
            180                 185                 190

Tyr Pro Gln His Ala Ala Pro Arg Gly Trp Leu Arg Leu Arg Leu Leu
        195                 200                 205

Asn Gly Cys Asn Ala Arg Ser Leu Asn Phe Ala Thr Ser Asp Asn Arg
    210                 215                 220

Pro Leu Tyr Val Ile Ala Ser Asp Gly Gly Leu Leu Pro Glu Pro Val
225                 230                 235                 240

Lys Val Ser Glu Leu Pro Val Leu Met Gly Glu Arg Phe Glu Val Leu
                245                 250                 255

Val Glu Val Asn Asp Asn Lys Pro Phe Asp Leu Val Thr Leu Pro Val
                260                 265                 270
```

```
Ser Gln Met Gly Met Ala Ile Ala Pro Phe Asp Lys Pro His Pro Val
        275                 280                 285

Met Arg Ile Gln Pro Ile Ala Ile Ser Ala Ser Gly Ala Leu Pro Asp
    290                 295                 300

Thr Leu Ser Ser Leu Pro Ala Leu Pro Ser Leu Glu Gly Leu Thr Val
305                 310                 315                 320

Arg Lys Leu Gln Leu Ser Met Asp Pro Met Leu Asp Met Met Gly Met
                325                 330                 335

Gln Met Leu Met Glu Lys Tyr Gly Ala Ala Gly Ala Ala Gly Ala Ala
            340                 345                 350

Ala Ala Asn Lys Ile Asn Gly Gln Ala Phe Asp Met Asn Lys Pro Met
        355                 360                 365

Phe Ala Ala Ala Lys Gly Gln Tyr Glu Arg Trp Val Ile Ser Gly Val
    370                 375                 380

Gly Asp Met Met Leu His Pro Phe His Ile His Gly Thr Gln Phe Arg
385                 390                 395                 400

Ile Leu Ser Glu Asn Gly Lys Pro Pro Ala Ala His Arg Ala Gly Trp
                405                 410                 415

Lys Asp Thr Val Lys Val Glu Gly Asn Val Ser Glu Val Leu Val Lys
            420                 425                 430

Phe Asn His Asp Ala Pro Lys Glu His Ala Tyr Met Ala His Cys His
        435                 440                 445

Leu Leu Glu His Glu Asp Thr Gly Met Met Leu Gly Phe Thr Val
    450                 455                 460

<210> SEQ ID NO 38
<211> LENGTH: 482
<212> TYPE: PRT
<213> ORGANISM: Artificial Sequence
<220> FEATURE:
<223> OTHER INFORMATION: Synthetic amino acid: mature mCueO (4)

<400> SEQUENCE: 38

Ala Glu Arg Pro Thr Leu Pro Ile Pro Asp Leu Leu Thr Thr Asp Ala
1               5                   10                  15

Arg Asn Arg Ile Gln Leu Thr Ile Gly Ala Gly Gln Ser Thr Phe Gly
            20                  25                  30

Gly Lys Thr Ala Thr Thr Trp Gly Tyr Asn Gly Asn Leu Leu Gly Pro
        35                  40                  45

Ala Val Lys Leu Gln Arg Gly Lys Ala Val Thr Val Asp Ile Tyr Asn
    50                  55                  60

Gln Leu Thr Glu Glu Thr Thr Leu His Trp His Gly Leu Glu Val Pro
65                  70                  75                  80

Gly Glu Val Asp Gly Gly Pro Gln Gly Ile Ile Pro Pro Gly Gly Lys
                85                  90                  95

Arg Ser Val Thr Leu Asn Val Asp Gln Pro Ala Ala Thr Cys Trp Phe
            100                 105                 110

His Pro His Gln His Gly Lys Thr Gly Arg Gln Val Ala Met Gly Leu
        115                 120                 125

Ala Gly Leu Val Val Ile Glu Asp Asp Glu Ile Leu Lys Leu Met Leu
    130                 135                 140

Pro Lys Gln Trp Gly Ile Asp Asp Val Pro Val Ile Val Gln Asp Lys
145                 150                 155                 160

Lys Phe Ser Ala Asp Gly Gln Ile Asp Tyr Gln Leu Asp Val Met Thr
                165                 170                 175

Ala Ala Val Gly Trp Phe Gly Asp Thr Leu Leu Thr Asn Gly Ala Ile
```

```
                        180                 185                 190
Tyr Pro Gln His Ala Ala Pro Arg Gly Trp Leu Arg Leu Arg Leu Leu
                195                 200                 205

Asn Gly Cys Asn Ala Arg Ser Leu Asn Phe Ala Thr Ser Asp Asn Arg
            210                 215                 220

Pro Leu Tyr Val Ile Ala Ser Asp Gly Gly Leu Leu Pro Glu Pro Val
225                 230                 235                 240

Lys Val Ser Glu Leu Pro Val Leu Met Gly Glu Arg Phe Glu Val Leu
                245                 250                 255

Val Glu Val Asn Asp Asn Lys Pro Phe Asp Leu Val Thr Leu Pro Val
            260                 265                 270

Ser Gln Met Gly Met Ala Ile Ala Pro Phe Asp Lys Pro His Pro Val
            275                 280                 285

Met Arg Ile Gln Pro Ile Ala Ile Ser Ala Ser Gly Ala Leu Pro Asp
        290                 295                 300

Thr Leu Ser Ser Leu Pro Ala Leu Pro Ser Leu Glu Gly Leu Thr Val
305                 310                 315                 320

Arg Lys Leu Gln Leu Ser Met Asp Ala Ala Gly Ala Ala Gly Ala
                325                 330                 335

Ala Gly Asp Gln Ala Met Ala Gly Met Asp His Ser Gln Met Met Gly
            340                 345                 350

His Met Gly His Gly Asn Met Asn His Met Asn His Gly Gly Lys Phe
            355                 360                 365

Asp Phe His His Ala Asn Lys Ile Asn Gly Gln Ala Phe Asp Met Asn
        370                 375                 380

Lys Pro Met Phe Ala Ala Lys Gly Gln Tyr Glu Arg Trp Val Ile
385                 390                 395                 400

Ser Gly Val Gly Asp Met Met Leu His Pro Phe His Ile His Gly Thr
                405                 410                 415

Gln Phe Arg Ile Leu Ser Glu Asn Gly Lys Pro Pro Ala Ala His Arg
            420                 425                 430

Ala Gly Trp Lys Asp Thr Val Lys Val Glu Gly Asn Val Ser Glu Val
        435                 440                 445

Leu Val Lys Phe Asn His Asp Ala Pro Lys Gly His Ala Tyr Met Ala
450                 455                 460

His Cys His Leu Leu Glu His Glu Asp Thr Gly Met Met Leu Gly Phe
465                 470                 475                 480

Thr Val

<210> SEQ ID NO 39
<211> LENGTH: 451
<212> TYPE: PRT
<213> ORGANISM: Artificial Sequence
<220> FEATURE:
<223> OTHER INFORMATION: Synthetic amino acid: mature mCueO (5)

<400> SEQUENCE: 39

Ala Glu Arg Pro Thr Leu Pro Ile Pro Asp Leu Leu Thr Thr Asp Ala
1               5                   10                  15

Arg Asn Arg Ile Gln Leu Thr Ile Gly Ala Gly Gln Ser Thr Phe Gly
            20                  25                  30

Gly Lys Thr Ala Thr Thr Trp Gly Tyr Asn Gly Asn Leu Leu Gly Pro
        35                  40                  45

Ala Val Lys Leu Gln Arg Gly Lys Ala Val Thr Val Asp Ile Tyr Asn
    50                  55                  60
```

Gln Leu Thr Glu Glu Thr Thr Leu His Trp His Gly Leu Glu Val Pro
 65                  70                  75                  80

Gly Glu Val Asp Gly Pro Gln Gly Ile Pro Pro Gly Gly Lys
             85                  90                  95

Arg Ser Val Thr Leu Asn Val Asp Gln Pro Ala Ala Thr Cys Trp Phe
             100                 105                 110

His Pro His Gln His Gly Lys Thr Gly Arg Gln Val Ala Met Gly Leu
             115                 120                 125

Ala Gly Leu Val Val Ile Glu Asp Glu Ile Leu Lys Leu Met Leu
130                 135                 140

Pro Lys Gln Trp Gly Ile Asp Asp Val Pro Val Ile Val Gln Asp Lys
145                 150                 155                 160

Lys Phe Ser Ala Asp Gly Gln Ile Asp Tyr Gln Leu Asp Val Met Thr
             165                 170                 175

Ala Ala Val Gly Trp Phe Gly Asp Thr Leu Leu Thr Asn Gly Ala Ile
             180                 185                 190

Tyr Pro Gln His Ala Ala Pro Arg Gly Trp Leu Arg Leu Arg Leu Leu
             195                 200                 205

Asn Gly Cys Asn Ala Arg Ser Leu Asn Phe Ala Thr Ser Asp Asn Arg
210                 215                 220

Pro Leu Tyr Val Ile Ala Ser Asp Gly Gly Leu Leu Pro Glu Pro Val
225                 230                 235                 240

Lys Val Ser Glu Leu Pro Val Leu Met Gly Glu Arg Phe Glu Val Leu
             245                 250                 255

Val Glu Val Asn Asp Asn Lys Pro Phe Asp Leu Val Thr Leu Pro Val
             260                 265                 270

Ser Gln Met Gly Met Ala Ile Ala Pro Phe Asp Lys Pro His Pro Val
             275                 280                 285

Met Arg Ile Gln Pro Ile Ala Ile Ser Ala Ser Gly Ala Leu Pro Asp
290                 295                 300

Thr Leu Ser Ser Leu Pro Ala Leu Pro Ser Leu Glu Gly Leu Thr Val
305                 310                 315                 320

Arg Lys Leu Gln Leu Ser Met Asp Pro Met Leu Asp Met Met Gly Met
             325                 330                 335

Gly Ala Gly Ala Ala Asn Lys Ile Asn Gly Gln Ala Phe Asp Met
             340                 345                 350

Asn Lys Pro Met Phe Ala Ala Lys Gly Gln Tyr Glu Arg Trp Val
             355                 360                 365

Ile Ser Gly Val Gly Asp Met Met Leu His Pro Phe His Ile His Gly
             370                 375                 380

Thr Gln Phe Arg Ile Leu Ser Glu Asn Gly Lys Pro Pro Ala Ala His
385                 390                 395                 400

Arg Ala Gly Trp Lys Asp Thr Val Lys Val Glu Gly Asn Val Ser Glu
             405                 410                 415

Val Leu Val Lys Phe Asn His Asp Ala Pro Lys Glu His Ala Tyr Met
             420                 425                 430

Ala His Cys His Leu Leu Glu His Glu Asp Thr Gly Met Met Leu Gly
             435                 440                 445

Phe Thr Val
     450

<210> SEQ ID NO 40
<211> LENGTH: 1428
<212> TYPE: DNA
<213> ORGANISM: Artificial Sequence

```
<220> FEATURE:
<223> OTHER INFORMATION: Synthetic DNA: premature mCueO (1), His-Tag
      added

<400> SEQUENCE: 40
atgcaacgtc gtgatttctt aaaatattcc gtcgcgctgg gtgtggcttc ggctttgccg      60
ctgtggagcc gcgcagtatt tgcggcagaa cgcccaacgt taccgatccc tgatttgctc     120
acgaccgatg cccgtaatcg cattcagtta actattggcg caggccagtc cacctttggc     180
gggaaaactg caactacctg ggctataacg gcaatctgc tggggccggc ggtgaaatta      240
cagcgcggca aagcggtaac ggttgatatc tacaaccaac tgacggaaga dcaacgttg      300
cactggcacg ggctggaagt accgggtgaa gtcgacggcg gcccgcaggg aattattccg     360
ccaggtggca agcgctcggt gacgttgaac gttgatcaac ctgccgctac ctgctggttc     420
catccgcatc agcacggcaa accgggcga caggtggcga tggggctggc tgggctggtg      480
gtgattgaag atgacgagat cctgaaatta atgctgccaa acagtgggg tatcgatgat      540
gttccggtga tcgttcagga taagaaattt agcgccgatg gcagattga ttatcaactg      600
gatgtgatga ccgccgccgt gggctggttt ggcgatacgt tgctgaccaa cggtgcaatc     660
tacccgcaac acgctgcccc gcgtggttgg ctgcgcctgc gttgctcaa tggctgtaat      720
gcccgttcgc tcaatttcgc caccagcgac aatcgcccgc tgtatgtgat tgccagcgac     780
ggtggtctgc tacctgaacc agtgaaggtg agcgaactgc cggtgctgat gggcgagcgt     840
tttgaagtgc tggtggaggt taatgataac aaacccttg acctggtgac gctgccggtc      900
agccagatgg ggatggcgat tgcgccgttt gataagcctc atccggtaat gcggattcag     960
ccgattgcta ttagtgcctc cggtgctttg ccagacacat taagtagcct gcctgcgtta    1020
ccttcgctgg aagggctgac ggtacgcaag ctgcaactct ccatggacgg tggtgccaac    1080
aaaatcaacg tcaggcgtt tgatatgaac aagccgatgt ttgcggcggc gaaagggcaa     1140
tacgaacgtt gggttatctc tggcgtgggc gacatgatgc tgcatccgtt ccatatccac    1200
ggcacgcagt ccgtatcttt gtcagaaaat ggcaaaccgc cagcggctca tcgcgcgggc    1260
tggaaagata ccgttaaggt agaaggtaat gtcagcgaag tgctggtgaa gtttaatcac    1320
gatgcaccga agaacatgc ttatatggcg cactgccatc tgctggagca tgaagatacg     1380
gggatgatgt tagggtttac ggtaggccat catcatcatc atcattaa                  1428

<210> SEQ ID NO 41
<211> LENGTH: 475
<212> TYPE: PRT
<213> ORGANISM: Artificial Sequence
<220> FEATURE:
<223> OTHER INFORMATION: Synthetic amino acid: premature mCueO (1),
      His-Tag added

<400> SEQUENCE: 41

Met Gln Arg Arg Asp Phe Leu Lys Tyr Ser Val Ala Leu Gly Val Ala
1               5                   10                  15

Ser Ala Leu Pro Leu Trp Ser Arg Ala Val Phe Ala Ala Glu Arg Pro
            20                  25                  30

Thr Leu Pro Ile Pro Asp Leu Leu Thr Thr Asp Ala Arg Asn Arg Ile
        35                  40                  45

Gln Leu Thr Ile Gly Ala Gly Gln Ser Thr Phe Gly Gly Lys Thr Ala
    50                  55                  60

Thr Thr Trp Gly Tyr Asn Gly Asn Leu Leu Gly Pro Ala Val Lys Leu
65                  70                  75                  80
```

```
Gln Arg Gly Lys Ala Val Thr Val Asp Ile Tyr Asn Gln Leu Thr Glu
                 85                  90                  95

Glu Thr Thr Leu His Trp His Gly Leu Glu Val Pro Gly Glu Val Asp
            100                 105                 110

Gly Gly Pro Gln Gly Ile Ile Pro Pro Gly Gly Lys Arg Ser Val Thr
        115                 120                 125

Leu Asn Val Asp Gln Pro Ala Ala Thr Cys Trp Phe His Pro His Gln
    130                 135                 140

His Gly Lys Thr Gly Arg Gln Val Ala Met Gly Leu Ala Gly Leu Val
145                 150                 155                 160

Val Ile Glu Asp Asp Glu Ile Leu Lys Leu Met Leu Pro Lys Gln Trp
                165                 170                 175

Gly Ile Asp Asp Val Pro Val Ile Val Gln Asp Lys Lys Phe Ser Ala
            180                 185                 190

Asp Gly Gln Ile Asp Tyr Gln Leu Asp Val Met Thr Ala Ala Val Gly
        195                 200                 205

Trp Phe Gly Asp Thr Leu Leu Thr Asn Gly Ala Ile Tyr Pro Gln His
    210                 215                 220

Ala Ala Pro Arg Gly Trp Leu Arg Leu Arg Leu Asn Gly Cys Asn
225                 230                 235                 240

Ala Arg Ser Leu Asn Phe Ala Thr Ser Asp Asn Arg Pro Leu Tyr Val
                245                 250                 255

Ile Ala Ser Asp Gly Gly Leu Leu Pro Glu Pro Val Lys Val Ser Glu
            260                 265                 270

Leu Pro Val Leu Met Gly Glu Arg Phe Glu Val Leu Glu Val Asn
        275                 280                 285

Asp Asn Lys Pro Phe Asp Leu Val Thr Leu Pro Val Ser Gln Met Gly
    290                 295                 300

Met Ala Ile Ala Pro Phe Asp Lys Pro His Pro Val Met Arg Ile Gln
305                 310                 315                 320

Pro Ile Ala Ile Ser Ala Ser Gly Ala Leu Pro Asp Thr Leu Ser Ser
                325                 330                 335

Leu Pro Ala Leu Pro Ser Leu Glu Gly Leu Thr Val Arg Lys Leu Gln
            340                 345                 350

Leu Ser Met Asp Gly Gly Ala Asn Lys Ile Asn Gly Gln Ala Phe Asp
        355                 360                 365

Met Asn Lys Pro Met Phe Ala Ala Lys Gly Gln Tyr Glu Arg Trp
    370                 375                 380

Val Ile Ser Gly Val Gly Asp Met Met Leu His Pro Phe His Ile His
385                 390                 395                 400

Gly Thr Gln Phe Arg Ile Leu Ser Glu Asn Gly Lys Pro Pro Ala Ala
                405                 410                 415

His Arg Ala Gly Trp Lys Asp Thr Val Lys Val Glu Gly Asn Val Ser
            420                 425                 430

Glu Val Leu Val Lys Phe Asn His Asp Ala Pro Lys Glu His Ala Tyr
        435                 440                 445

Met Ala His Cys His Leu Leu Glu His Glu Asp Thr Gly Met Met Leu
    450                 455                 460

Gly Phe Thr Val Gly His His His His His
465                 470                 475

<210> SEQ ID NO 42
<211> LENGTH: 9
<212> TYPE: PRT
<213> ORGANISM: Artificial Sequence
```

-continued

```
<220> FEATURE:
<223> OTHER INFORMATION: Synthetic spacer peptide

<400> SEQUENCE: 42

Ala Ala Gly Ala Ala Gly Ala Ala Ala
1               5

<210> SEQ ID NO 43
<211> LENGTH: 10
<212> TYPE: PRT
<213> ORGANISM: Artificial Sequence
<220> FEATURE:
<223> OTHER INFORMATION: Synthetic spacer peptide

<400> SEQUENCE: 43

Ala Ala Ala Gly Ala Ala Gly Ala Ala Gly
1               5                   10
```